United States Patent
Baran

(10) Patent No.: US 6,526,976 B1
(45) Date of Patent: *Mar. 4, 2003

(54) NEBULIZING CATHETER SYSTEM AND METHOD OF USE AND MANUFACTURE

(75) Inventor: George Baran, London (CA)

(73) Assignee: Trudell Medical Limited, London (CA)

(*) Notice: Subject to any disclaimer, the term of this patent is extended or adjusted under 35 U.S.C. 154(b) by 0 days.

This patent is subject to a terminal disclaimer.

(21) Appl. No.: 09/265,602

(22) Filed: Mar. 10, 1999

Related U.S. Application Data

(63) Continuation of application No. 08/787,813, filed on Jan. 23, 1997, now Pat. No. 5,964,223, and a continuation of application No. 08/261,866, filed on Jun. 17, 1994, now abandoned.

(51) Int. Cl.[7] ............................................. A61M 16/00
(52) U.S. Cl. ........................... 128/207.14; 128/200.14; 128/200.16
(58) Field of Search ................... 128/200.14, 200.22, 128/200.23, 203.12, 200.16, 200.26, 207.14

(56) References Cited

U.S. PATENT DOCUMENTS

| | | |
|---|---|---|
| 2,638,096 A | 5/1953 | Waldhaus |
| 3,788,326 A | 1/1974 | Jacobs |
| 4,270,530 A | 6/1981 | Baum et al. |
| 4,319,115 A | 3/1982 | Nakai et al. |
| 4,327,721 A | 5/1982 | Goldin et al. |
| 4,584,998 A | 4/1986 | McGrail |
| 4,646,733 A | 3/1987 | Stroh et al. |

(List continued on next page.)

FOREIGN PATENT DOCUMENTS

| | | |
|---|---|---|
| EP | 0 289 336 A2 | 2/1988 |
| EP | 0 445 502 | 9/1991 |

(List continued on next page.)

OTHER PUBLICATIONS

Hoover et al., "A Microspray Nozzle for Local Administration of Liquids or Suspensions to Lung Airways via Bronchoscopy," Journal of Aerosol Medicine, vol. 6, #2, 1993.

(List continued on next page.)

*Primary Examiner*—Aaron J. Lewis
(74) *Attorney, Agent, or Firm*—Brinks Hofer Gilson & Lione

(57) ABSTRACT

A method and apparatus for delivering a medicine to a patient via the patient's respiratory system with control and efficiency. A nebulization catheter is positioned in the patient's respiratory system so that a distal end of the nebulization catheter is in the respiratory system and a proximal end is outside the body. In a first aspect, the nebulization catheter may be used in conjunction with an endotracheal tube and preferably is removable from the endotracheal tube. The nebulization catheter conveys medicine in liquid form to the distal end at which location the medicine is nebulized by a pressurized gas or other nebulizing mechanism. The nebulized medicine is conveyed to the patient's lungs by the patient's respiration which may be assisted by a ventilator. By producing the aerosol of the liquid medicine at a location inside the patient's respiratory system, the nebulizing catheter provides for increased efficiency and control of the dosage of medicine being delivered. In further aspects of the nebulizing catheter apparatus and method, alternative tip constructions, flow pulsation patterns, centering devices, sensing devices, and aspiration features afford greater efficiency and control of aerosolized medicine dosage delivery.

44 Claims, 28 Drawing Sheets

U.S. PATENT DOCUMENTS

| | | | |
|---|---|---|---|
| 4,655,746 A | | 4/1987 | Daniels et al. |
| 4,669,463 A | | 6/1987 | McConnell |
| 4,739,756 A | | 4/1988 | Horn |
| 4,805,609 A | | 2/1989 | Roberts et al. |
| 4,819,664 A | | 4/1989 | Nazari |
| 4,821,714 A | | 4/1989 | Smelser |
| 4,829,996 A | | 5/1989 | Noakes et al. |
| 4,832,012 A | | 5/1989 | Raabe et al. |
| 4,881,542 A | | 11/1989 | Schmidt et al. |
| 4,886,055 A | | 12/1989 | Hoppough |
| 4,945,929 A | | 8/1990 | Egilmex |
| 4,955,375 A | | 9/1990 | Martinez |
| 5,012,804 A | | 5/1991 | Foley et al. |
| 5,025,806 A | | 6/1991 | Palmer et al. |
| 5,029,580 A | | 7/1991 | Radford et al. |
| 5,031,613 A | | 7/1991 | Smith et al. |
| 5,049,137 A | | 9/1991 | Thompson |
| 5,060,646 A | | 10/1991 | Page |
| 5,062,423 A | | 11/1991 | Matson et al. |
| 5,072,726 A | | 12/1991 | Mazloomdoost et al. |
| 5,078,131 A | | 1/1992 | Foley |
| 5,115,971 A | | 5/1992 | Greenspan et al. |
| 5,116,088 A | | 5/1992 | Bird |
| 5,119,807 A | | 6/1992 | Roberts |
| 5,125,893 A | | 6/1992 | Dryden |
| 5,146,916 A | | 9/1992 | Catalani |
| 5,152,277 A | | 10/1992 | Honda et al. |
| 5,158,536 A | | 10/1992 | Sekins et al. |
| 5,167,622 A | | 12/1992 | Muto |
| 5,178,138 A | | 1/1993 | Walstrom et al. |
| 5,186,166 A | | 2/1993 | Riggs et al. |
| 5,207,220 A | | 5/1993 | Long |
| 5,231,983 A | | 8/1993 | Matson et al. |
| 5,233,979 A | | 8/1993 | Strickland |
| 5,261,892 A | | 11/1993 | Bertaud et al. |
| 5,287,847 A | | 2/1994 | Piper et al. |
| 5,287,850 A | | 2/1994 | Haber et al. |
| 5,291,882 A | | 3/1994 | Makhoul et al. |
| 5,313,939 A | | 5/1994 | Gonzalez |
| 5,333,607 A | | 8/1994 | Kee et al. |
| 5,372,131 A | | 12/1994 | Heinen, Jr. |
| 5,433,195 A | | 7/1995 | Kee et al. |
| 5,499,625 A | | 3/1996 | Frass et al. |
| 5,803,078 A | | 9/1998 | Brauner |
| 5,964,223 A | * | 10/1999 | Baran .................... 128/207.14 |
| 6,079,413 A | * | 6/2000 | Baran .................... 128/207.14 |
| 6,082,361 A | * | 7/2000 | Morejon ................ 128/207.14 |
| 6,086,529 A | * | 7/2000 | Arndt .................... 128/207.14 |
| 6,102,042 A | * | 8/2000 | Hete et al. ............. 128/207.14 |
| 6,237,597 B1 | * | 5/2001 | Kovac ................... 128/207.14 |
| 6,257,236 B1 | * | 7/2001 | Dutkiewicz ........... 128/207.14 |

FOREIGN PATENT DOCUMENTS

| | | |
|---|---|---|
| EP | 0 453 234 | 10/1991 |
| EP | 0 487 155 | 5/1992 |
| EP | 0 587 380 A1 | 3/1994 |
| EP | 0587380 | 3/1994 |
| FR | 2 569 114 | 8/1984 |
| GB | 2 098 485 | 2/1984 |
| GB | 2 268 286 | 9/1992 |
| RU | 185442 | 8/1966 |
| RU | 812296 | 3/1981 |
| WO | WO 87/05522 | 9/1987 |
| WO | WO 90/07951 | 7/1990 |
| WO | WO 9317744 | 9/1993 |
| WO | WO 95/30448 | 11/1995 |

OTHER PUBLICATIONS

Wheeldon et al., Aerosolized Endotoxin in Animals, (1992).

Carlton, Graziano C.; Barker, Robert L.; Benua, Richard S.; Guy, Yvonne G; Airway Humidification With High–Frequency Jet Ventilation, *Critical Care Medicine*, vol. 13, No. 2, (1985).

Aiache, Jean–Marc; The Ideal Drug Delivery System: A Look into the Future, *Journal of Aerosol Medicine*, vol. 4, No. 4, 1991.

Wheeldon, Walker, Murphy, and Turner; Aerosolized Endotoxin in Animals, (1992).

Jager–Waldau, Reinhold; A Two–Phase–Flow Mechanical Spray Pump: A Possible Alternative To Propellant–Driven MDIs. *Journal of Biopharmaceutical Sciences*, 3(1/2), 077–084, (1992).

Niven, Ralph W.; Kacmarek, Robert M.; Brain, Joseph D.; Peterfreund, Robert A.; Small Bore Nozzle Extensions to Improve the Delivery Efficiency of Drugs from Metered Dose Inhalers: Laboratory Evaluation. *Am Rev Respir Dis*, vol. 147. pp. 1590–1594, 1993.

Taylor, Robert H.; Lerman; Jerrold; Chambers, Carole; Dolovich, Myrna; Dosing Efficiency and Particle–Size Characteristics of Pressurized Metered–Dose Inhaler Aerosols in Narrow Catheters. Presented at Annual Meeting American Society of Anesthesiologist, Las Vegas, Oct. 1990.

Hess, Dean; Inhaled Bronchodilators During Medical Ventilation: Delivery Techniques, Evaluation of Response, and Cost Effectiveness, *Respiratory Care*, vol. 39 No. 2, Feb. 1994.

Judson, Marc A.; Sahan, Steven A.; Mobilization of Secretions in ICU Patients, *Respiratory Care*, vol. 39 No. 3, Mar. 1994.

Copy of packaging for "ENDO–JECT by Autovage", believed to have been published prior to Jun. 17, 1994, 2 pages.

Copy of packaging for "EMT Emergency Medicine Tube", by Mallinckrodt Medical, dated Jan. 1993, 4 pages.

* cited by examiner

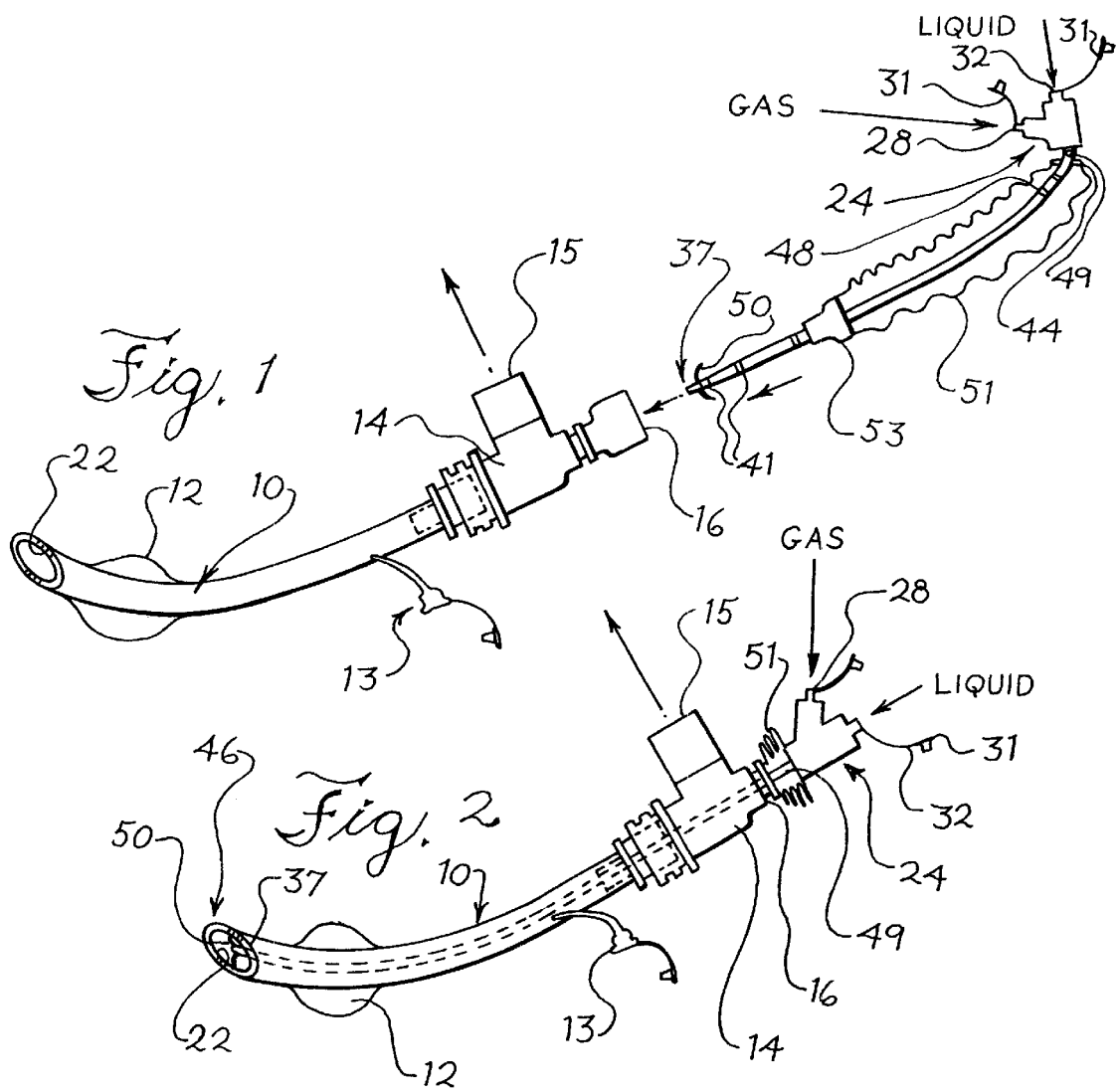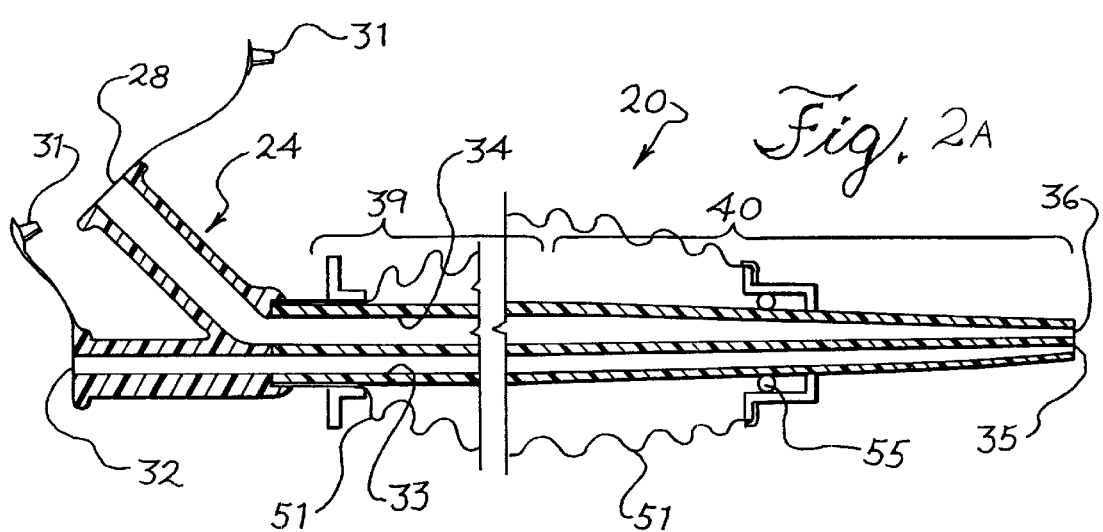

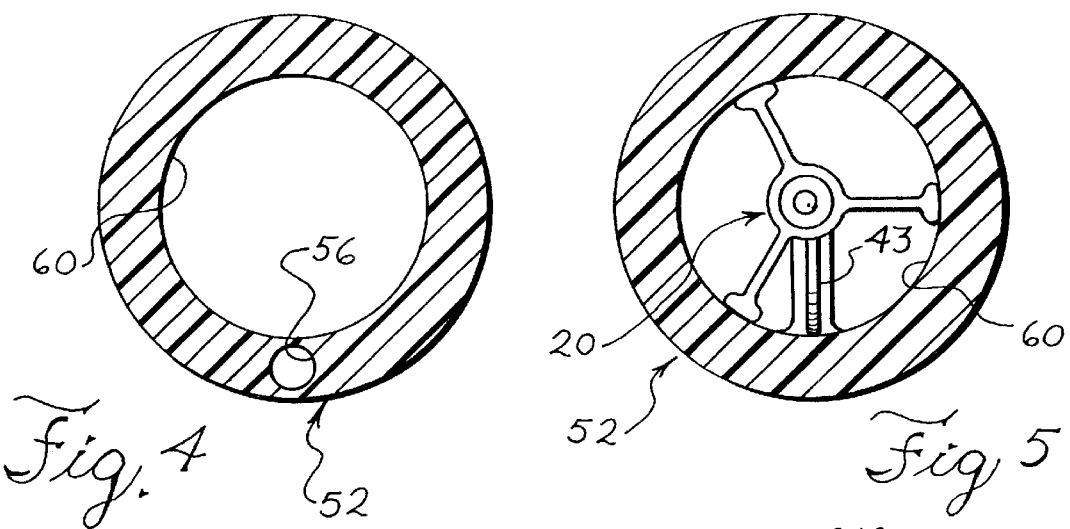
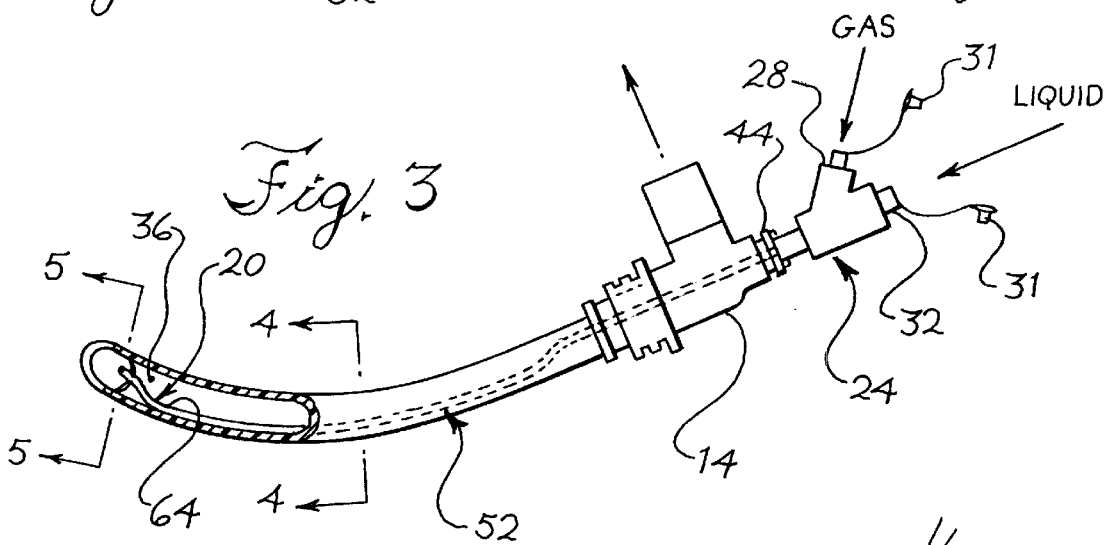
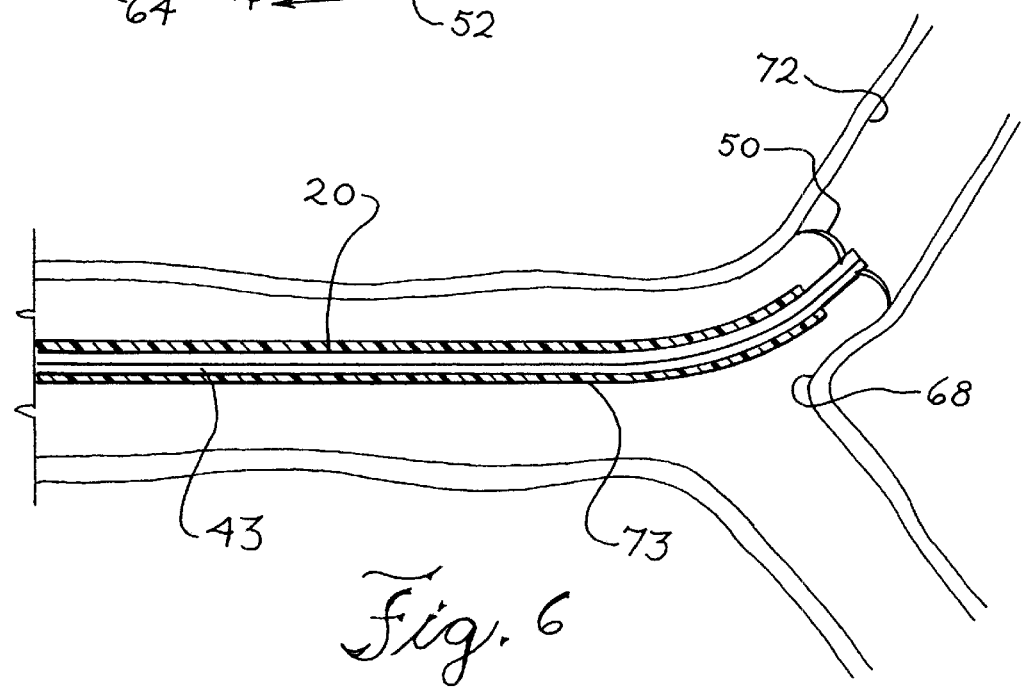

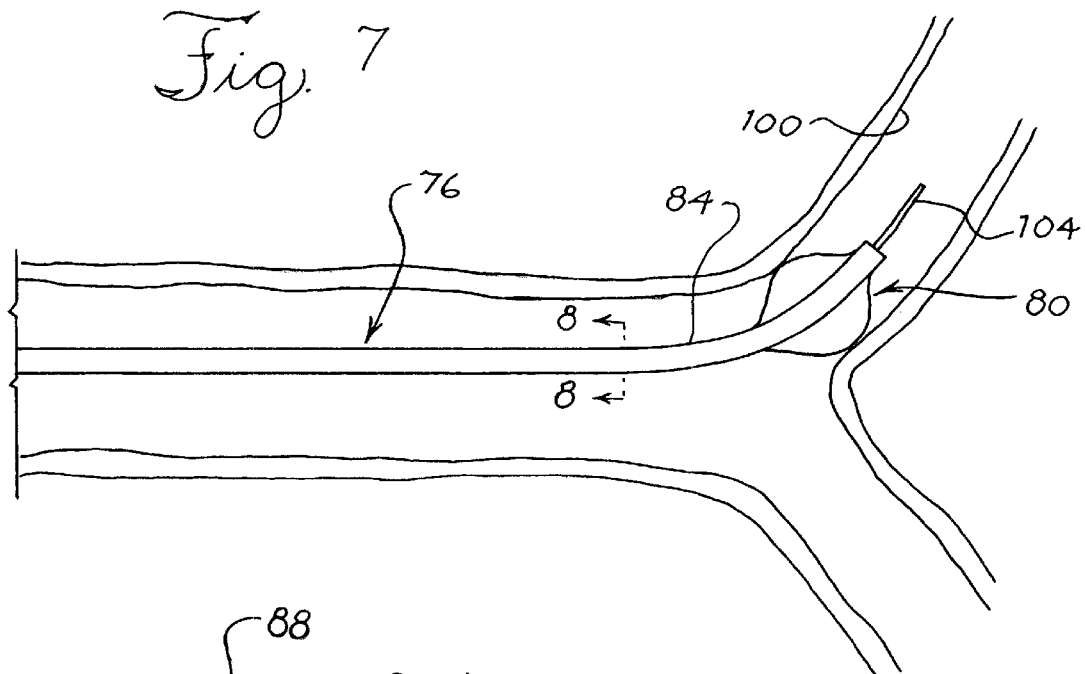
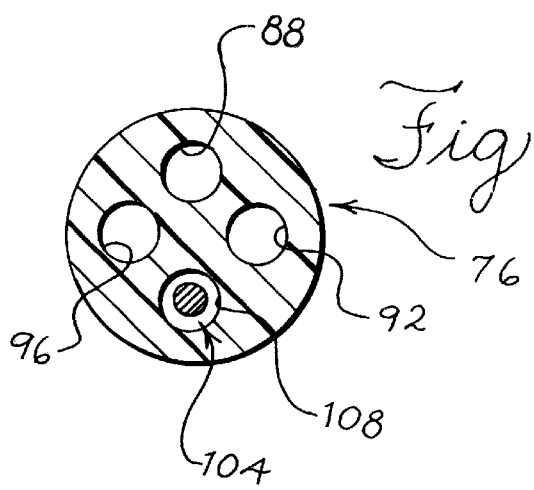
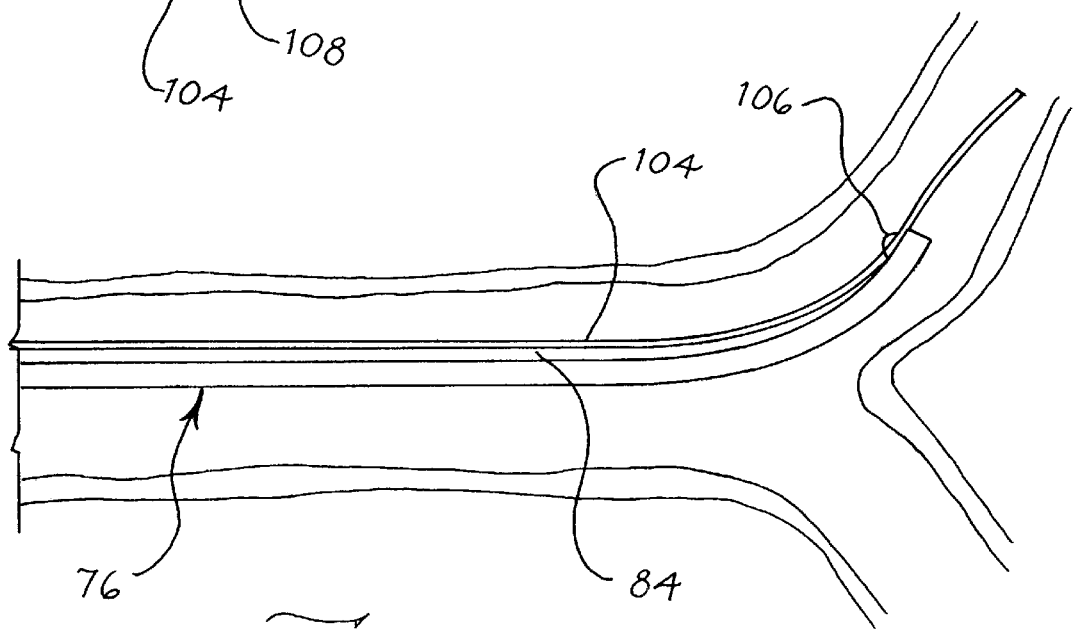

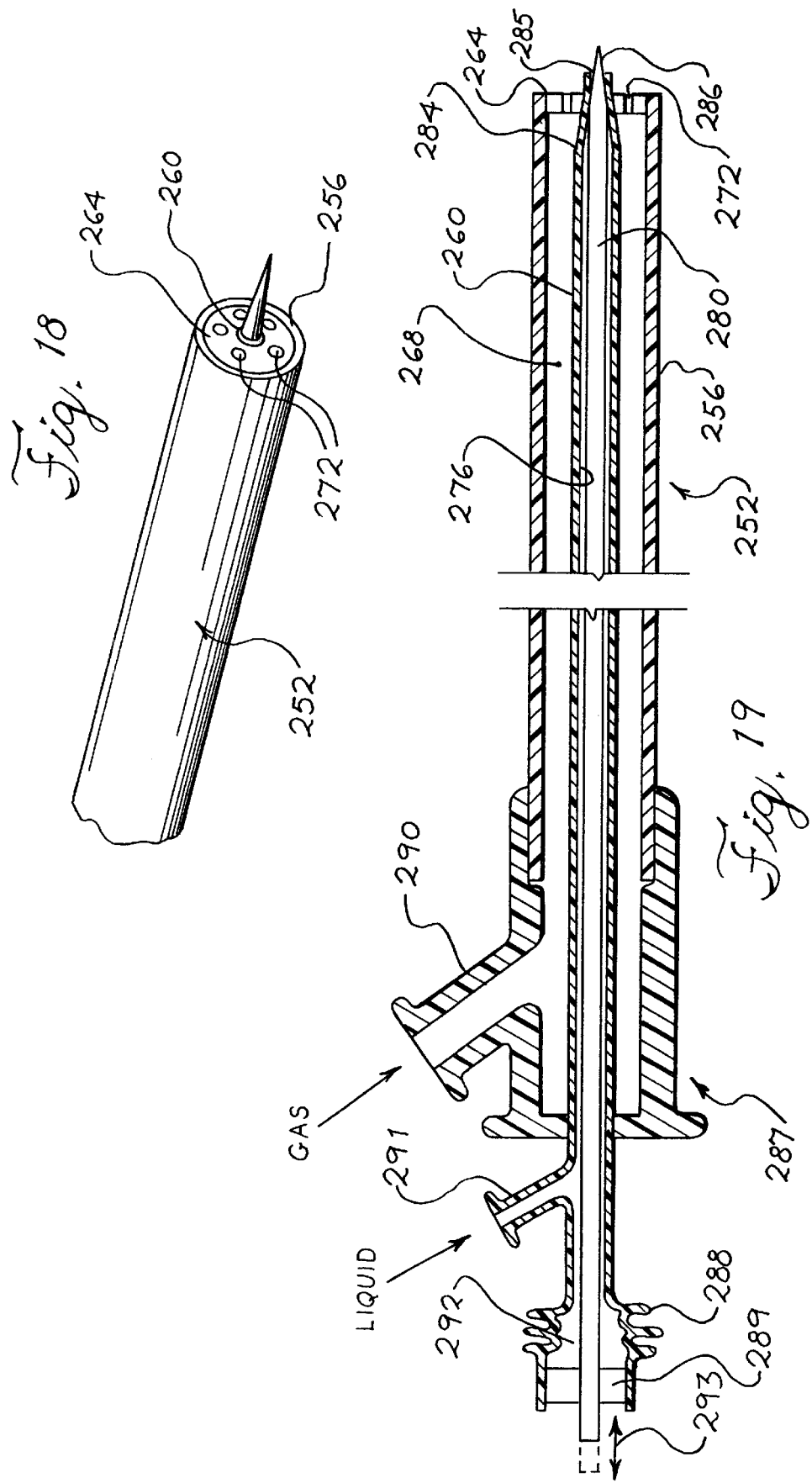

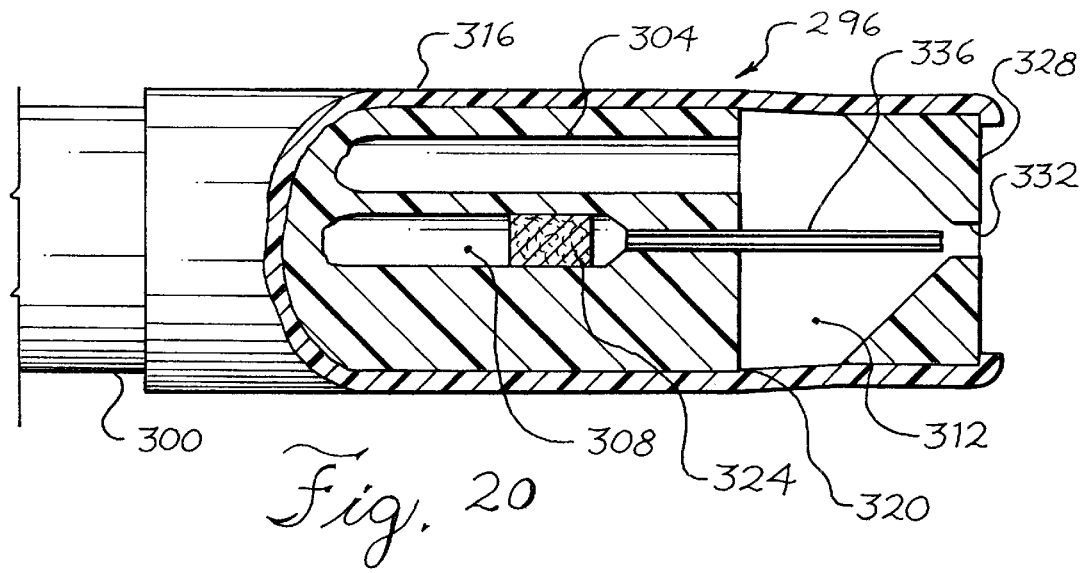
Fig. 20
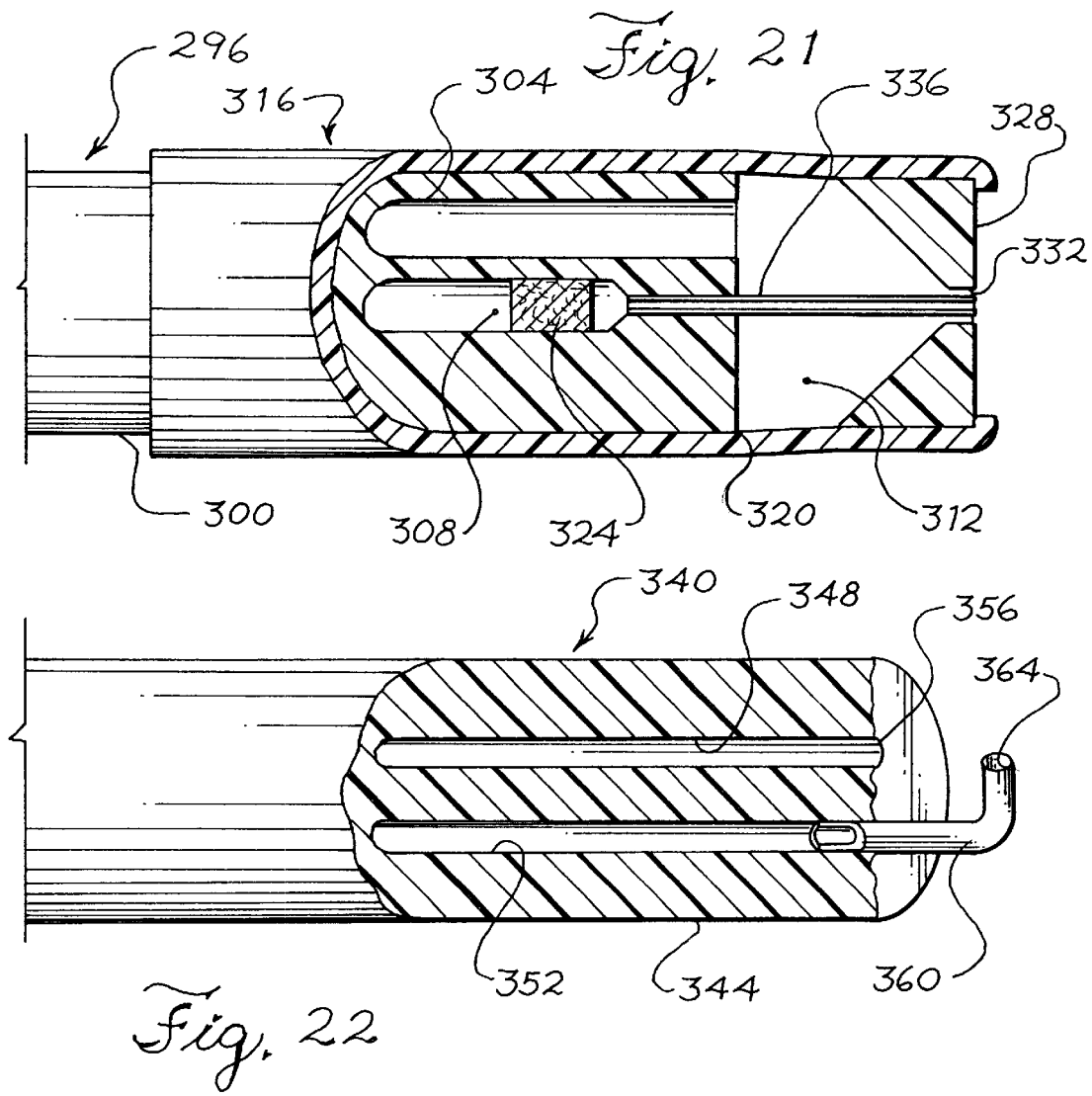
Fig. 21
Fig. 22

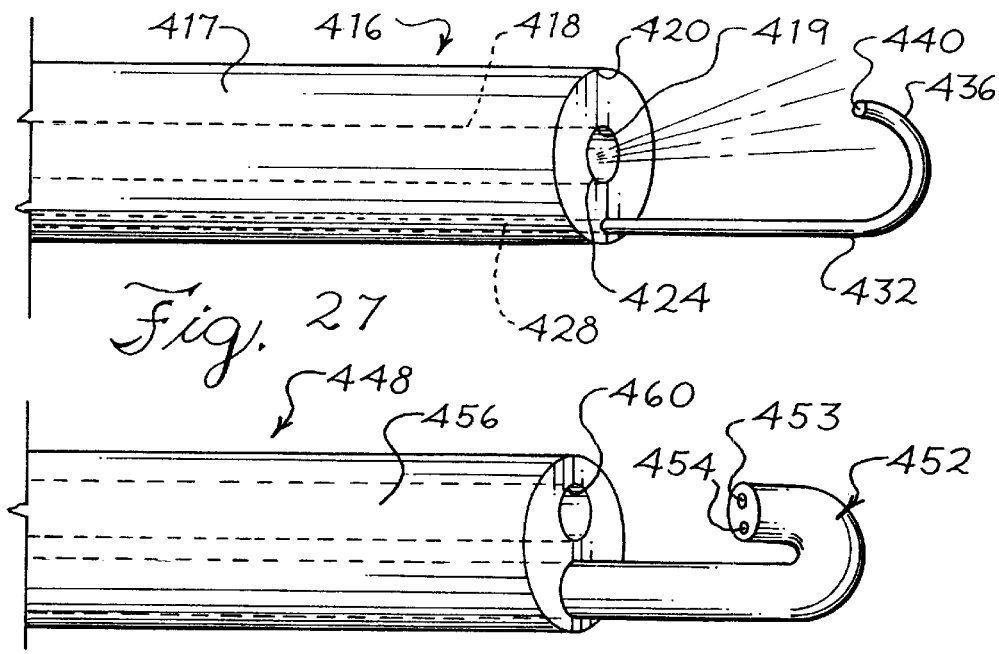
Fig. 27
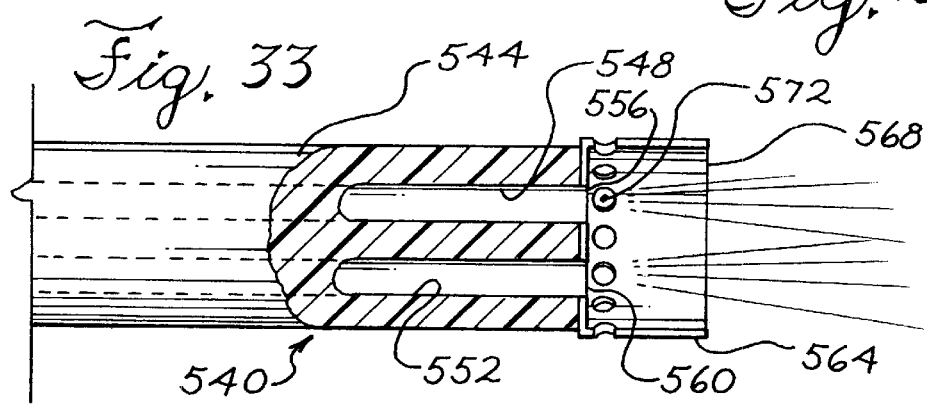
Fig. 28
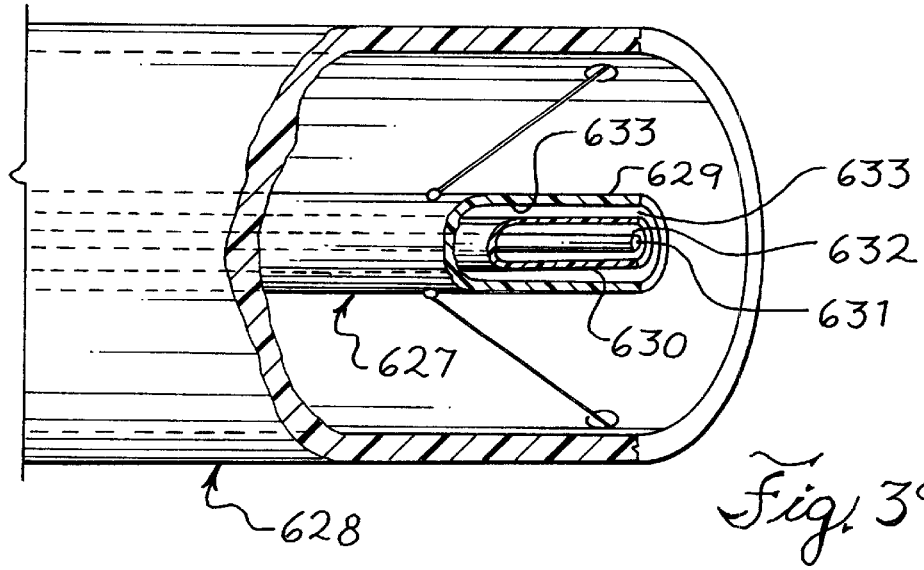
Fig. 33
Fig. 39

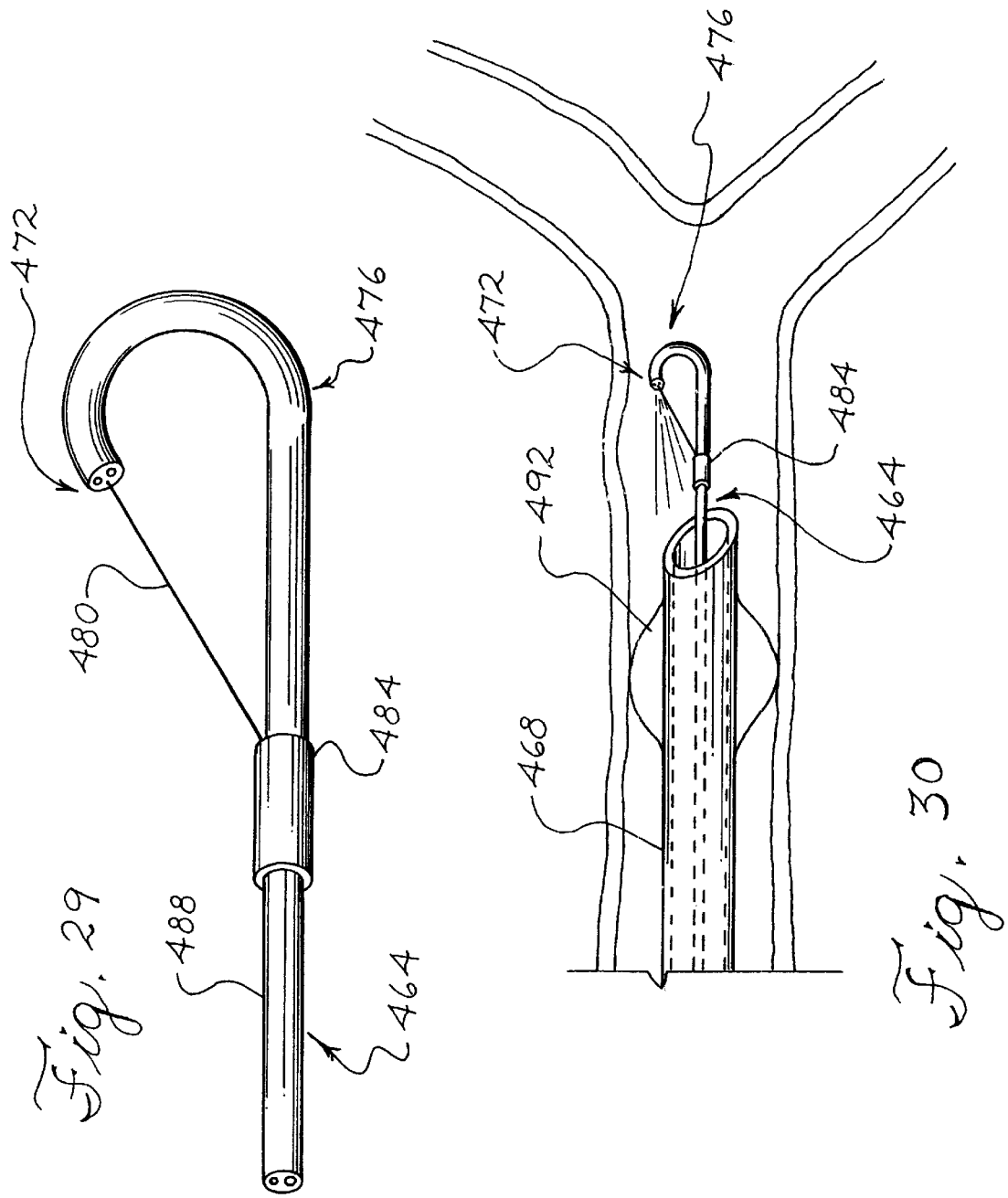

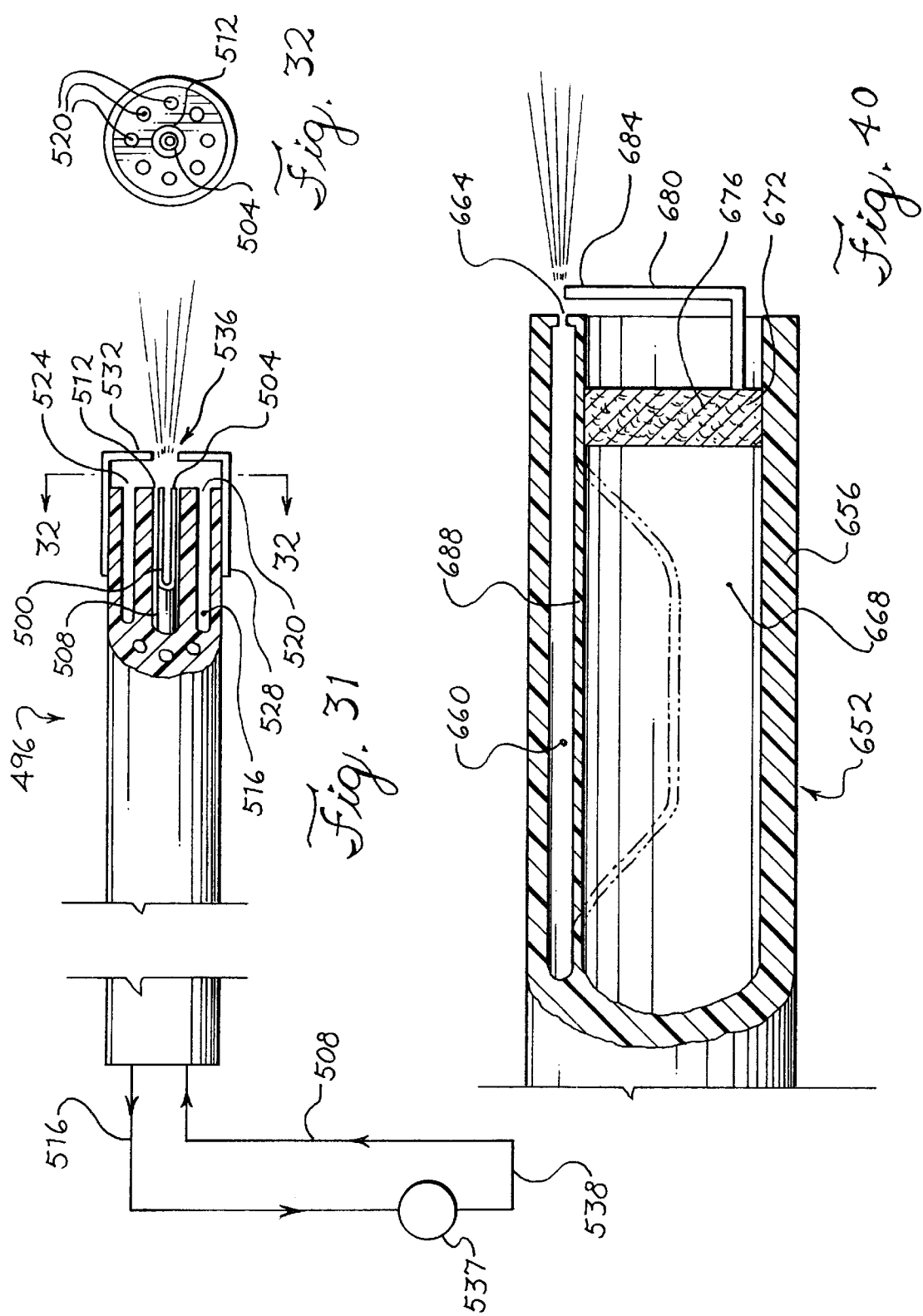

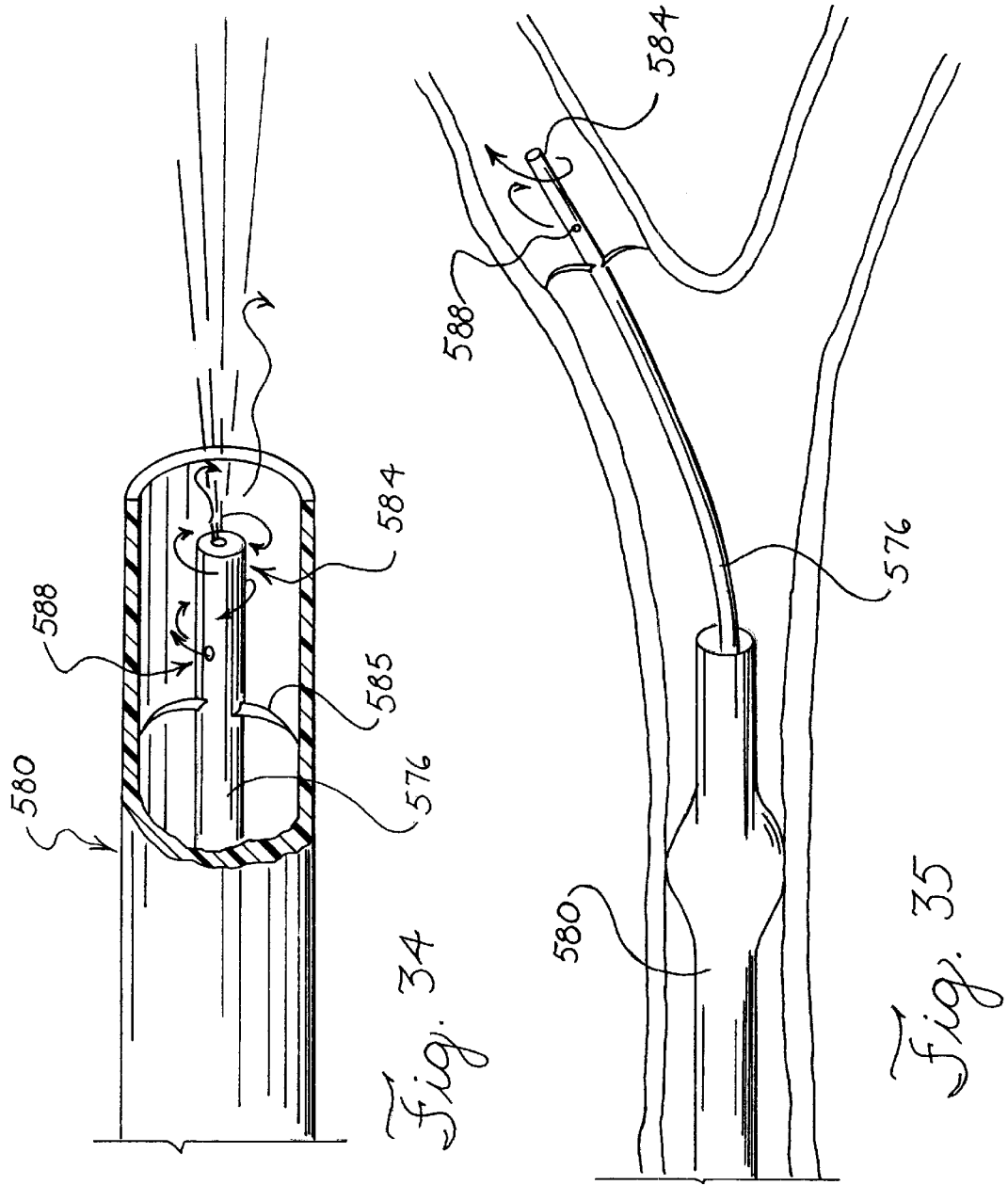

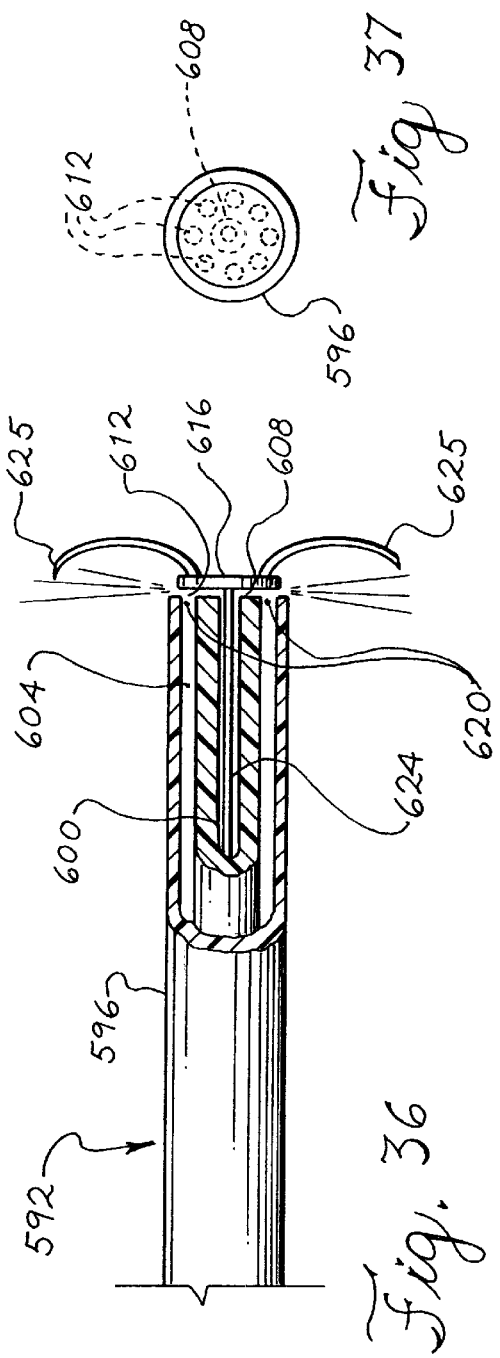

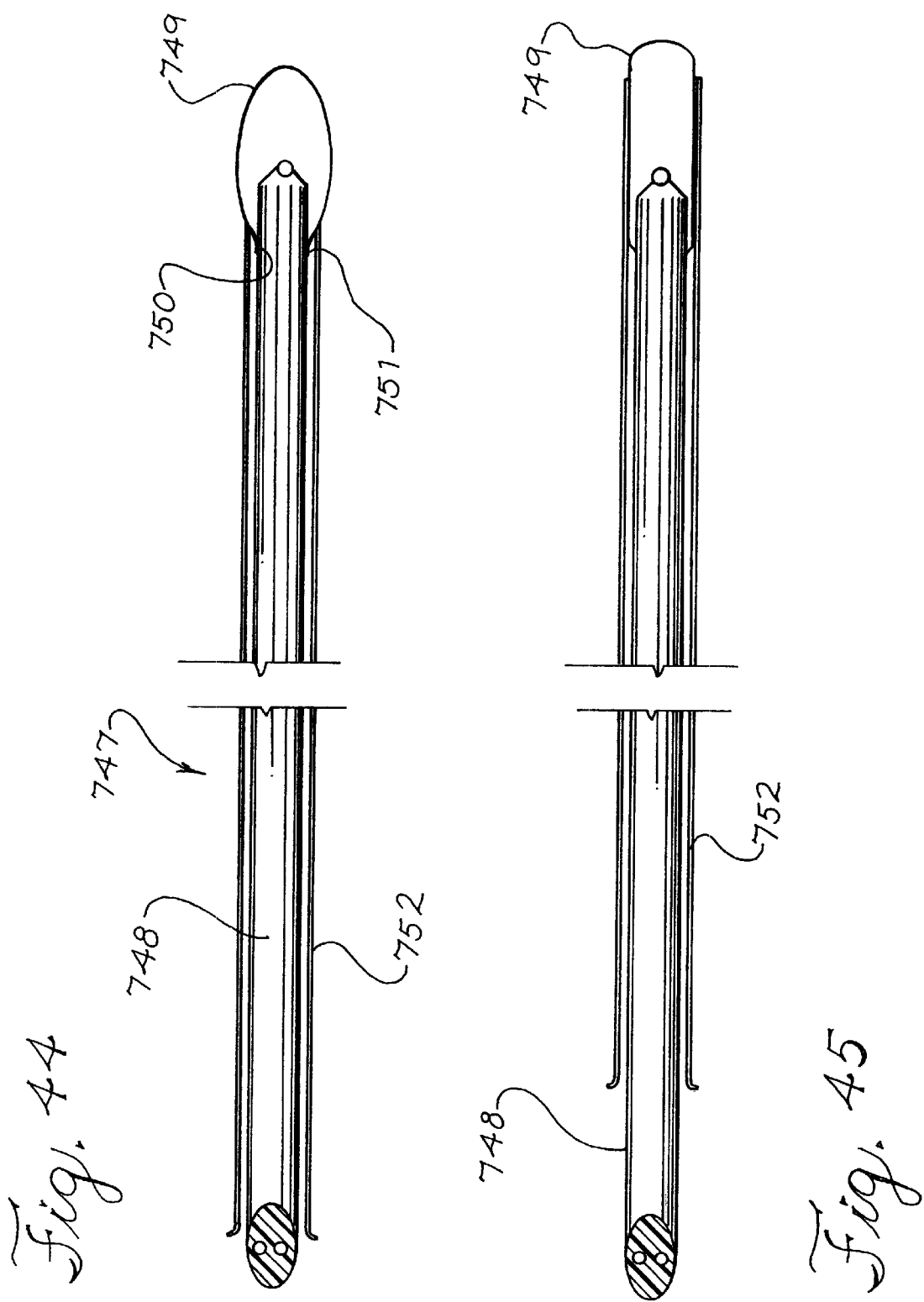

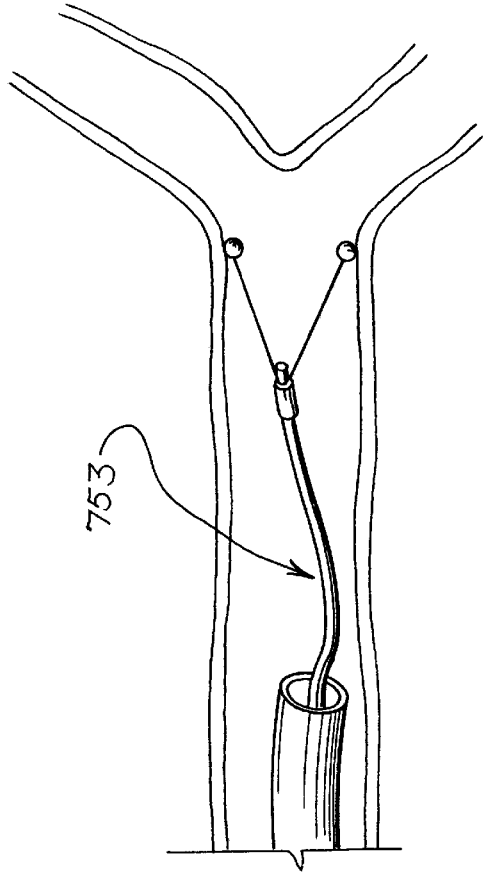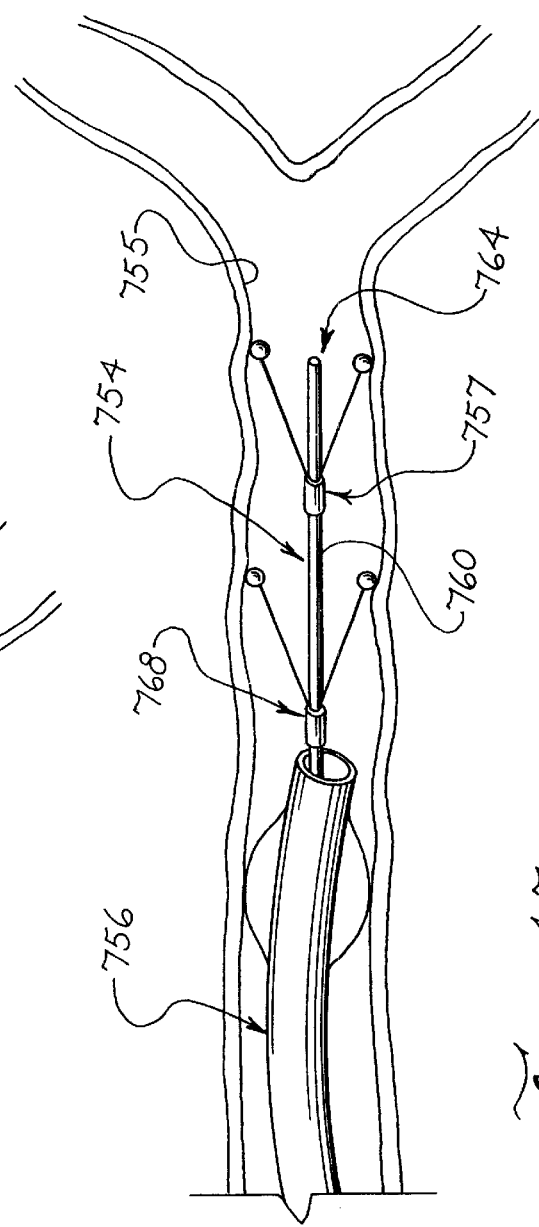

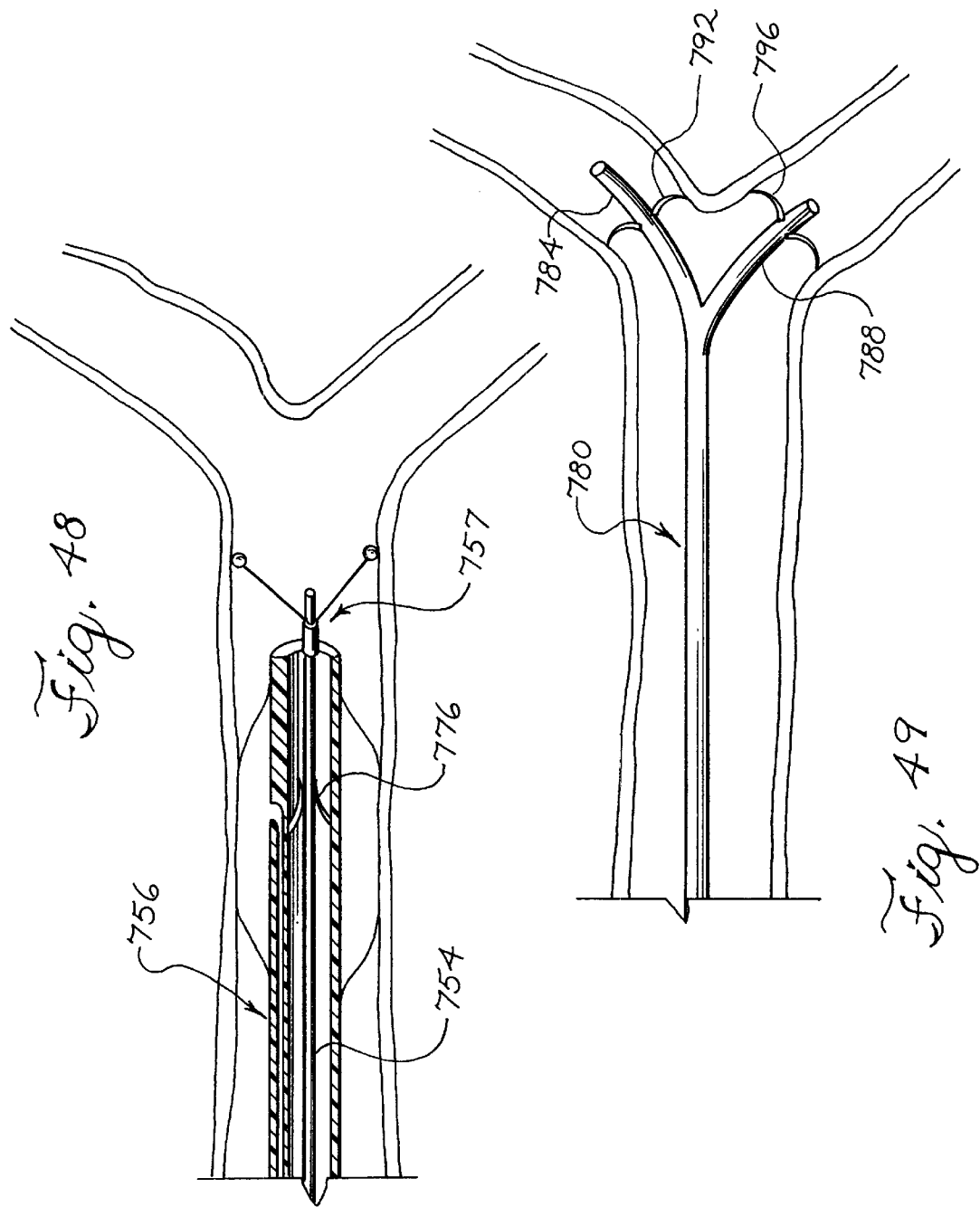

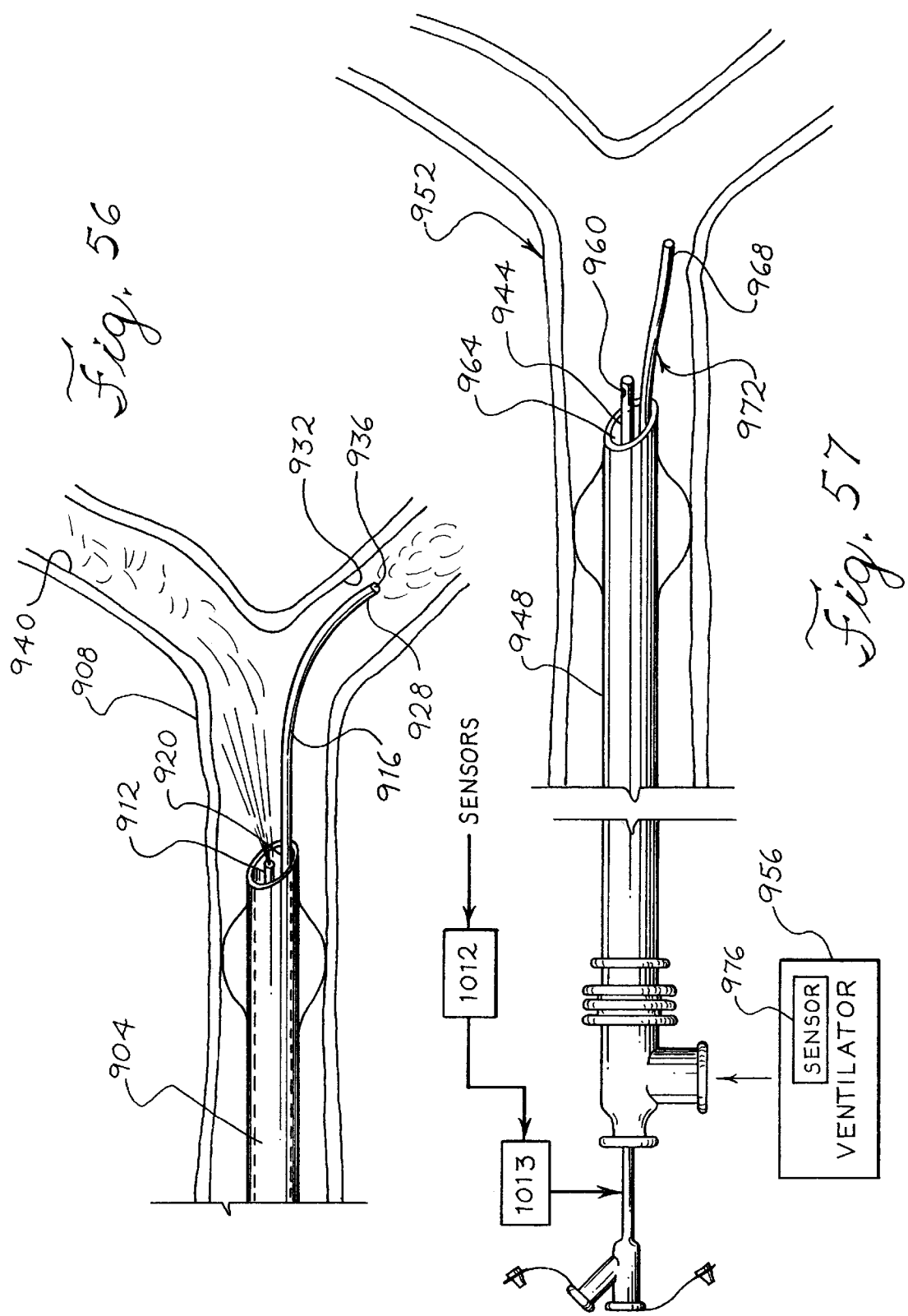

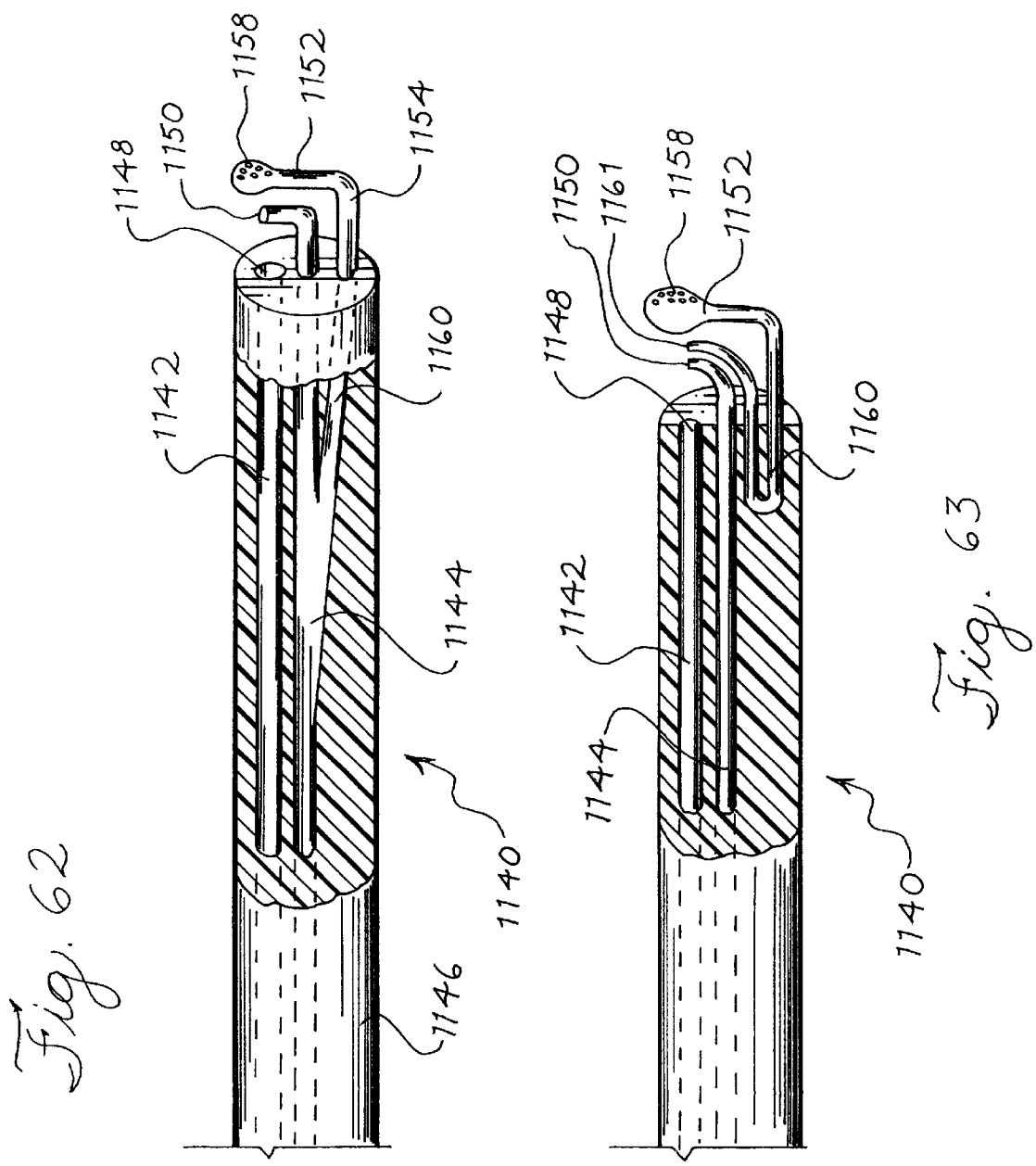

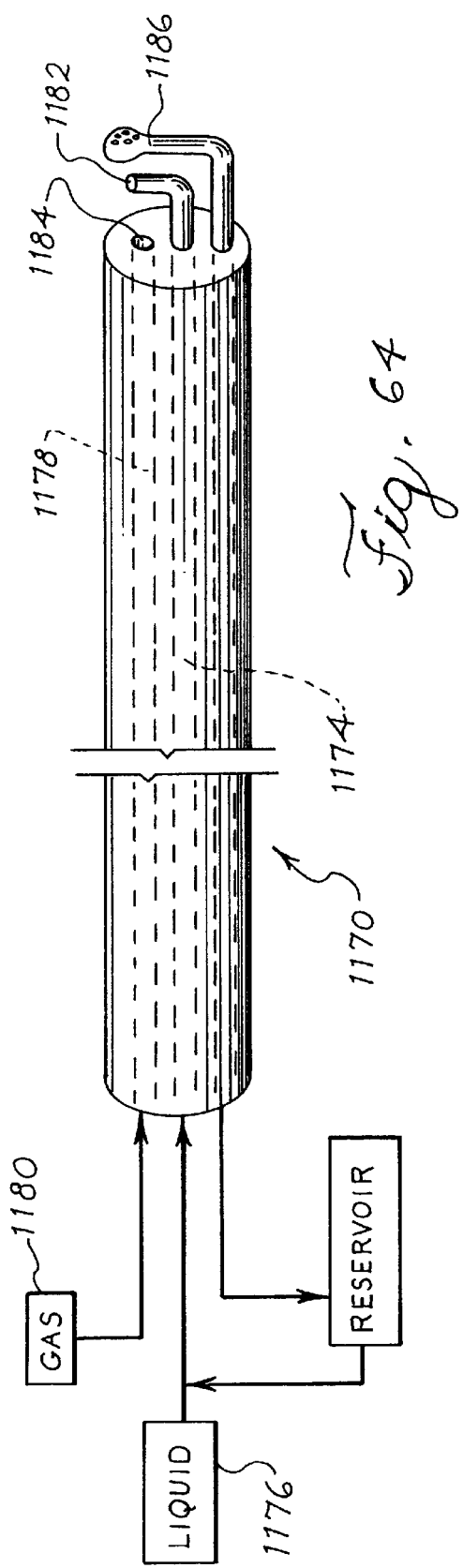
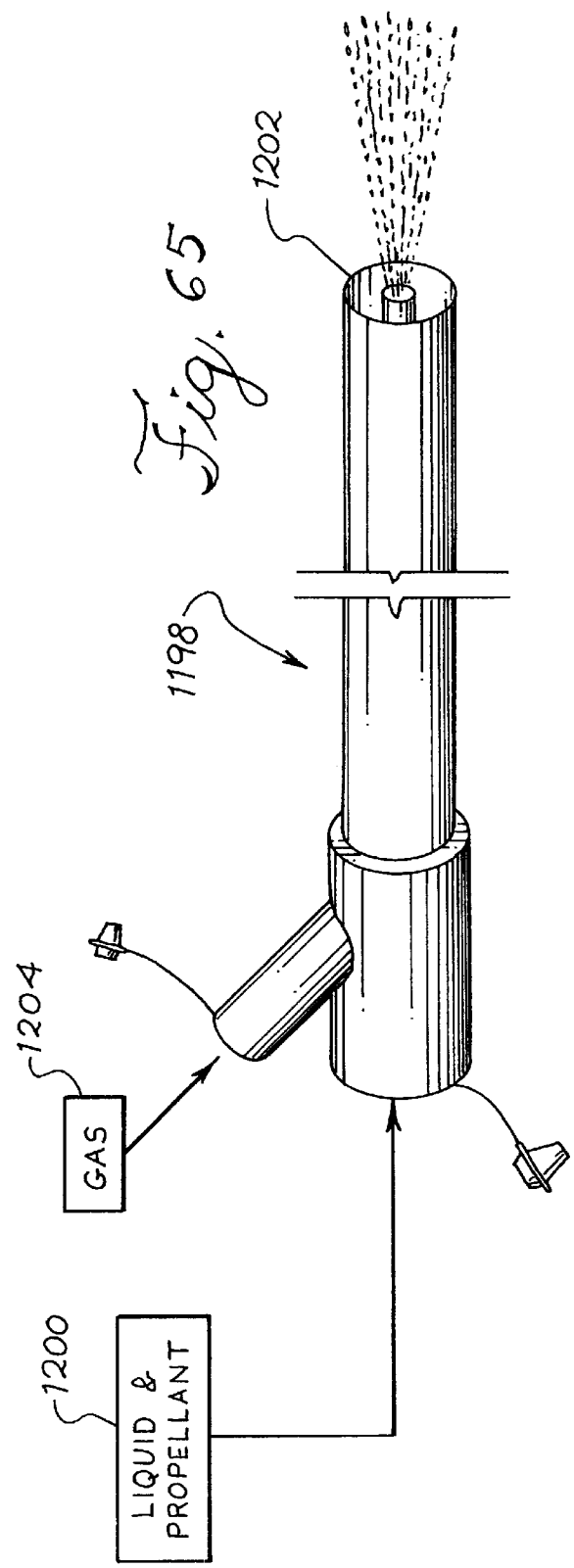

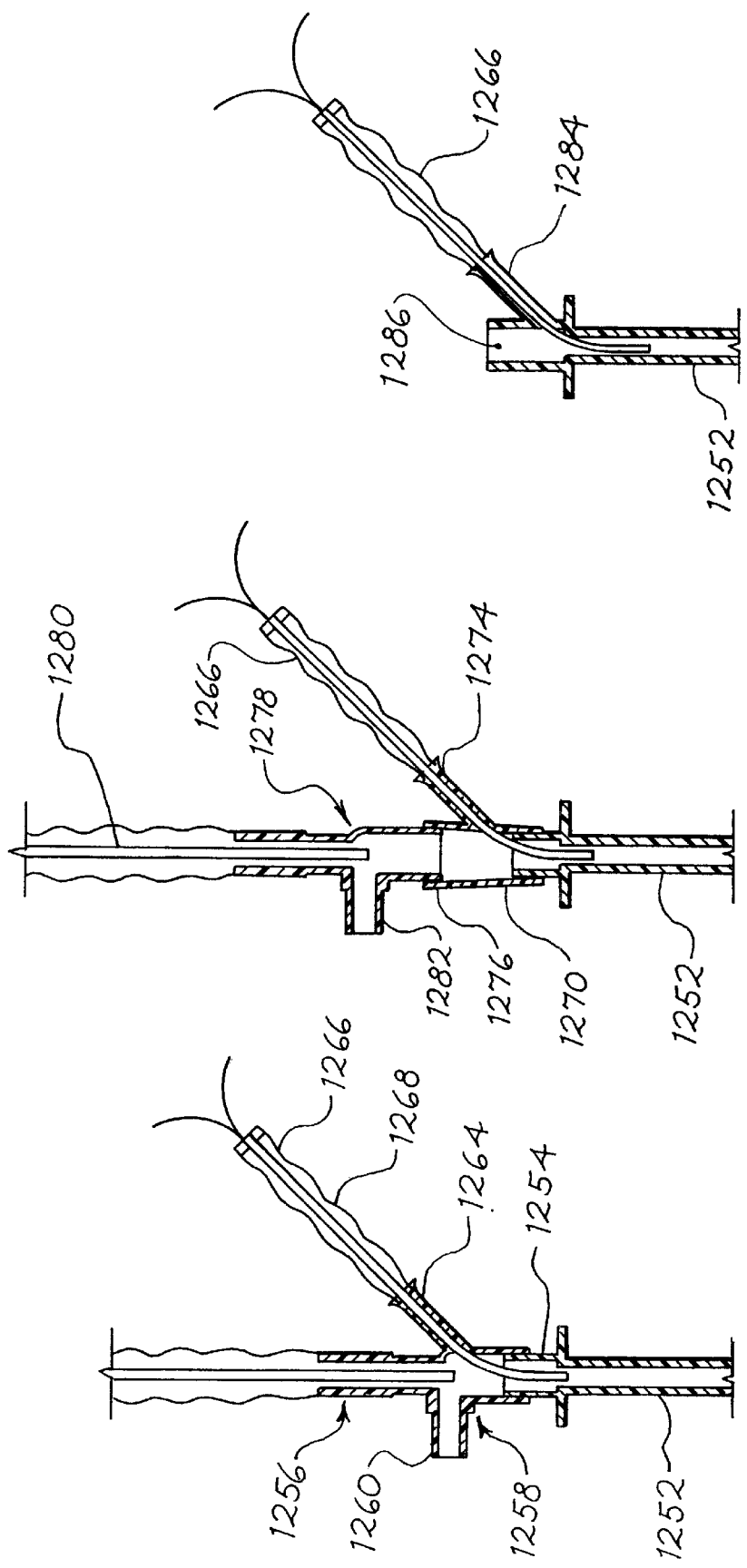

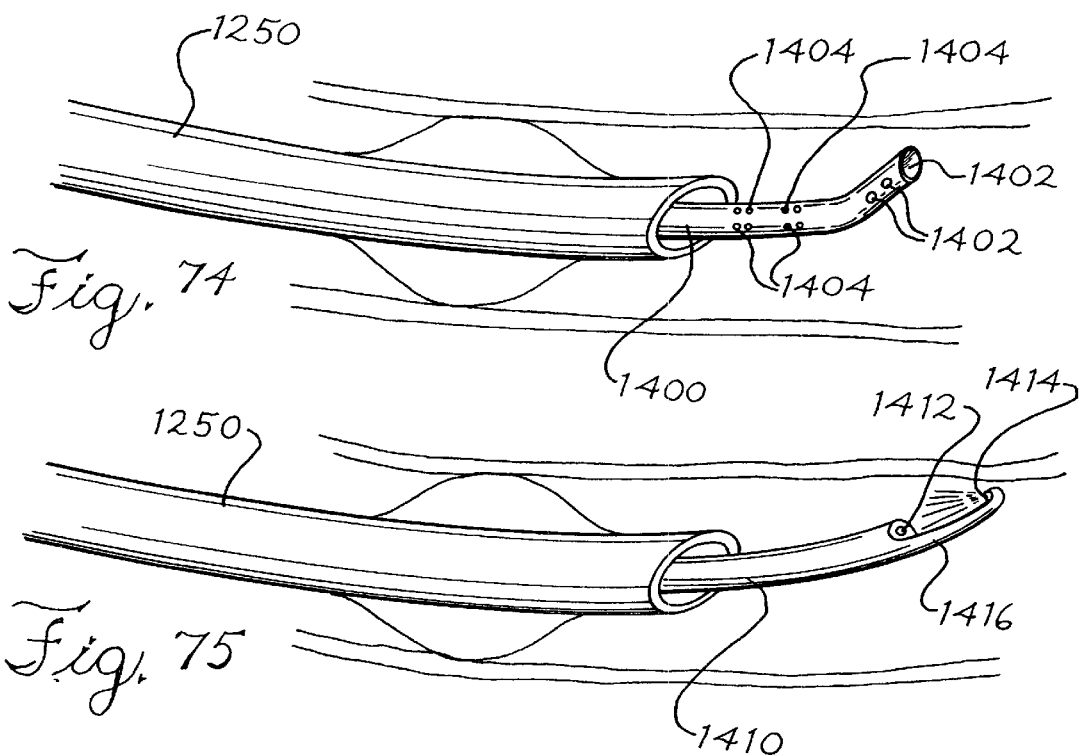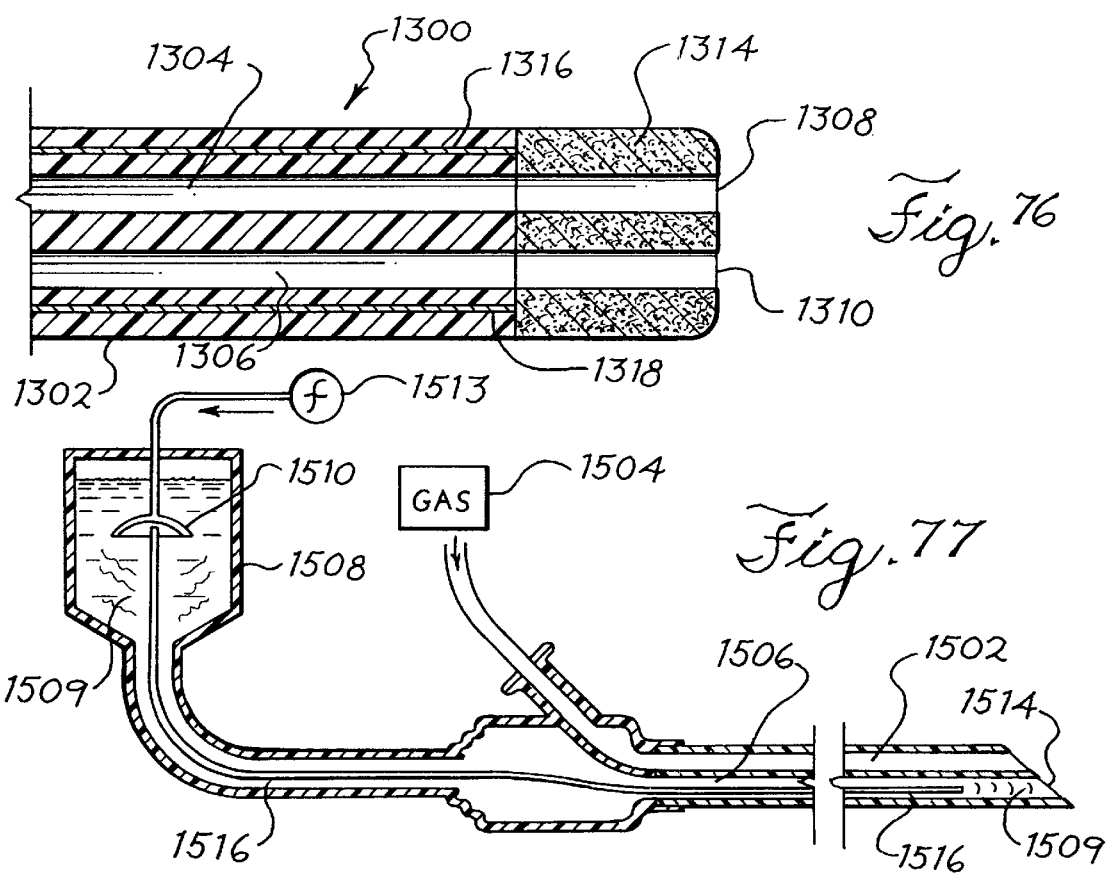

NEBULIZING CATHETER SYSTEM AND METHOD OF USE AND MANUFACTURE

REFERENCE TO RELATED APPLICATIONS

This is a continuation of U.S. patent application Ser. No. 08/787,813 filed Jan. 23, 1997, now U.S. Pat. No. 5,964,223 and a continuation claiming priority to U.S. patent application Ser. No. 08/261,866, filed on Jun. 17, 1994, now abandoned which applications are hereby incorporated by reference.

The present application incorporates by reference the copending application entitled "IMPROVED CATHETER SYSTEM FOR DELIVERY OF AEROSOLIZED MEDICINE FOR USE WITH PRESSURIZED PROPELLANT CANISTER" filed by the same inventor of the present application and on even date herewith.

BACKGROUND OF THE INVENTION

The present invention relates to aerosol delivery of medication to the lungs and more particularly, the present invention relates to delivery systems for application of nebulized medication to the lungs with improved delivery rates, efficiencies, and control.

Many types of medication can be administered to a patient via the respiratory tract. Medication delivered through the respiratory tract may be carried with a patient's inhalation breath as airborne particles (e.g. an aerosol or nebula) into the lungs where the medication can cross through the thin membrane of the alveoli and enter the patient's bloodstream. Delivery of medication via the respiratory tract may be preferred in many circumstances because medication delivered this way enters the bloodstream very rapidly. Delivery of medication to the lungs may also be preferred when the medication is used in a treatment of a disease or condition affecting the lungs in order to apply or target the medication as close as physically possible to the diseased area.

Although delivery of medication via the respiratory tract has been used for many years, there are difficulties associated with prior systems that have limited their use and application. For example, conventional methods have provided for only limited medication delivery rates, efficiency, and control. Conventional methods for aerosol delivery result in a substantial portion of the medicine failing to be delivered to the lungs, and thereby possibly being wasted, or possibly being delivered to other parts of the body, e.g. the trachea.

Aerosols in general are relatively short-lived and can settle out into larger particles or droplets relatively quickly. Aerosols can also impact each other or other objects, settle out as sediment, diffuse, or coalesce. Aerosol particles can also be subject to hydroscopic growth as they travel. Delivery of medicine as airborne particles requires conversion of the medicine, which may be in liquid form, to an aerosol followed relatively quickly by application of the aerosol to the respiratory tract. One such device that has been utilized for this purpose is an inhaler. Inhalers may atomize a liquid to form an aerosol which a person inhales via the mouth or nose. Inhalers typically provide only limited delivery of medication to the lungs since most of the medication is deposited on the linings of the respiratory tract. It is estimated that as little as 10–15% of an aerosol inhaled in this way reaches the alveoli.

Aerosol delivery of a medication to a patient's respiratory tract also may be performed while the patient is intubated, i.e. when an endotracheal tube is positioned in the patient's trachea to assist in breathing. When an endotracheal tube is positioned in a patient, a proximal end of the endotracheal tube may be connected to a mechanical ventilator and the distal end is located in the trachea. An aerosol may be added to the airflow in the ventilator circuit of the endotracheal tube and carried by the patient's inhalation to the lungs. A significant amount of the aerosolized medication may be deposited inside the endotracheal tube and the delivery rate of the medicine to the lungs also remains relatively low and unpredictable.

The low and unpredictable delivery rates of prior aerosol delivery systems have limited the types of medications that are delivered via the respiratory tract. For new medications that are relatively expensive, the amount of wasted medicine may be a significant cost factor in the price of the therapy. Therefore, it would be advantageous to increase the delivery rate or efficiency of a medicine delivered to the lungs.

Another consideration is that some aerosols delivered to the lungs may have adverse side effects, e.g. radioactive tracers used for lung scans. Therefore, it would be advantageous to minimize the overall amount of medication delivered while maintaining the efficacy of the medication by providing the same or a greater amount of the medication to the desired site in the respiratory tract.

Further, some medications may be more effective when delivered in certain particle sizes. Accordingly, an improved aerosol delivery system may provide for improved rates and efficiencies of delivery also taking into account the aerosol particle size.

It may also be important to administer certain medications in specific, controlled dosages. The prior methods of aerosol delivery not only were inefficient, but also did not provide a reliable means to control precisely the dosage being delivered.

It may also be advantageous to be able to target medication to a specific bronchus, or specific groups of bronchia, as desired, while avoiding delivery of medication to other portions of the lungs.

Taking into account these and other considerations, aerosol delivery via the respiratory tract could become an even more widely used and effective means of medication delivery if the delivery rate and efficiency of the delivery could be improved.

SUMMARY OF THE INVENTION

According to an aspect of the present invention, there is provided a method and apparatus for delivering a drug with control and efficiency to a patient via the patient's respiratory system. A nebulization catheter is positioned in the patient's respiratory system so that a distal end of the nebulization catheter is in the respiratory system and a proximal end is outside the body. According to a first aspect, the nebulization catheter may be used in conjunction with an endotracheal tube and preferably is removable from the endotracheal tube. The nebulization catheter conveys medicine in liquid form to the distal end at which location the medicine is nebulized by a pressurized gas or other nebulizing agent. The nebulized medicine is conveyed to the patient's lungs by the patient's respiration which may be assisted by a ventilator. The nebulizing catheter incorporates alternative constructions taking into account anatomical considerations and the properties of the medicine being nebulized to provide delivery of medicine with control and efficiency.

BRIEF DESCRIPTION OF THE DRAWINGS

FIG. 1 shows an exploded view of a first embodiment of the present invention.

FIG. 2 shows an assembled view of the embodiment of FIG. 1.

FIG. 2A is a sectional view of the nebulization catheter of FIGS. 1 and 2.

FIG. 3 is a plan view of an alternative embodiment of the endotracheal tube shown in FIGS. 1 and 2.

FIG. 4 is a cross sectional view taken along the line a–a' of the alternative embodiment of the endotracheal tube shown in FIG. 3 without the nebulizing catheter in place.

FIG. 5 is a cross sectional view taken along the line b–b' of the alternative embodiment of the endotracheal tube shown in FIG. 3 with the nebulizing catheter in place.

FIG. 6 is a plan view of an embodiment of the nebulizing catheter of FIGS. 1 and 2 shown in place in the trachea of a patient who is not intubated.

FIG. 7 is a view similar to that of FIG. 6 showing an alternative embodiment of the nebulization catheter.

FIG. 8 is a cross section taken along lines a–a' of the nebulization catheter of FIG. 7.

FIG. 9 is a view similar to that of FIG. 7 showing an alternative embodiment of the nebulizing catheter shown in FIG. 7.

FIG. 18 is a perspective view of a distal end of an alternative embodiment of the nebulization catheter shown in FIG. 1.

FIG. 19 is a sectional view of the distal end of the embodiment of the nebulization catheter shown in FIG. 18.

FIG. 20 is a sectional view of a distal end of an alternative embodiment of the nebulization catheter shown in FIG. 1.

FIG. 21 is a sectional view similar to that of FIG. 20 showing an alternative embodiment of the nebulization catheter shown in FIG. 20.

FIG. 22 is a perspective view partially in section of a distal end of an alternative embodiment of the nebulization catheter shown in FIG. 1.

FIG. 27 is a perspective view of alternative embodiments of the nebulization catheter and endotracheal tube shown in FIG. 1.

FIG. 28 is a perspective view of alternative embodiments of the nebulization catheter and endotracheal tube shown in FIG. 27.

FIG. 29 is a perspective view of an alternative embodiment of the nebulization catheter shown in FIGS. 27 and 28.

FIG. 30 is a perspective view of the embodiment of the nebulization catheter shown in FIG. 29 shown with an endotracheal tube in a patient's trachea.

FIG. 31 is sectional view of a distal end and a diagrammatic view of a proximal end of an alternative embodiment of the nebulization catheter shown in FIG. 1.

FIG. 32 is a cross section view of the embodiment of the nebulization catheter shown in FIG. 31 taken along the line a–a'.

FIG. 33 is sectional view of a distal end of an alternative embodiment of the nebulization catheter shown in FIG. 1.

FIG. 34 is sectional perspective view of a distal end of an alternative embodiment of the nebulization catheter and endotracheal tube shown in FIG. 2.

FIG. 35 is sectional view of a distal end of an alternative embodiment of the nebulization catheter shown in FIG. 1.

FIG. 37 is a cross section view of the embodiment of the nebulization catheter shown in FIG. 36 taken along the line a–a'.

FIG. 38 is a perspective view of a distal end of an alternative embodiment of the nebulization catheter shown in FIGS. 36 and 37.

FIG. 39 is a perspective view of alternative embodiments of the nebulization catheter and endotracheal tube shown in FIGS. 37 and 38.

FIG. 40 is sectional perspective view of a distal end of an alternative embodiment of the nebulization catheter shown in FIG. 1.

FIG. 44 is a side view of an another embodiment of the nebulization catheter of FIG. 1 showing yet another alternative centering device.

FIG. 45 is a side view of the embodiment of FIG. 44 shown in another stage of operation.

FIG. 46 is a side view of a distal end of a nebulization catheter positioned in a patient's trachea illustrating an undesirable condition.

FIG. 47 is a perspective view similar to that of FIG. 40 of alternative embodiments of the nebulization catheter and endotracheal addressing the condition shown in FIG. 46.

FIG. 48 shows an alternative embodiment of the nebulizing catheter and endotracheal tube of FIG. 47 positioned in a patient's trachea.

FIG. 49 shows an alternative embodiment of the nebulizing catheter of FIG. 6.

FIG. 56 is a perspective view of an alternative embodiment of the present invention illustrating an alternative method of use.

FIG. 57 is a perspective view illustrating an entire nebulization catheter system including sensors.

FIG. 62 is a sectional view of another embodiment of the present invention that incorporates a baffle to generate a secondary aerosol.

FIG. 63 is a sectional view of yet another embodiment of the present invention that incorporates a baffle to generate a secondary aerosol.

Figure 10:
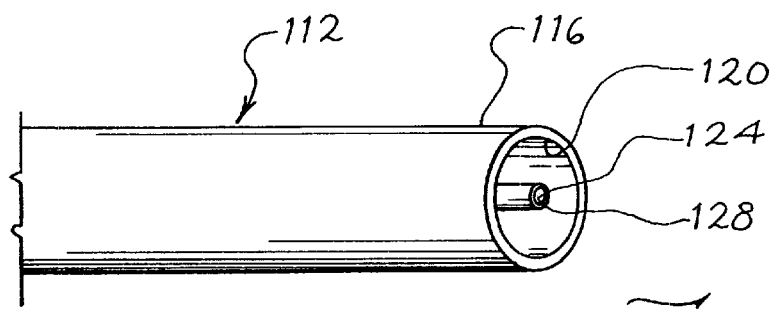
FIG. 10 is a perspective view of a distal end of an alternative embodiment of the nebulization catheter shown in FIG. 1.

FIG. 64 is a sectional view of still another embodiment of the present invention that incorporates a baffle to generate a secondary aerosol.

FIG. 65 is a diagram illustrating an embodiment of the present invention that incorporates a pressurized drug/propellant mixture canister.

FIG. 66 is a side view of an embodiment of a nebulizing catheter incorporated into of a suction catheter.

FIG. 67 is a detailed sectional view of the tip portion of the suction catheter—nebulizing catheter embodiment of FIG. 66.

FIG. 68 is a perspective view of the embodiment of FIG. 66 positioned in an endotracheal tube in a patient's respiratory system.

FIG. 69 is cross sectional view of the embodiment of FIG. 66 taken along lines a–a'.

FIG. 70 is a perspective view similar to FIG. 68 showing the suction catheter advanced during an further stage of operation.

FIG. 71 is a side view of a proximal end of an endotracheal tube illustrating an arrangement of receiving a suction catheter and a nebulization catheter into the endotracheal tube.

FIG. 72 is an alternative embodiment of the arrangement shown in FIG. 71.

FIG. 73 is another alternative embodiment of the arrangement shown in FIG. 71.

FIG. 74 is another embodiment of a suction catheter incorporating aerosol delivery by nebulization.

FIG. 75 is still another embodiment of a suction catheter incorporating aerosol delivery by nebulization.

FIG. 76 is a sectional view of a distal end of an embodiment of a nebulizing catheter also incorporating a vibrating tip.

FIG. 77 is a sectional view of another embodiment of the nebulizing catheter incorporating micropulsation of the liquid supply.

DETAILED DESCRIPTION OF THE PRESENTLY PREFERRED EMBODIMENTS

The present invention provides for the controlled and efficient delivery of an aerosolized medication to the lungs of a patient by nebulization of a medication at a distal end of a catheter positioned in the respiratory tract. Throughout this specification and these claims, the nebulization catheter is described as used for the delivery of medicine or medication. It is intended that the terms "medication", "medicine", and "drug" should be understood to include other agents that can be delivered to the lungs for diagnostic or therapeutic purposes, such as tracers, or for humidification.

I. Nebulizing Catheter—Basic Configuration

Referring to FIGS. 1 and 2, there is depicted a first embodiment of the present invention. FIGS. 1 and 2 show an endotracheal tube 10 which may be a conventional endotracheal tube. The endotracheal tube 10 may have an inflatable cuff 12 located close to its distal end to facilitate positioning the tube 10 in the patient's trachea, or alternatively the endotracheal tube 10 may be of a type without an inflatable cuff. The inflatable cuff 12 is connected via a separate inflation lumen in the endotracheal tube 10 to a proximal fitting 13 for connection to a source of inflating gas (not shown). The endotracheal tube 10 has a proximal end connected to a manifold fitting 14. The fitting 14 has a port 15 suitably adapted for connection to a ventilator circuit (not shown). The fitting 14 also includes another port 16 that permits the introduction of a separate catheter into the endotracheal tube from the proximal end. The fitting 14 may be similar in construction to the elbow fitting described in U.S. Pat. No. 5,078,131 (Foley), the entire disclosure of which is incorporated herein by reference. In FIG. 1, a nebulizing catheter 20 is located in a position ready to be inserted into a ventilation lumen 22 of the endotracheal tube 10 via the proximal fitting 14. In FIG. 2, the nebulizing catheter 20 is positioned fully in the endotracheal tube 10 with a proximal end extending out of the port 16 of the proximal fitting 14.

At a proximal end of the nebulizing catheter 20 is a manifold 24. The manifold 24 includes at least a gas port 28 and a liquid (medicine) port 32. These ports 28 and 32 may include conventional attaching means, such as luer lock type fittings. In addition, these ports 28 and 32 may also include closure caps 31 that may be used to close the ports when not in use and may be popped open when connection to a gas source or a liquid source is desired. Optionally, the manifold 24 may also include a filter located in-line with either the gas port 28 or the liquid port 32 or both ports to prevent lumen blockages by particulate matter. The nebulization catheter 20 includes at least two separate lumens (as shown in FIG. 2A). A first lumen 33 is used for conveyance of a liquid medicine and communicates with the port 32 on the manifold 24. The other lumen 34 is used for conveyance of a pressurized gas and communicates with the port 28 on the manifold 24. The liquid lumen 33 communicates with a distal liquid orifice 35 and the gas lumen 34 communicates with a distal gas orifice 36 near a distal end 37 of the nebulization catheter 20. The distal opening 36 of the pressurized gas lumen 34 directs pressurized gas across the distal liquid lumen opening 35 thereby nebulizing the liquid medication so that it can be delivered to the patient's lungs. The distal liquid orifice 35 may be open or may be provided with a porous material plug or a sponge-like or felt-like material plug which may extend slightly from the distal orifice and that allows liquid to flow from the orifice yet reduces the likelihood of liquid drooling from the tip.

The length of the nebulization catheter 20 should be sufficient so that the distal end 37 can be located in the desired location in the respiratory system while the proximal end (i.e., including the manifold 24) is accessible to the physician or other medical personnel for connection to suitable gas and liquid supplies external of the patient's body. Accordingly, the length of the nebulization catheter is dependant upon the size of the patient in which it is being used. A shorter nebulization catheter may be preferred in smaller patients, such as infants or children, and a longer nebulization catheter may be needed for adults. For example, a nebulization catheter suitable for adults may have a length of approximately 45 cm. In one embodiment, approximately 30 cm of the nebulizing catheter 20 is in the endotracheal tube 10. The nebulization catheter may be introduced into the respiratory system through a patient's mouth or via a tracheostomy tube or through the nasal passages. The nebulization catheter may also be used to deliver an aerosol to a patient's nasal passages in which case the length may be correspondingly shorter.

As explained in more detail below, the generation of an aerosol plume with the desired geometry, particle size, velocity, etc., requires that the distal gas and liquid orifices have small dimensions. Also as explained below, the distal gas orifice 36 and the distal liquid orifice 35 should be in close proximity to each other in order to produce an aerosol with the desired characteristics and efficiency. Further, in order to provide the desired medicine delivery rates and to operate with reasonably available pressure sources, the liquid and gas lumens in the nebulizing catheter should be as large as possible, consistent with anatomical requirements. Accordingly, the nebulization catheter 20 has a multiple stage construction with a larger shaft size and larger lumens in a main shaft section and a smaller shaft size and smaller lumens in a distal shaft section.

As shown in FIG. 2A, the nebulizing catheter 20 is composed of a shaft 38 having a main section 39 and a distal section 40. In the main shaft section 39 of the nebulization catheter, the liquid and gas lumens 33 and 34 have a larger size than in the distal shaft section 40. For example, in the main shaft section 39, the liquid and gas lumens each may have an I.D. of approximately 0.010 to 0.030 inches. At a most proximal end where the main shaft section 39 connects to the manifold 24, the lumens may be even larger. In the distal shaft section 40, the liquid and gas lumens taper to a much smaller I.D. with the liquid lumen approximately 0.002 to 0.008 inches or even smaller and the gas lumen 0.002 to 0.020 inches. In a preferred embodiment, the liquid and gas orifices 35 and 36 are less than 0.125 inches apart, and more preferably less than 0.030 inches apart, and in a most preferred embodiment less than 0.001 inches apart. In a nebulizing catheter having an overall length of 45 cm, the main shaft section 39 may be approximately 25 cm and the distal shaft section 40 may be approximately 20 cm. Also, although the liquid and gas lumens are shown to be side by side in FIG. 2A, they may also be constructed to have an coaxial or other arrangement. Further, although the main shaft section 39 is shown to be of a uniform diameter and profile, alternatively it may also have a tapered diameter and profile such that the entire shaft 38 is tapered along its length.

In a first preferred embodiment of the invention, as shown in FIGS. 1 and 2, the nebulizing catheter 20 is removable, and replaceable with respect to the endotracheal tube 10. This provides several significant advantages. First, the nebulizing catheter 20 may be specifically adapted and chosen to have the desired operating characteristics suitable for delivery of the particular medication being administered to the patient. In addition, the fact that the nebulizing tube 20 is removable and replaceable provides versatility and flexibility regarding the therapy and dosage regime that can be chosen by the physician. For example, a decision by the physician whether to deliver a medication to the respiratory tract, and the selection of the type and dosage of the medication to be delivered, need not be made by the physician until after the endotracheal tube is already in place in the patient. When the physician determines the proper type of medication to the delivered to the patient via the respiratory tract, the appropriate nebulization catheter can be selected and inserted into the endotracheal tube. Further, the nebulizing catheter 20 can be removed after it is used and therefore it is not necessary for the nebulization catheter to be left in the patient and occupy space in the patient's respiratory tract or in the endotracheal tube 10 when it is no longer needed. In addition, the decision regarding the proper type of medication can be revisited again at any time after the endotracheal tube is in place. If a different type of nebulizing catheter is required, such as for sterility purposes, the endotracheal tube need not be replaced as well.

Another advantage of providing the nebulization catheter as a separate, removable device is that it can be accommodated in a variety of other instruments and/or devices. For example, the nebulization catheter of FIGS. 1–5 is shown used in an endotracheal tube; however, the nebulization catheter could also be positioned inside of a bronchoscope, such as in a working channel of a bronchoscope. The nebulizing catheter could be positioned in any instrument that is positioned in the respiratory tract and that can accommodate the nebulizing catheter size.

The nebulizing catheter may be provided with radiopaque markings 41 to facilitate positioning and placement. The radiopaque markings 41 may be provided by radiopaque bands of metal or heat shrunk bands of doped radiopaque plastic that are attached to the nebulizing catheter, or alternatively the markings may be provided by doping the plastic material of the nebulizing catheter with a radiopaque material. Alternatively, a radiopaque dye may be added to the liquid being delivered by the nebulization catheter to assist observation. The markings 41 may be graduated to facilitate recognition, or alternatively may extend over a portion or all of the nebulizing catheter. In still a further embodiment, the markings may be formed of a ultrasonic reflectors, e.g. textured material, that are visible by means of ultrasonic imaging. The nebulization catheter may also include a stripe 43 extending along a side of the shaft (as shown in FIGS. 5 and 6). The stripe 43 may be radiopaque or ultrasonically visible and may be used to determine the rotational orientation of the shaft. The stripe may be formed by a coextrusion process or by embedding a wire in the wall of the nebulization catheter.

One method that may be employed to facilitate positioning of the nebulization catheter is to monitor the pressure at the distal end of the endotracheal tube as the nebulization catheter is being advanced. Monitoring the pressure at the end of the endotracheal tube may be accomplished through one of the endotracheal tube lumens. The gas source connected to the proximal end of the nebulization catheter may be operated so as to expel a gas from the distal end of the nebulization catheter as it is being advanced. The gas being expelled from the distal end of the nebulization catheter affects the pressure being detected through the endotracheal tube. When the distal end of the nebulization catheter passes the distal end of the endotracheal tube, the pressure being measured through the endotracheal tube abruptly changes thereby providing a clear indication of the location of the distal end of the nebulization catheter relative to the endotracheal tube.

The nebulizing catheter may also include a safety stop 44 located along a proximal portion that engages a portion of the endotracheal tube proximal portion or a fitting thereon, as shown in FIG. 2. The safety stop 44 ensures that the distal end of the nebulizing catheter 20 is correctly positioned with respect to the distal end 46 of the endotracheal tube 10 and prevents the distal end 37 of the nebulizing catheter from extending too far into the trachea. In addition to the safety stop 44, the proximal portion of the nebulizing catheter 20 may also have graduated markings 48 that would be visible to the physician handling the proximal end of the nebulizing catheter to enable a determination of the position of the distal end 37 of the nebulizing catheter 20 relative to a distal end 46 of the endotracheal tube 10.

The nebulizing catheter 20 may also include a critical orifice 49 located at a proximal portion of the nebulizing catheter. The critical orifice 49 may be formed by a small critical opening located in line with the gas pressurization lumen 34 of the nebulizing catheter shaft close to the manifold 24. The critical orifice 49 is sized so that if the nebulization catheter is supplied with a flow in excess of its designed operating flow, the critical orifice will allow only the designed operating flow to pass through to the distal gas orifice. Alternatively, a safety valve may be located in the proximal portion of the catheter shaft. The safety valve would be designed to open if supplied with an excess of pressure.

In addition, the nebulizing catheter may include a centering device 50. The centering device 50 is located close to a distal end of the nebulizing catheter shaft and helps to center and align the distal end of the nebulizing catheter for improved performance, as explained in more detail below.

According to one embodiment, the removable nebulization catheter 20 is enclosed in a storage sheath 51. The storage sheath 51 may be similar to the type of storage sheaths used in conjunction with suction catheters. The storage sheath is preferably flexible, collapsible, or extendable to accommodate insertion of the catheter. The storage sheath 51 may be connected to the fitting 14. The storage sheath 51 can be used to receive the nebulizing catheter 20 when it is being withdrawn from the endotracheal tube 10. The storage sheath 51 is sealed and can maintain the withdrawn nebulizing catheter in an isolated condition when it is temporarily removed from the patient's respiratory system. The storage sheath 51 also allows the physician to re-insert the nebulization catheter into the patient. In this manner, the nebulization catheter can be reused in a limited way with respect to a patient and can be maintained in a sterile condition while withdrawn from the patient. The storage sheath 51 may have a distal sleeve 53 that can slide along the shaft of the nebulization catheter so that the nebulization catheter may be advanced into the ventilation lumen of the endotracheal tube or withdrawn into the storage sheath 51. The sleeve 53 may have a close fitting seal 55 located therein which is designed to clean and/or wash the nebulization catheter when it is withdrawn into the sheath. Alternatively, a cleaning seal 55 may be located in the port 16 of manifold fitting 14.

Another feature that may be used in conjunction with certain procedures is radiation shielding. Some procedures for which the nebulization catheter may be used may involve the delivery of radioactive agents, e.g. tracers to the lungs. To minimize exposure to radioactive materials, the nebulizing catheter may be provided with shielding over all or a significant portion of the overall length of the catheter. Shielding may also be provided at the liquid source reservoir.

The nebulizing catheter is preferably constructed of a biocompatible, chemically resistant polymer in order that it is suitable for use with a wide variety of drugs. The catheter shaft is preferably clear to allow visualization of contaminants or blockages of the interior lumens. Also, the portion of the catheter shaft that forms the liquid lumen 33 is preferably composed of a relatively non-compliant material. In a present embodiment, the catheter shaft is composed of a polymer such as polyethylene or nylon. A polymer tubing is extruded with multiple lumens to be used for the separate gas and liquid lumens. In order to produce a nebulization catheter with the tapered distal section 40, a multi-lumen extruded tubing may be drawn down in a portion thereof to form the tapered distal section 40. The draw down ratio may be selected to provide a nebulization catheter shaft with the desired dimensions. The draw down process serves to make the lumens smaller in size distally as well as closer together while maintaining the proximal cross sectional profile of the multi-lumen tubing. The larger proximal profile provides for greater pushability in the catheter shaft and facilitates manufacturing by making the manifold connection easier. The draw down ratio used on the extruded polymer tubing may be on the order of 2-to-1, 5-to-1, or even as high as 20-to-1 or higher. Prior to drawing down, the extruded polymer tubing is preferably exposed to high energy radiation to crosslink the polymer molecules to provide for favorable material properties, such as the ability to maintain orifice dimensions and tolerances. The radiation may have an energy of approximately 10–700 kgy. After the crosslinking step, the tubing is heated to its transition temperature between its melt and glass states, and is drawn down by the desired ratio.

As an alternative to drawing down the extruded tubing, the multi-stage nebulization catheter shaft may be formed by a bubble extrusion process wherein the desired tapered distal section is formed directly in the shaft as it is being extruded. Again, this process may be used for manufacturing efficiency and convenience. As another alternative, the multi-stage shaft may be formed by a combination of both bubble extrusion and drawing down. Still another alternative for forming the desired tapered profile for the nebulizing catheter shaft is to use a material that can be cold drawn in order to cause a sharp neck down in diameter, such as a linear low density polyethylene. Although the process for forming the tubing is particularly suited for producing a nebulization catheter shaft for use in delivering medicine to the respiratory tract, it should be understood that the process could be used to produce aerosol nozzles for non-medical purposes as well.

Alternatively, all or part of the nebulization catheter shaft can be molded, especially at locations where close tolerances are preferred such as at the tip.

After the shaft is formed with the desired stages, it is cut and assembled with the other components of the nebulizing catheter. Although the nebulization catheter is preferably constructed of a polymer, in an alternative embodiment it could be formed of other materials such as a metal, especially a malleable metal to facilitate drawing, shaping or forming orifices. During the manufacturing process, the nebulizing catheter may be pre-sterilized by means of a conventional process, such as a gamma ray or electron beam. The nebulizing catheter is preferably disposable after use with a single patient, but may be reused to a limited extent with a single patient provided that contamination can be prevented such as through the use of the sheath 51, described above. The nebulizing catheter shaft preferably possesses torsional rigidity so that rotation of the proximal end is transmitted at a 1:1 ratio to the distal end. The nebulizing catheter may also be provided with an antiseptic coating.

Drug delivery rates are closely related to the particle size with larger particles providing greater delivery rates. The embodiments of the nebulization catheter described herein have the capability of generating particle distributions with a GSD between 2 and 2.5. Drug delivery rates in a range between approximately 5 and 1000 mg (0.005–1.0 ml) per minute may be obtained. A variety of particle size distributions can be generated at most flow rates through selection of the catheter type and aerosol volume output. An aerosol of this type can be generated with the nebulization catheter using a gas flow rate as low as 0.1 liter/minute.

There are a number of factors that affect the particle size generated. These factors include: (1) the gas orifice diameter, (2) the liquid orifice diameter, (3) the liquid delivery tube outer diameter and geometry, (4) the distance between the gas and liquid orifices, (5) the rate of gas delivery, and (6) the pressure of the liquid. of course, the size of the solid particles in suspension, if present, in the liquid are a defining aspect of the aerosol particle size generated. In addition, there are other factors that affect the aerosol particle size such as the characteristics of the liquid, e.g. viscosity, suspension, surface tension and the composition of the driving gas, however, these factors affect the particle size of the aerosol generated to a lesser degree. By selectively varying these parameters, the size and size distribution of the aerosol particles can be changed from less than a micron to at least 10 microns.

The embodiments of the present invention, described herein are suitable for delivery of an aerosol by nebulization with a volumetric particle size distribution comparable to other nebulization systems. Further, by generating an aerosol at a location in the trachea or even deeper in the bronchi, impaction losses in tract can be avoided. By reducing impaction losses, it may be acceptable to use larger particle sizes (e.g. greater than 5 microns). The combination of lower impaction losses and larger particle sizes may provide higher effective delivery rates than prior systems. Reducing impaction losses would enable an embodiment of the nebulization catheter to provide acceptable delivery rates with aerosol particle sizes greater than 5 microns.

Referring to FIGS. 3–5, there is depicted a further embodiment of the present invention. According to the embodiment of FIGS. 3–5, there is provided an endotracheal tube 52 and a nebulizing catheter. The nebulizing catheter may be similar to the nebulizing catheter 20 shown in FIGS. 1 through 3. In the embodiment of FIGS. 3–5, the endotracheal tube 52 has an auxiliary lumen 56 in addition to its main ventilation lumen 60. Some endotracheal tubes provide auxiliary lumens through the shaft wall. The auxiliary lumen 56 is preferably sized and adapted to receive the separate nebulization catheter 20. This embodiment provides many of the same advantages as the embodiment of FIGS. 1 through 3. In addition, in this embodiment, the auxiliary lumen 56 may be provided with a distal aperture 64 that facilitates locating and aligning the distal end of 37 the nebulizing catheter 20 at a desired location for nebulization purposes.

In the embodiments of the invention shown in FIGS. 1–5, the nebulizing catheter 20 is shown used in conjunction with an endotracheal tube either of a conventional type 10, as in FIGS. 1 and 2, or of a type especially designed for use with the nebulizing catheter such as endotracheal tube 52 of FIGS. 3–5. The nebulizing catheter 20 according to an embodiment of the present invention may also be used without a separate endotracheal tube, i.e. the nebulizing catheter may be used on a patient who is not intubated, as shown in FIG. 6. If used on a spontaneously breathing patient (without an endotracheal tube), the patient should be properly anesthetized and/or that the airway passage of the patient be topically anesthetized. The nebulizing catheter 20 is positioned in the respiratory system of a patient directed past the carina 68 into one of the bronchi 72 of the lungs. Alternatively, the nebulizing catheter 20 may also be positioned proximal of the carina in the trachea, as desired. Embodiments of the nebulizing catheter may also be used on patients who have had tracheotomies or who have tracheotomy tubes.

In the embodiment of FIG. 6, a guiding sheath 73 is used. The guiding sheath 73 is used to help position the nebulizing catheter 20 in the respiratory system of the patient. The guiding sheath 73 includes a lumen through which the nebulization catheter 20 can be advanced into a desired bronchi site. To facilitate positioning the nebulization catheter, the guiding sheath 73 may have a pre-shaped distal end to facilitate locating the sheath in the desired airway passage. Alternatively, the guiding sheath 73 may have a distal end that can be formed into a desired shape by the physician just prior to insertion. The guiding sheath 73 differs from the endotracheal tube 10 of FIGS. 1–5 in that it may have a smaller outside diameter so that it can be advanced into smaller airway passages deep in the patient's bronchi past the carina 68. The inside diameter of the sheath 73 is large enough to advance the nebulization catheter. The guiding sheath 73 is particularly useful when the nebulization catheter 20 is being located deep in the patient's lungs, or when the nebulization catheter is used without an endotracheal tube. The guiding sheath 73 may also be used with an endotracheal tube through the ventilation lumen thereof. The guiding sheath is preferably composed of a torsionally rigid material so that the distal end of the guiding sheath is responsive to rotation at the proximal end.

Referring to FIGS. 7 and 8, there is shown another embodiment of the nebulizing catheter. In the embodiment of FIG. 7, a nebulizing catheter 76 includes an occlusion balloon 80 located on a distal exterior surface of the nebulizing catheter shaft body 84. The nebulizing catheter 76 may include an additional lumen 88, as shown in FIG. 8, located therethrough and communicating with the interior of the balloon 80 for providing inflation fluid, i.e. preferably gas, to expand the occlusion balloon 80. This lumen 88 for inflation fluid is in addition to the lumens 92 and 96 in the catheter shaft 84 used for conveyance of the liquid medicine and pressurized gas, respectively. The occlusion balloon 80 may be used to position the nebulizing catheter in the appropriate respiratory branch 100, center the nebulizing catheter tip for proper orientation, and isolate a particular bronchus, as needed. The embodiment of the nebulizing catheter 76 shown in FIG. 7 may be used with an endotracheal tube in a manner similar to that shown in FIGS. 1–3, or alternatively it may be used without a separated endotracheal tube, similar to the embodiment of FIG. 6. When used without a separate endotracheal tube, the nebulizing catheter 76 of FIG. 7 could be used for the purpose of selective ventilation of one of the bronchi of the lungs even without providing aerosolization. Alternatively, the nebulization catheter 76 could provide aerosolization on an intermittent basis with continuous ventilation. If the nebulization catheter is used to provide ventilation as well as aerosolized medication, the ventilation regime can be tailored to maximize aerosol transport.

In addition, to further facilitate positioning and placement, the nebulizing catheter 76 may be used with a guide wire 104. The nebulizing catheter may be provided with a separate guide wire lumen 108 to receive the guide wire 104, or alternatively, the guide wire may use one of the existing lumens that is also used for either the pressurized gas or the liquid or alternatively the guide wire may be incorporated and fixed into the nebulizing catheter so that it is non-removable. The guide wire, whether of the removable type of the type that is fixed to the nebulizing catheter, may also be steerable, i.e. so that it can be guided from a proximal end to access the appropriate location in the lungs. The steering apparatus may utilize selective tensioning of a pull wire, etc. from a proximal end. If the guide wire is of the separate removable type, it may be withdrawn after it has been used to position the distal tip of the nebulizing catheter so as to avoid interfering with aerosol delivery. In addition, the distal tip of the guide wire or nebulization catheter may be pre-shaped or shapable by the physician so as to impart an appropriate curve or bend to facilitate access to the desired airway.

Referring to FIG. 9, there is shown another embodiment of a nebulizing catheter of FIG. 7. The embodiment of FIG. 9 is similar to the embodiment of FIG. 7 with the exception that the separate guide wire 104 is received in a loop 106 located close to a distal end of the nebulizing catheter 76. Proximal of the loop 106, the guide wire 104 is positioned adjacent to the shaft 84 of the nebulizing catheter 76. Instead of a loop 106, the guide wire may be received in a short lumen located in the distal end of the nebulizing catheter.

II. Generation of Aerosol Plume

It has been discovered that the shape of the aerosol plume can be a significant factor affecting the rate and efficacy of the delivery of medication by an aerosol. In general, it is preferable to generate an aerosol that has a shape that minimizes particle impaction near the distal tip of the nebulizing catheter, given the location of the tip and the airflow conditions around it. For example, if the aerosol plume is wide, a portion of the drug may be wasted in the end of the endotracheal tube or on the wall of the trachea or other airway passage. on the other hand, if the plume is too narrow or the velocity too high, a portion of the drug may impact excessively on the patient's carina. In general, a low aerosol particle velocity is desirable. One of the reasons for this is to avoid impacting the carina with the discharge of high velocity aerosol particles. In addition, it is also generally desirable to have as wide an aerosol plume as possible while avoiding significant impact with the walls of either the endotracheal tube or the respiratory airway passage. The effects of aerosol plume velocity and geometry are related to anatomical factors. In some circumstances, e.g. away from the carina, a narrow, fast aerosol plume may be preferable to a slower, wider plume.

Regarding the embodiments described below, certain of the embodiments may be preferable from the standpoint of versatility, i.e. they may be able to deliver a variety of medications having different viscosities, suspensions, surface tensions, etc. Others of the embodiments may be more suitable for the delivery of specific types of medications or the delivery of particles of certain sizes.

Referring to FIG. 10, there is shown a tip configuration for a nebulizing catheter 112. The nebulizing catheter 112 may be either a stand alone-type of nebulizing catheter, similar to the catheters shown in FIGS. 6 and 10, or may be incorporated into an endotracheal tube either removably, as in FIGS. 1–5, or non-removably. In the embodiment of FIG. 10, the nebulizing catheter 112 has a coaxial configuration. Specifically, the nebulizing catheter 112 includes an outer tubular member 116 defining a lumen 120 and an inner tubular member 124 also defining a lumen 128. The inner tubular member 124 is located in the lumen 120 of the outer tubular member 116. According to the embodiment shown FIG. 6, pressurized gas is conveyed in the annular region defined between the inner and outer tubular members. Liquid medication is conveyed in the lumen 128 of the inner member 124. As shown in the embodiment of FIG. 10, a distal end of the outer tubular member 116 is approximately adjacent to a distal end of the inner tubular member 124. In the embodiment of FIG. 10, the outer tubular member 116 has an O.D. of approximately 0.008 inches and an I.D. of approximately 0.006 inches. The inner tubular member 124 has an O.D. of approximately 0.003 inches and I.D. of approximately 0.0015 inches. Both the inner tubular member 124 and the outer tubular member 116 have larger dimensions proximal of the distal tip portion. Along a main shaft portion proximal of the distal tip, the outer tubular member 116 has an O.D. of approximately 0.115 inches and an I.D. of 0.080 inches and the inner tubular member 124 has an O.D. of approximately 0.060 inches and an I.D. of 0.050 inches.

Figure 11:
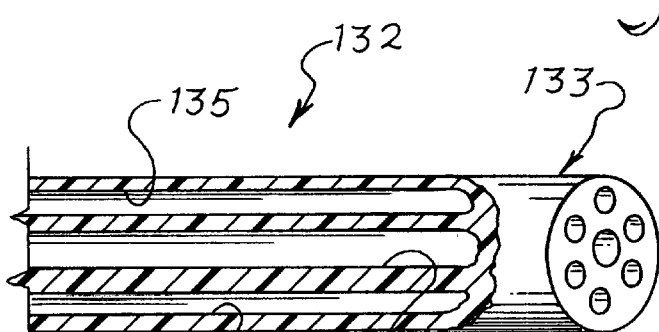
FIG. 11 is a perspective view of a distal end of an alternative embodiment of the nebulization catheter shown in FIG. 1.

The embodiment of FIG. 11 shows a tip of a nebulizing catheter 132. This embodiment is similar to the embodiment of FIG. 10. The tip 133 is formed with a plurality of lumens terminating in a plurality of orifices. An inner lumen 134 is used to convey the liquid medication and the surrounding lumens 135 convey the pressurized gas used to nebulize the liquid. This embodiment has the advantage that the orifice of the liquid lumen 134 is centered with a fixed spacing relative to the orifices of the gas lumens 135 around it. In the embodiment of FIG. 11, the multiple lumen construction may extend all the way back to the proximal end of the nebulizing catheter 132 or alternatively, only a distal segment may have the multiple gas lumen configuration in which case the pressurized gas may be conveyed through a single proximal lumen that connects to the multiple distal lumens.

Figure 12:
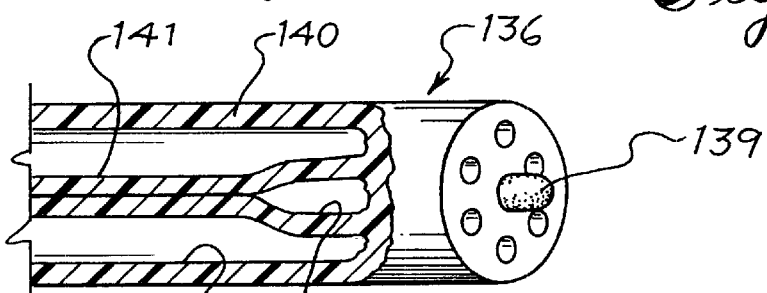
FIG. 12 is a perspective view of an alternative embodiment of FIG. 11 with the liquid lumen shown in a closed condition.
Figure 13:
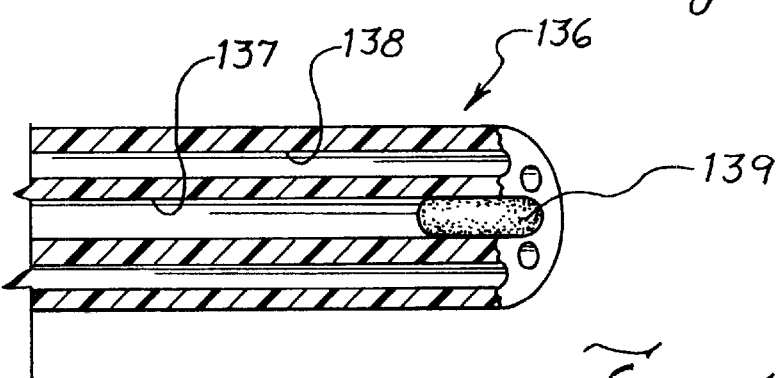
FIG. 13 is a perspective view of the embodiment of FIG. 12 with the liquid lumen shown in an open condition.
Figure 14:
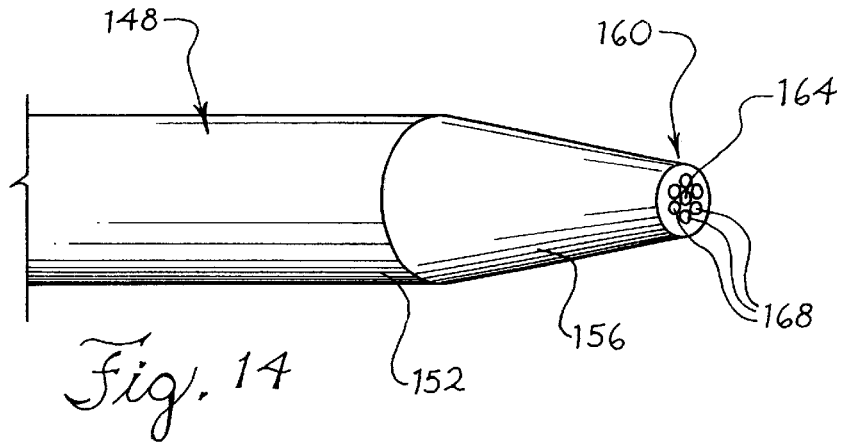
FIG. 14 is a perspective view of a distal end of an alternative embodiment of the nebulization catheter shown in FIG. 1.
Figure 15:
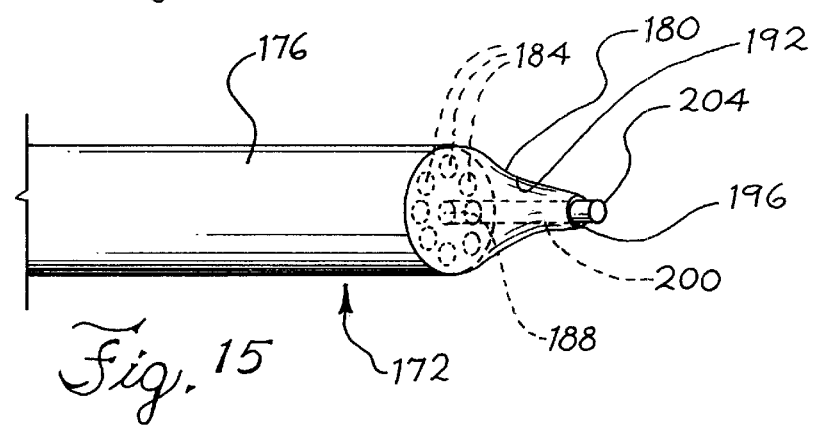
FIG. 15 is a perspective view of a distal end of an alternative embodiment of the nebulization catheter shown in FIG. 1.
Figure 16:
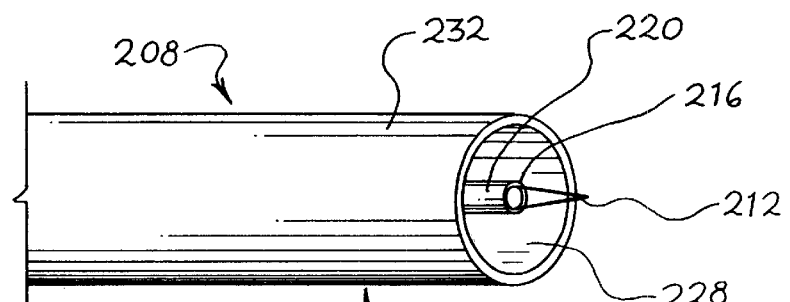
FIG. 16 is a perspective view of a distal end of an alternative embodiment of the nebulization catheter shown in FIG. 1.
Figure 17:
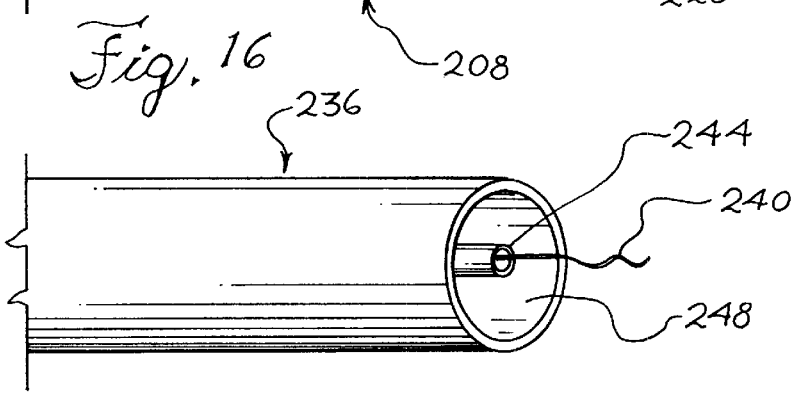
FIG. 17 is a perspective view of a distal end of an alternative embodiment of the nebulization catheter shown in FIG. 10.

FIGS. 12 and 13 show an alternative embodiment 136 of the multiple lumen nebulization catheter in FIG. 11. The embodiment in FIGS. 12 and 13 is useful when it is desired to provide the aerosol medicine with a pulsed delivery. The pulsed delivery may be timed to coincide with the inhalation of the patient so that aerosol is not wasted when the patient is exhaling. A potential drawback with pulsed delivery is that the aerosol may drool from the tip of the nebulizing catheter when the pressure being applied to the liquid is reduced to effect the pulsation. To avoid this potential problem, the nebulizing catheter 136 provides for closure of the liquid lumen when the pressure being applied to it is reduced. As in the previously described embodiment, the nebulization catheter 136 in FIGS. 13 and 14, has a centrally located lumen 137 for delivery of a liquid medicine and a plurality of lumens 138 surrounding the central lumen 137 for conveyance of a pressurized gas to nebulize the liquid at the distal orifice 139. In this embodiment, the catheter 137 is formed of a low compliance material in the outer wall area 140 and a relatively high compliance material in the area 141 surrounding the centrally located liquid lumen 137. These differing compliance characteristics may be formed in the catheter shaft by coextruding a single tube with different materials. When using the embodiment of FIGS. 12 and 13, a constant, relatively high pressure is applied to the gas in the lumens 138. Liquid medicine is delivered via the lumen 137 and pressure pulses are applied to the liquid from an external delivery source, such as a pump. When the pressure in the liquid lumen 137 is low, the high pressure in the gas lumens 138 deform the compliant inner material 141 thereby compressing the liquid lumen 137 and closing it off, as shown in FIG. 12. When a pressure pulse is applied to the liquid in the lumen 137, it overcomes the compressive forces from the gas lumens 138 allowing the lumen 137 to open and permitting the liquid medicine to be delivered to the distal orifice 139 to be nebulized, as shown in FIG. 13. In this manner, the embodiment of FIGS. 12 and 13 provides for pulsed liquid nebulization with reduced possibility of drooling.

Another feature shown in FIGS. 11 and 12 is a porous plug 142 located in the liquid orifice 139. This porous plug may be made of a felt-like material and may assist in the production of fine aerosol particles.

The embodiment of FIG. 14 shows a distal tip of another embodiment of the nebulizing catheter. In this embodiment, a nebulizing catheter 148 includes a main shaft section 152 and a distal shaft section 156. The distal shaft section 156 is tapered to a tip 160. At the tip 160, a liquid orifice 164 is surrounded by a plurality of gas orifices 168. In a preferred embodiment, there are six gas lumens terminating in the six orifices 168. In this embodiment, the liquid orifice 164 has a diameter of approximately 0.002 inches and the gas orifices 168 each have a diameter of approximately 0.002 inches. This embodiment is similar to the embodiment of FIG. 11 except that the distal section 156 provides for a reduction in the tip size and corresponding modification of the nebulization plume properties. This reduction is preferable as it provides a smaller orifice size.

The embodiment of FIG. 15 shows a distal portion of a nebulizing catheter 172. In this embodiment, the nebulizing catheter includes a proximal shaft section 176 and a distal shaft section 180. The proximal shaft section 176 includes a plurality of lumens 184. A central one 188 of the plurality of lumens 184 is used to convey liquid medicine and the remainder of the lumens surrounding it are used to convey gas. The distal shaft section 180 connects to the distal end of the proximal shaft section 176 and defines a tapered cavity 192 between the distal end of the proximal shaft section 176 and a distal orifice 196. At least one of the plurality of lumens 184 is used to convey a pressurized gas that is discharged into the cavity 192. A tubular extension 200 extends the liquid lumen through the cavity 192 and distally out the orifice 196. The orifice 196 is sized to provide an annular region around the tubular extension 200 to permit the pressurized gas to flow through to nebulize the liquid medication that exits a distal orifice 204 of the tubular extension 200. In a preferred embodiment, the distal shaft section 180 is composed of stainless steel and the orifice has an I.D. of 0.025 inches. The tubular extension 200 has an O.D. of 0.012 inches and an I.D. of 0.007 inches. This embodiment has the advantage of combining a relatively small distal profile with a relatively large proximal flow channel. Another advantage of this embodiment it that it provides for a balanced airflow around the liquid orifice 204.

FIG. 16 shows yet another embodiment for a tip for a nebulizing catheter. In FIG. 16, a nebulizing catheter 208 has a coaxial configuration similar to the embodiment of FIG. 10 (although it could also have a configuration similar to that of other coaxial embodiments, e.g. FIGS. 11, 14, or 15). In FIG. 16, a thin solid wire or filament 212 is located at a distal end of a liquid orifice 216 located at a distal end of an inner tubular member 220. The tapered wire 212 extends a short distance distally from the distal end of the inner tubular member 220. The tapered wire 212 is located with respect to the liquid orifice 212 so that liquid being conveyed through the inner member 220 continues to flow distally of the distal orifice 216 along the wire 212, i.e. adhering to it by surface tension. of course, once the liquid reaches a distal tip 224 of the wire 212, it is entrained and nebulized by the gas flow from the annular region 228 defined between the inner tubular member 220 and an outer tubular member 232. As mentioned above, one of the factors that affects the nebulization plume particle size and geometry is the size of the distal liquid orifice. In general, a smaller liquid orifice produces smaller particles and a narrow aerosol plume cone. In the embodiment of FIG. 16, the thin wire 212 carries only a small amount of liquid along it so that it functions similarly to an orifice of a very small size. Accordingly, the embodiment of FIG. 16 has the potential for producing an aerosol of very fine particles. In the embodiment of FIG. 16, the outer tubular member has an I.D. of approximately 0.020 inches. The inner tubular member has an I.D. of approximately 0.006 inches. The thin wire has an O.D. of approximately 0.002 inches. The wire or filament 212 may be composed of a metal wire or a polymer wire, such as a polyolefin fiber like Spectra fiber. Alternatively, the filament 212 may be composed of a porous or felt-like material, such as nylon or Porex, in which case it may be wider in diameter than if made of a solid material.

FIG. 17 shows an alternative embodiment of the embodiment of FIG. 16. In FIG. 17, there is a distal end of a nebulizing catheter 236 having a tapered wire or filament 240 located at the distal end of a lumen of an inner tubular member 244. The tapered wire 240 in this embodiment has a curved shape that is designed to whip in a spiral when it is in a flow of air. In the embodiment of FIG. 17, when pressurized gas flows through the annular region 248, it causes the tapered wire 240 to whip around with a spiral motion. The length of the wire 240 is chosen so that it does not impact the wall of the trachea or other airway passage when it moves in a spiral whipping motion. In one embodiment, the wire 240 has a length of approximately 1–2 mm. The tapered wire 240 carries the liquid out to its tip for entrainment, and the nebulization plume is formed with a conical shape. The width of the plume may be changed by changing the length of the filament 240. The speed of the spiral motion can be controlled by appropriate selection of wire stiffness and air foil shape. In general, the spiral plume produced by the embodiment of FIG. 17 will be wider than the embodiment of FIG. 16 and have less forward velocity. Both these characteristics may be favored in a nebulization catheter.

FIGS. 18 and 19 show another embodiment of the nebulization catheter. In this embodiment, a nebulization catheter 252 has a coaxial configuration formed of an outer tubular member 256 and an inner tubular member 260. A distal plug 264 fits into a distal end of the annular region 268 forming the gas lumen. A plurality of apertures 272 extend through the plug 264 to form distal gas orifices. Located in a lumen 276 defined by the inner tubular member 260 is a retractable wire or pin 280. The wire 280 is preferably a solid wire of a rigid material. For example, the wire may be composed of a metal, such as stainless steel, a polymer, or a radiopaque material. A distal end 284 of the inner member 260 is tapered and may extend distally of the plug 264 or alternatively may extend only to the distal end of the inner tubular member 260 or even proximally thereof. The distal end of the inner member 260 terminates in a distal liquid orifice 285. A distal end 286 of the wire 280 may also be tapered. The wire 280 is sized with respect to the inner tubular member 260 so that the tapered distal portion 286 of the wire 280 seats against the tapered distal portion 284 of the inner tubular member 260 and thereby seals a distal end of the liquid lumen 276 in a manner similar to a needle valve. The wire 280 is retractable and in a preferred embodiment is operated to reciprocate back and forth to pulse the delivery of liquid out the distal end of the nebulizing catheter 252. The pulsing of aerosol delivery may be adjusted to any suitable time period. In one preferred mode of operation, the aerosol may be delivered only during inhalation by the patient. If the nebulizing catheter 252 is being used with an endotracheal tube and a ventilator, the pulsing of the aerosol delivery may be timed to coincide with the patient's inhalation by an appropriate connection with the ventilator. By limiting the delivery of medicine to only the period of time when the patient is inhaling, the medicine can be delivered more efficiently and with less waste.

One preferred way to generate the pulsed aerosol plume with the embodiment of FIGS. 18 and 19 is with a manifold arrangement 287. A proximal end of the wire 280 is fixed to an extendable section 288 of the manifold 287. The wire 280 may be fixed by means of an elastomeric seal 289. Pressurized gas is delivered to a port 290 of the manifold that communicates with the outer tubular member 256 and liquid medicine to be nebulized is delivered to a second port 291 that communicates with the inner tubular member 260. The liquid medicine also fills the volume 292 proximal of the port 291 in the expandable section 288. The wire 280 is connected to the manifold so that the distal end of the wire is biased against the distal end of the inner tubular member by the resilience of the inner tubular member 260 and/or the expandable section 288. Pulsed pressurization of the liquid medicine from the source causes the extendable section 288 to reciprocate back and forth as shown by the arrow 293. Since the proximal end of the wire 280 is attached to the expandable section 288 proximal of the port 291, application of pressure pulses to the liquid causes the proximal end of the wire 280 to reciprocate back and forth as well. This causes the distal end of the wire 280 to reciprocate back and forth in the seat 284. Application of pressure pulses to the liquid medicine can be timed to coincide with the patient's inhalation. Alternatively, instead of forming an expandable or compressible section at the manifold, the shaft of the inner tubular member 260 may be formed of a stretchable material so that pressurization of the liquid causes retraction of the wire as the entire shaft elongates. Other alternatives for effecting reciprocating operation of the wire 280 are use of an electro- mechanical, mechanical, hydraulic, or pneumatic actuator to drive the wire. Aside from providing for pulsed delivery of the aerosol, this embodiment of the nebulization catheter has the further advantage that the reciprocating action of the wire may assist in keeping the orifice free of any blockages which may occur, especially with some viscous solutions or suspensions.

In a manner similar to the embodiments 208 and 236 of FIGS. 16 and 17, in the embodiment 252 of FIGS. 18 and 19, the distal tip of the retractable wire 292 can extend distally from the distal liquid orifice 288 in order to minimize particle size, or alternatively may not extend distally of the distal liquid orifice 292. In one embodiment, the distal tip of the retractable wire may extend distally of the liquid orifice 288 by approximately 0.2 mm.

FIG. 20 shows another embodiment of a nebulizing catheter. In this embodiment, a nebulizing catheter 296 has a main shaft portion 300 with a gas lumen 304 adjacent to a liquid lumen 308. The gas and liquid lumens 304 and 308 flow into a distal cavity 312. The distal cavity 312 is formed by an outer tubular extension 316 that extends distally over and past a distal end 320 of the main shaft portion 300. A filter 324 is located in the liquid lumen 308 to filter out any particles in the liquid. The liquid lumen 308 has a step down in diameter immediately distal of the location of the filter 324. An insert plug 328 is located in a distal end of the outer tubular extension 316. The insert plug 328 (which may be a sapphire jewel, for example) has an aperture 332 through it that forms an exit orifice from the cavity 312. The insert plug 328 has a conical shaped proximal profile facing the cavity 312. An inner tubular extension 336 fits into the stepped down portion of the liquid lumen 308 and extends the liquid lumen 308 into the cavity 312. A distal end 340 of the inner tubular extension 336 terminates in the cavity 312. Since the gas lumen 304 exits into the cavity 312, nebulization of the liquid takes place at the tip of the inner tubular extension 336 inside the cavity 312. This region of the cavity 312 is a positive pressure region due to the relative sizes and locations of the apertures. The positive pressure in this region may have the effect of reducing drooling of the liquid medicine as it leaves the orifice of the tubular extension 336. The aerosol exits the catheter 296 via the aperture 332 and the aerosol plume is defined in part by the positive pressure in the cavity 312 and the aperture size. In this embodiment, the main shaft portion and the tubular extension are composed of a suitable plastic such as polyethylene. The filter is composed of multiple 50 $\mu$m I.D. tubes or similar course filter material. The gas and liquid lumens may each have an I.D. of 0.010 to 0.015 inches. The inner tubular extension 336 may be formed of polyimide tubing with an I.D. of 0.004 inches and an O.D. of 0.010 inches. The outer tubular extension 316 may be formed of a heat shrunk tubing, such as polyethylene. The plug 328 may have an O.D. 0.087 inches and the aperture 332 in the plug 328 may have a diameter of 0.007 inches.

FIG. 21 shows another embodiment of the nebulizing catheter. This embodiment is similar to the embodiment 296 shown in FIG. 20 and accordingly the components are numbered similarly. The embodiment of FIG. 21 differs from the embodiment of FIG. 20 in that the distal end of the inner tubular extension 312 is located in the aperture 332 of the insert plug 328. In the embodiment of FIG. 21, the orifice 332 at the distal end of the tubular extension 336 is in a low pressure, high velocity region as compared to the embodiment of FIG. 20. This has a corresponding effect on plume size and shape as well as possible particle size.

FIG. 22 shows yet another embodiment for the nebulizing catheter. In this embodiment, a nebulizing catheter 340 has a main shaft portion 344 that has a gas lumen 348 and a liquid lumen 352. The gas lumen 348 terminates distally in a gas orifice 356. Located in the distal end of the liquid lumen 352 is a liquid tubular extension 360. The liquid tubular extension 360 forms an angle so that a distal liquid orifice 364 is in alignment with the flow of gas out the distal gas orifice 356. In this embodiment, the liquid lumen 352 has an I.D. in the range of 0.010 to 0.020 inches. The gas lumen 348 has an I.D. of approximately 0.10 to 0.020 inches. The liquid tubular extension 360 is formed of a stainless steel tube with an O.D. of 0.018 inches and an I.D. of 0.012 inches. The distal gas orifice 356 has an I.D. of 0.010 inches. The stainless steel extension tube 360 forms a right angle so that the distal liquid orifice 364 is at a right angle and aligned with the distal gas orifice 356. The distal gas orifice 356 and the distal liquid orifice 364 are positioned as close together as possible, and in one embodiment, these orifices are approximately 0.010 inches apart.

Figure 23:
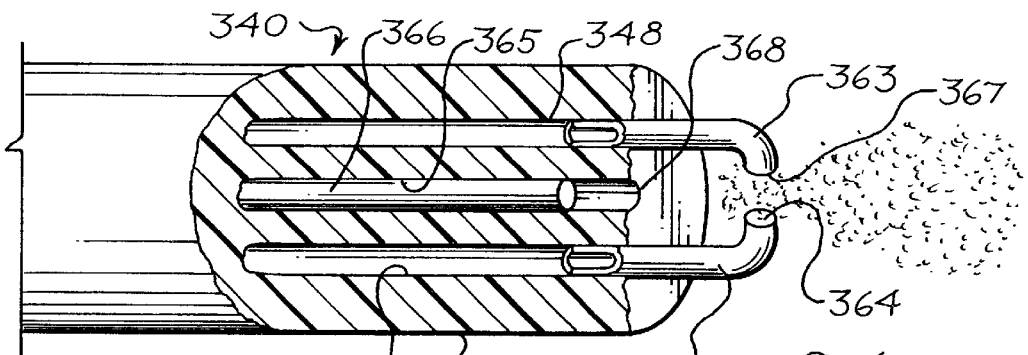
FIG. 23 is a view similar to that of FIG. 22, showing an alternative embodiment of the nebulization catheter shown in FIG. 22.

FIG. 23 shows an alternative embodiment of the nebulization catheter shown in FIG. 22. In this embodiment, the nebulization catheter 340 has an additional lumen 365. This additional lumen 365 may have an I.D. of approximately 0.020 inches. This additional lumen 365 may be used for an optical fiber viewing scope 366 for illumination and visualization of the distal end of the nebulization catheter 340. The optical viewing scope 366 may be permanently installed in the catheter 340 or preferably may be removable. A distal end 367 of the lumen 365 is open or covered with a transparent lens so that the area distal of the catheter 340 can be observed via an optical viewing device connected to a proximal end of the optical fiber 366. This enables a physician to observe the alignment of the distal end of the nebulization catheter and also observe the nebulization when it occurs. The gas orifice 356 may be located so that the pressurized gas that is expelled helps to keep the distal end of the viewing lumen 365 clear. An optical fiber viewing channel may be incorporated into any of the embodiments of the nebulization catheter disclosed herein. When the additional lumen 365 is occupied by a removable viewing scope, it may be used for other purposes such as pressure sensing, gas sampling, over pressure relief, or other diagnostic or therapeutic purposes. Alternatively, another lumen may be provided for these purposes.

The embodiment of FIG. 23 also shows opposing orifices. As in the embodiment of FIG. 22, a tubular extension 360 extends distally of the end of the catheter shaft and is oriented at an angle, e.g. 90 degrees, to the direction of the axis if the catheter shaft. The tubular extension 360 opens to a distal liquid orifice 364 from which the liquid being conveyed in the lumen 352 exits. In this embodiment, a second tubular extension 363 communicates with the gas lumen 348 and opens to a distal gas orifice 367. The second tubular extension 363 is also oriented relative to the axis of the catheter shaft, e.g. by 90 degrees, so that is aimed toward the distal liquid orifice 364 in order to nebulize the liquid exiting from the liquid orifice 367.

Figure 24:
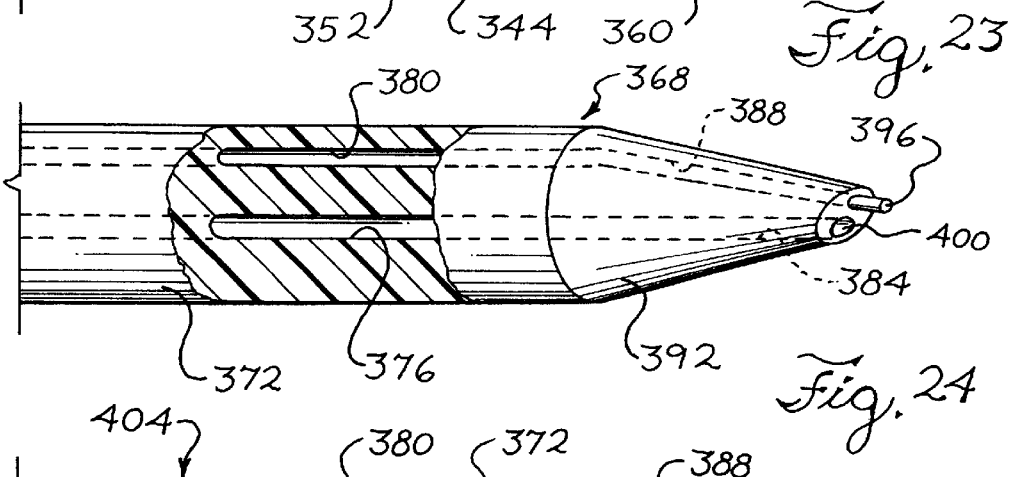
FIG. 24 is a perspective view partially in section of a distal end of an alternative embodiment of the nebulization catheter shown in FIG. 1.

FIG. 24 shows still another embodiment of the nebulizing catheter. In this embodiment, a nebulizing catheter 368 has a main shaft section 372 with a gas lumen 376 and a liquid lumen 380. Tubular extensions 384 and 388 extend the gas and liquid lumens 376 and 380 from the main shaft section 372 to a distal tip of the catheter 368. The distal portion of the shaft forms a tapered region 392 that surrounds the tubular extensions 384 and 388 and causes them to be angled toward each other. The tubular extension 388 for the liquid lumen 380 extends slightly distally of the distal end of the tubular extension 384 of the gas lumen 376 so that a distal liquid orifice 396 is in alignment with the flow of gas from a distal gas orifice 400. In this embodiment, the distal liquid orifice 396 has an O.D. of 150 microns and an I.D. of 20 microns. The gas orifice 400 has an I.D. of approximately 0.018 inches.

Figure 25:
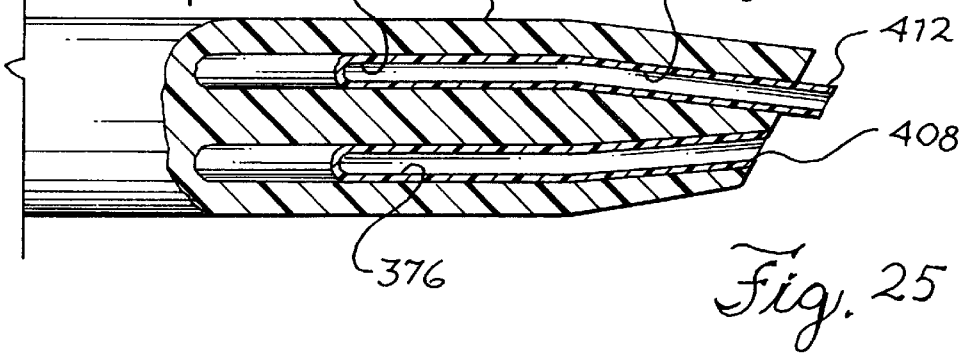
FIG. 25 is sectional view of a distal end of an alternative embodiment of the nebulization catheter shown in FIG. 25.
Figure 26:
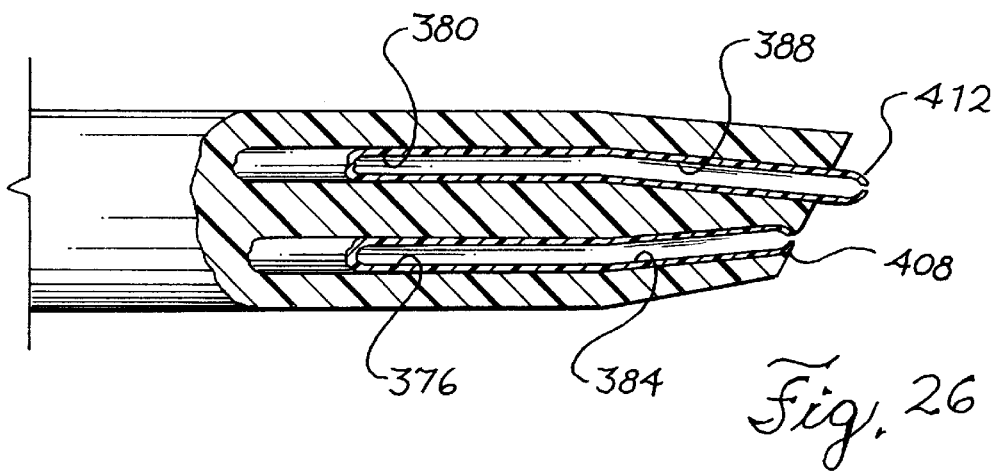
FIG. 26 is sectional view similar to that of FIG. 25 showing the embodiment of FIG. 25 during an exhalation stage of the patient.

FIGS. 25 and 26 show an alternative embodiment of the nebulizing catheter 368 shown in FIG. 24. In FIGS. 25 and 26, the tubular extensions 384 and 388 of the gas lumen 376 and the liquid lumen 380 are formed with sealable tips. Specifically, the gas tubular extension 384 has a sealable tip 408 and the liquid tubular extension 388 has a sealable tip 412. Alternatively, only the liquid lumen 380 has the sealed tip 412 and the gas lumen 376 has an open distal orifice. The sealable tips may be formed by heating the material from which the tubular extensions are made to reform the walls of the plastic material so as to form a closed slit. This is represented in FIG. 26. When pressurized gas and liquid are conveyed through the lumens 376 and 380, the slits forming the tips 408 and 412 dilate thereby permitting the gas and liquid to exit to from the aerosol, as illustrated in FIG. 25. However, when the pressure in the lumens 376 and 380 falls below a threshold, the tips 408 and 412 close thereby sealing off the lumens, as illustrated in FIG. 26. The embodiment 404 of the nebulizing catheter is used with pulsation of the gas and/or liquid supplies. In order to pulse the generation of aerosol to coincide with a patient's inhalation, the pressure to the gas and/or the liquid lumens can also be pulsed. When the pressure in either of the lumens falls below a threshold, the tips 408 or 412 close. By closing off the flow of liquid at the tip 412 during the period when the aerosol is not being generated, it is possible to reduce any drooling from the tip of the catheter.

III. Nebulization with Counterflow

As mentioned above, control of nebulized particle size and plume shape are important considerations affecting the efficacy of the therapy. In many applications, it is preferable to have as small a particle size as possible combined with as little forward velocity as possible. Some of the embodiments described below accomplish these objectives through use of counterflow arrangements.

FIG. 27 shows a nebulization catheter 416 that can be located inside of an endotracheal tube as in the previously described embodiments. The nebulization catheter 416 has a coaxial tubular arrangement with an outer tube 417 surrounding an inner tube 418 so that a liquid delivered from a distal liquid orifice 419 of the inner tube 418 is nebulized by the flow of a pressurized gas delivered in a distal direction from the annular region between the inner and outer tubes at the distal orifice 420 of the outer tube 417. In addition, another lumen 428 extends through the shaft of the nebulization catheter 416. This additional lumen 428 connects to a distal tubular extension 432. The tubular extension 432 extends distally of the distal end of the nebulization catheter 416. A distal end 436 of the distal tubular extension 432 curves back on itself so that a distal orifice 440 of the tubular extension 432 is oriented in a proximal direction back at the orifices 419 and 420 of the inner and outer tubes. The additional lumen 428 also carries a pressurized gas which is directed in a proximal direction by the orifice 440 against the direction of the aerosol plume generated by the gas and liquid exiting the orifices 419 and 420. The gas from the additional lumen 428 presents a counterflow to the gas from these orifices thereby slowing down the velocity of the particles generated from these orifices. In a preferred embodiment, the distal tubular extension 432 may be formed of a suitable material such as stainless steel needle stock. The O.D. of the nebulization catheter in this embodiment may be similar to the other nebulization catheter embodiments described above, e.g. O.D of approximately 0.038 inches. The distal tubular extension 432 may have an O.D. of approximately 0.013 inches and an I.D. of approximately 0.009 inches. In this embodiment, the outer tubular member of the nebulization catheter may have an O.D. of approximately 0.013 inches and an I.D. of approximately 0.009 inches and the inner tubular member may have an O.D. of approximately 0.003 inches and an I.D. of approximately 0.0015 inches.

FIG. 28 shows another embodiment of the present invention for a nebulizing catheter 448 that incorporates a counterflow arrangement. Like the embodiments described above, in this embodiment the nebulizing catheter 448 may be located in an endotracheal tube (not shown). The nebulization catheter 448 has a distal section 452 that curves back on itself. The nebulization catheter 448 has distal orifices 453 and 454 that generate a plume of nebulized particles in a reverse, i.e. proximal, direction. Also located in the nebulization catheter 448 is another lumen 456 for carrying a pressurized gas. The additional lumen 456 has a distal orifice 460 oriented in a distal direction. The distal orifice 460 of the additional lumen 456 is aligned with respect to the distal orifices 452 and 453 of the nebulization catheter 448 so that the flow of gas from the additional lumen 456 slows down the velocity of the nebulization plume generated from the nebulization catheter 448. The aerosol plume generated by the nebulization catheter reverses direction and is delivered to the lungs carried by the inhalation of air through the endotracheal tube or by the flow of gas from the additional lumen 456 or a combination thereof.

FIGS. 29 and 30 show another embodiment of a counterflow nebulization catheter arrangement. In FIGS. 29 and 30, a nebulizing catheter 464 is used with an endotracheal tube 468. A nebulization catheter 464 has a distal tip 472 from which a liquid medicine delivered from a distal liquid orifice is nebulized by a flow of pressurized gas from a gas orifice located adjacent to the liquid orifice. The nebulizing catheter 464 shown in FIG. 30 extends distally of the endotracheal tube 468 and has a distal section 476 that curves back on itself. The nebulization catheter 464 has distal orifices that generate a plume of nebulized particles in a reverse, i.e. proximal, direction back toward the distal opening of the endotracheal tube 464. In order to maintain a proper reverse orientation and to prevent snagging, the nebulization catheter 464 includes a wire 480 that extends from the tip 472 of the nebulization catheter 464. The wire 480 is secured to a portion of the shaft of the nebulization catheter proximal of the tip. The wire 480 can be secured by means of a heat shrunk tube 484 located on a shaft 488 of the catheter to hold the end of the wire 480. Although some aerosol may impact the wire 480, a wire having a small diameter is used to minimize losses due to such impaction. Moreover, the overall improved efficiency due to reduction in aerosol impaction on the walls of the trachea or other airway passage is expected to more than compensate for any losses due to impaction on the wire 488.

In the embodiment shown in FIG. 30, the nebulization catheter 464 directs a nebulization plume in a reverse direction back toward the distal opening of the endotracheal tube 468. The nebulization plume from the nebulization catheter encounters the flow of air from the endotracheal tube 468 during the inhalation phase of the patient. The inhalation of air through the endotracheal tube 468 causes the nebulized medicine to reverse direction and carries it to the lungs. It is noted that the reversal of direction of the nebulization plume has the effect of minimizing the aerosol particle velocity. It is also noted in the embodiment shown in FIG. 30 that the endotracheal tube 468 is provided with an inflatable cuff 492 located around the distal portion.

IV. Other Nebulization Catheter Embodiments

In the embodiments described above, the velocity of the nebulization plume was reduced by use of a counterflow of gas in an opposite direction. In the embodiment of FIGS. 31 and 32, the velocity of the nebulization particles is reduced in another manner. In FIG. 31 a nebulization catheter 496 has a liquid lumen 500 terminating in a distal liquid orifice 504 and a one or more gas lumens 508 terminating in one or more distal gas orifices 512. The liquid delivered through the liquid lumen 500 is nebulized by the pressurized gas flowing out the plurality of gas orifices 512. The nebulization catheter 496 also includes one or more additional lumens 516 that terminate in additional distal orifices 520. These lumens 516 are used to deliver a vacuum (negative pressure) at the distal orifices 520. The vacuum is provided by a suitable vacuum source (not shown) connected to proximal ends of the additional lumens 516. The vacuum delivered by the additional lumens 516 helps withdraw the pressurized gas delivered by the lumen 508 after it has nebulized the liquid delivered by the liquid lumen 500. Without the vacuum provided by the additional lumens 516, the pressurized gas delivered by the distal gas orifices 512 may continue to impart energy to the nebulized liquid particles delivered by the distal liquid orifice 504 thereby causing them to be propelled with a forward velocity. Instead, the vacuum scavenges at least some of the pressurized gas after it has nebulized the liquid so that the forward velocity of the liquid particles can be reduced. In order to facilitate scavenging of the pressurized gas, the distal liquid orifice 504, the distal gas orifices 512, and the distal vacuum orifices 520 all open into a distal cavity 524 formed by an outer tubular extension 528 of the nebulizing catheter 496. The distal extension 528 has a closed distal end 532 with a small aperture 536 located therein to emit the nebulized liquid particles with a low forward velocity. With the nebulizing gas removed, the aerosol particles are carried forward primarily only by their inertia.

The embodiment of the nebulization catheter 496 shown in FIG. 31 includes a vacuum line 516 as a means to reduce the forward velocity of the nebulization plume. Provision of vacuum line 516 to the tip of a nebulization catheter 496 can serve an additional function of balancing the gas flow and pressure delivered to the airway in which the nebulization catheter is located. This may be useful to prevent excess airway pressure generated by the catheter flow particularly in smaller airways or where a neutral flow balance may be desired. This may particularly be desired when the nebulization catheter is provided with an inflatable cuff that occludes the airway passage at the distal end of the nebulization catheter. The flow balance may be controlled with a closed or partially closed pumping system where a gas pump 537 with a single intake and outlet would be connected to the respective vacuum and gas supply lumens 516 and 508 of the catheter. Both the driving gas and vacuum would be balanced and regulated by the pump speed. A vacuum or pressure vent port 538 could be incorporated into the respective vacuum or pressure lines if a positive or negative flow balance was desired. If flow balance is a concern, but not velocity reduction, it is not important where the air flow is removed at the distal tip of the catheter and accordingly, the distal end extension 532 may not be needed. Alternatively, a flow balance may be maintained with separate a pressure and vacuum source through the use of regulators, restrictive capillary tubes or orifices, or flow sensors and flow control valves incorporated into the pressure and vacuum supply lines.

FIG. 33 shows another embodiment of a nebulization catheter 540 that incorporates a feature to reduce the forward velocity of the nebulized liquid particles. The nebulization catheter 540 has a main shaft portion 544 having a liquid lumen 548 and a pressurized gas lumen 552. The lumens 548 and 552 terminate in distal orifices 556 and 560. The pressurized gas flow from the orifice 560 nebulizes the liquid exiting from the orifice 556. The nebulization catheter 540 includes a distal spacer tube 564. The spacer tube 564 has a length of approximately 2–3 mm and an inside diameter larger than the outside diameter of the nebulization catheter shaft 544. Because the inside diameter of the spacer tube 564 is larger than the airflow lumen and orifice, the velocity of air and entrained particles is reduced as they pass through the spacer tube 564 and out a distal opening 568 thereof. In addition, the spacer tube 564 may have one or more apertures or holes 572 through a wall thereof close to the proximal end of the spacer tube at its connection to the main shaft 544. These holes 572 draw in air to the inside of the spacer tube 564 thereby causing drag due to turbulence and reducing the velocity of the aerosol as it exits the spacer tube. The holes 572 may also slow the flow of particles through the spacer tube by causing drag turbulence.

The spacer tube 564 also serves to protect the distal orifices 556 and 560 of the nebulization catheter from coming into contact with any part of the endotracheal tube, trachea, or other airway passage thereby helping to maintain optimum tip operation and to prevent damage to it during handling and insertion. In an alternative embodiment, if only the tip protection feature is desired, the spacer tube 564 of FIG. 33 may be provided without the apertures 572. In such an alternative embodiment, the spacer tube 564 may be provided in a shorter length, e.g. 1 mm.

FIG. 34 shows another embodiment of a nebulization catheter 576 used with an endotracheal tube 580. The endotracheal tube 580 may be a conventional endotracheal tube. The nebulization catheter 576 provides for a nebulization plume with a reduced forward velocity by imparting a spiral component to the liquid particle flow. The nebulization catheter 576 has a distal tip 584 from which a liquid medicine delivered from a distal liquid orifice is nebulized by a flow of pressurized gas from a gas orifice located adjacent to the liquid orifice. The nebulization catheter 576 is positioned coaxially in the endotracheal tube 580. A centering device 585 may be used to aid in centering the nebulization catheter 576. Located along a portion of the nebulization catheter 576 proximal from the tip 584 is a second gas orifice 588. This second gas orifice 588 may open to the same gas lumen that communicates with the nebulizing gas orifice at the distal tip 584 or alternatively, the second gas orifice 588 may connect to another, separate gas lumen. The second gas orifice 588 is oriented to direct a pressurized flow of gas in a spiral, distal direction along the distal end of the nebulization catheter 576. To accomplish this, the second gas orifice 588 may be formed by an inclined opening or with a deflection foil to direct the flow of gas in the appropriate spiral direction. The spiral flow of pressurized gas travels along the distal portion of the nebulizing catheter 576 inside the endotracheal tube 580. The spiral flow of gas entrains the aerosol generated from the distal end 584 of the nebulizing catheter imparting a spiral flow component to the aerosol plume. This has the effect of reducing the forward velocity component of the liquid particle flow as it leaves the endotracheal tube 580.

FIG. 35 shows an alternative method for using the nebulization catheter 576 of FIG. 34. In FIG. 35, the nebulization catheter 576 is shown extended distally of the distal end of the endotracheal tube 580 so that the distal portion of the nebulization catheter 576 including the second gas orifice 588 is located in an airway passage. Taking into account the size of the airway passage, the nebulization catheter 576 with the second gas orifice 588 would operate similarly to the method shown in FIG. 34 and generate a spiral gas flow to reduce the forward velocity of the aerosol plume.

Another embodiment of a nebulizing catheter 592 is shown in FIGS. 36 and 37. This embodiment of the nebulizing catheter 592 can be used with a separate endotracheal tube (not shown). The nebulizing catheter 592 includes a main shaft 596 having a central lumen 600 and one or more additional lumens 604 located around the central lumen 600. In this embodiment, the central lumen 600 is used for the flow of a pressurized gas and the additional peripheral lumens 604 are used for the delivery of the liquid medicine. The lumens 600 and 604 terminate distally in orifices 608 and 612, respectively. Located at a distal end of the nebulizing catheter 592 and immediately adjacent the orifices 608 and 612 is a diffuser 616. In one embodiment, the diffuser 616 is composed of a generally disk-shaped body that is sized to deflect the flow of gas from the orifice 608 of the central lumen 600 past the liquid orifices 612 thereby nebulizing the liquid medicine. A small gap (or venturi area) 620 between the diffuser 616 and the distal end of the main shaft section 596 of the catheter 92 provides favorable flow characteristics for generating the aerosol. The diffuser 616 may be connected to a retaining wire 624 that is located in the central lumen 600. The retaining wire 624 may be used to secure the diffuser 616 to the distal end of the nebulizing catheter 592. Also, the retaining wire 624 may be used to pulse the generation of aerosol by reciprocation of the diffuser. It is noted that the aerosol produced by this embodiment has a substantially radial velocity component and may have only a small forward velocity component. In addition, a centering device, such as wings 625, may be attached to the diffuser 616.

FIG. 38 shows an alternative embodiment of the diffuser 616. In FIG. 38, the diffuser 616 is formed of a loop that has its ends located in two apertures in the nebulization catheter shaft tip and a middle portion directly in front of the distal gas orifice 608. The loop may be formed of a metal or polymer wire or other material. The loop could be formed by an extrusion method or molded.

Referring to FIG. 39, there is an alternative embodiment of the nebulization catheter system. A nebulization catheter 627 is located in an endotracheal tube 628.. The nebulization catheter 627 includes a coaxially arranged outer tube 629, a middle tube 630, and an inner tube 631. Liquid delivered through a lumen of the inner tube 631 is nebulized by pressurized gas delivered in the annular region 632 between the inner tube 631 and the middle tube 630. In addition, pressurized gas is also delivered from a secondary gas supply that communicates with the annular region 633 between the middle tube 630 and the outer tube 629. The secondary gas supply may be used to help provide the desired plume shape and velocity. For example, the secondary gas supply delivered from the outer tube 629 can be used to provide a coaxial sheath of air that helps minimize impaction of the nebulized aerosol on the walls of the trachea or other airway passage. Alternatively, the secondary air supply may be used to impart additional forward velocity to the aerosol plume. With the embodiment of FIG. 39, the additional air flow can be provided by the secondary gas supply via region 633.

In the embodiments discussed above, nebulization is provided at a distal tip of a catheter by directing a pressurized gas from a distal orifice across another distal orifice from which the liquid medicine is delivered. As shown in several of the embodiments above, one way to deliver the liquid from the distal orifice is via a lumen that extends through the catheter to a proximal end. This construction provides efficient operation for many types of medication delivery. In many cases, the distal liquid medicine orifice is subject to a negative pressure due to the pressurized gas flow across it. This negative pressure may in many applications be sufficient to draw the liquid out of the orifice in order to nebulize it. If pulsing of the aerosol is desired, the pressure of the gas lumen can be pulsed thereby resulting in pulsed generation of the aerosol. By increasing the gas pressure, it may be possible to also increase the aerosol output.

In other situations, it may be preferable to apply a positive pressure to the liquid, such as at the proximal end of the liquid lumen, in order to deliver liquid from the distal liquid orifice, it is necessary. This positive pressure applied to the liquid lumen may be the same as that applied to the gas lumen (e.g. 35–50 psi) or alternatively may be different (less than the gas lumen). If it is desired to pulse the nebulization of the liquid, this can be accomplished by applying pulses of pressure to the column of liquid via the proximal end of the liquid lumen or reservoir. It may also be preferred to synchronize the pressurization of the gas in the gas lumen with the pressurization of the liquid lumen. In addition to applying the positive pressure to the liquid lumen in pulses to generate a pulsed aerosol from the distal orifice, if it may be preferred in an alternative embodiment to apply a small negative pressure immediately after each positive pressure pulse in order to draw the liquid at the distal orifice back into the liquid lumen to thereby avoid drooling. In a preferred embodiment, the portion of the nebulization catheter in which the liquid lumen is formed may be composed of a relatively low compliance material to transmit pressure pulses to the distal end with minimum attenuation.

A full length liquid lumen may have disadvantages in certain situations. For example, pulsing of the liquid from the distal orifice may not correspond to or follow closely with the application of pressure to the proximal end due to attenuation of the pressure pulse over the length of the catheter. In addition, applying pressure to the proximal end of the liquid lumen in order to transmit pressure to discharge the liquid from a distal orifice requires that the lumen be filled with the liquid. In some situations, this is more medicine than would be required by the patient and might result in waste.

The embodiment in FIG. 40 addresses these concerns by controlling the pressurization of the liquid as close as possible to the distal liquid orifice, thereby reducing the effects of catheter compliance and attenuation. In FIG. 40, a nebulization catheter 652 has a main body 656 having a gas lumen 660 that extends from a proximal end (not shown) to a distal gas orifice 664. The main body 656 also includes a distal liquid medicine reservoir 668. In the embodiment shown in FIG. 40, the liquid reservoir 668 is located in a distal portion of the main shaft 656 of the catheter 652. The liquid reservoir 668 is preferably close to the distal tip of the nebulizing catheter 652. The liquid reservoir 668 is filled with the medicine to be delivered. If the amount of medicine is small in volume, the liquid reservoir may also be correspondingly small. This embodiment is especially suitable for the delivery of small volumes of medicine such as 0.1 to 0.5 ml, e.g. single use. The reservoir 668 may be pre-filled during the manufacturing stage of the catheter. The reservoir 668 may be formed by plugging a lumen of the catheter at a distal location. Alternatively, the liquid reservoir 668 may also extend back to the proximal end of the catheter, thereby forming a liquid lumen, and communicate with a proximal port as described with respect to the other embodiments discussed herein. This may be required if the lumen is made of a non-compliant material. In yet another alternative embodiment, the liquid reservoir may be formed in a balloon located externally of the catheter shaft 656.

A filter 672 and plug 676 occupy positions in the distal end of the liquid lumen/reservoir 668. A distal tubular extension 680 extends from the plug 676 and communicates with the liquid lumen/reservoir 668. The tubular extension 680 has a distal orifice 684 aligned with the distal gas orifice 664 so that a pressurized gas exiting the gas orifice 664 nebulizes the liquid exiting the liquid orifice 684. The distal liquid orifice may have a sealable cap or wax-like covering associated therewith that can be opened when the nebulization catheter is put into use. In a distal section of the main shaft 656 of the catheter 652, the gas lumen 660 and the liquid lumen 668 are separated by a flexible, distendable wall or membrane 688. In the embodiment of FIG. 40, pulsing of the aerosol is accomplished by pulsing of the gas pressure in the gas lumen 660. When the pressure in the gas lumen 660 is high, it causes the flexible wall 688 between the gas and liquids lumens 660 and 668 to distend into the liquid lumen 668. This is represented by the dashed line in FIG. 40. When this occurs, the pressure from the gas lumen 660 is transmitted to the liquid lumen 668 and liquid medicine is forced out the distal liquid orifice 684. When the pressure applied to the gas lumen 660 is low, the distendable wall 688 recovers its original position. It is noted that when the distendable wall 680 recovers its original position, it may cause a negative pressure at the distal liquid orifice 684 which may cause the liquid to withdraw slightly into the tubular extension 680 thereby reducing the occurrence of liquid drooling at the tip. In addition, it is noted that the delivery of liquid from the distal liquid orifice 680 may not occur immediately upon application of a high gas pressure to the gas orifice since it will take some time for the bladder 688 to distend. This means that gas will be flowing steadily at a high pressure from the distal gas orifice when the liquid begins to flow from the distal liquid orifice. This also may provide cleaner aerosol delivery and reduce the occurrence of drooling of liquid at the tip.

An alternative embodiment of the nebulization catheter 652 shown in FIG. 40 may be made using a flexible, but inelastic material for the bladder wall 688. If the bladder wall 688 were flexible, but inelastic, the pressurized gas passing past the liquid orifice 684 would create a negative pressure (venturi effect) thereby drawing out the liquid and nebulizing it. A continuous or preferably an intermittent gas supply to the venturi area would provide this negative pressure. The bladder wall may be provided with a vent to facilitate discharge.

In order to manufacture a nebulization catheter with compliant and non-compliant regions, as described above, the catheter may be co-extruded using different compounds or polymers to optimize the physical properties of the different wall sections. It may be preferred to use high energy radiation to crosslink the polymer material in the formation of the bladder wall.

V. Alignment of the Aerosol Plume

The embodiments described above are directed to developing an optimum nebulization plume. It is further recognized that another factor that contributes to the efficiency of the nebulization is the position of the nebulization catheter relative to the anatomical environment. For example, even if the nebulization catheter being used develops an optimal plume, the delivery efficiency of the catheter may be significantly impaired if the plume is directed into the wall of the endotracheal tube, the trachea or other airway passage. Accordingly, proper location, orientation, and alignment of the nebulization catheter in the anatomy can be an important factor contributing the delivery of medicine via a nebulization catheter. In general, it is preferable to align the catheter coaxially in the airway passage in which it is located.

It is also noted that an endotracheal tube, if present, can adversely effect delivery of aerosol from a separate nebulization catheter. For example, an endotracheal tube has an inner diameter that is smaller than the diameter of the trachea so that if the nebulization takes place inside the endotracheal tube, a portion of the aerosol may impact the inner wall of the endotracheal tube and thereby be wasted. Most conventional endotracheal tubes have a curved distal end that is relatively rigid so that when it is in place in the trachea of a patient, the distal end of the endotracheal tube is oriented off center. This can affect the orientation of a nebulization catheter located in the endotracheal tube causing it direct its aerosol into the trachea wall even if the nebulization catheter is positioned so that its distal end is located distally of the endotracheal tube. In general, it is desirable to allow the aerosol particles to avoid impaction for several centimeters after the aerosol is produced so that the aerosol particles can lose their velocity and become entrained in the inspiratory airflow.

Figure 41:
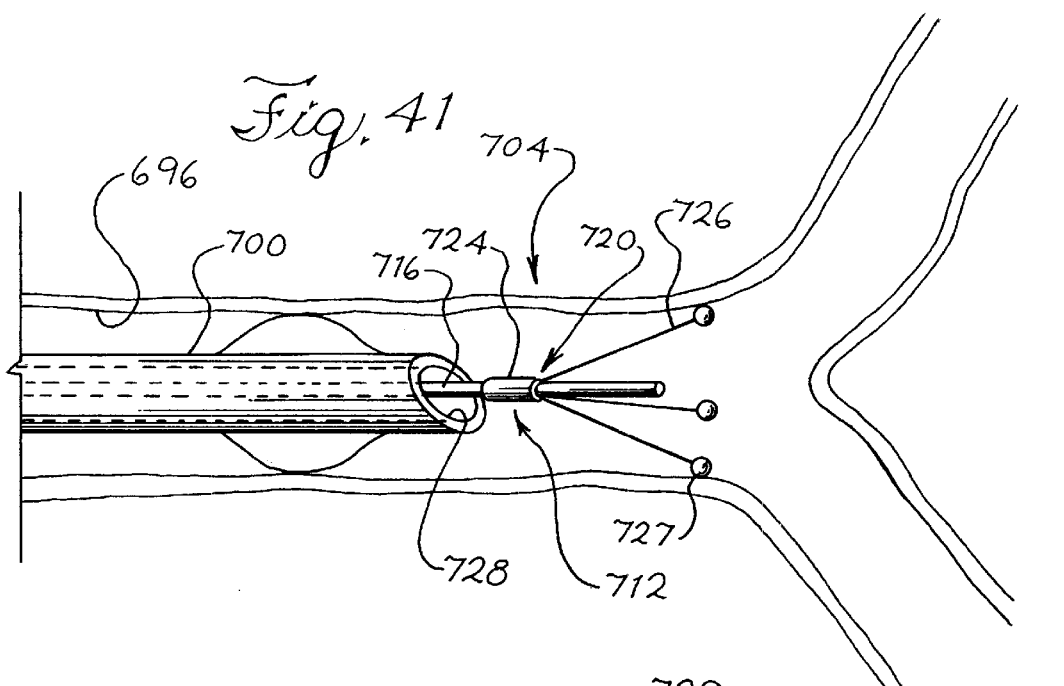
FIG. 41 is a perspective view of alternative embodiments of the nebulization catheter and endotracheal tube of FIG. 1 shown in a patient's trachea.

The embodiment of the invention in FIG. 41 is directed at providing improved alignment of a nebulization catheter in a patient's trachea. In FIG. 41, an endotracheal tube 700 is positioned in a trachea 704 of a patient. The endotracheal tube 700 is of a type that has an inflatable cuff 708 located around a distal exterior side to facilitate positioning and alignment of the endotracheal tube 700 in the trachea 696. Extending through and out of a distal end of the endotracheal tube 700 is a nebulization catheter 712. The nebulization catheter 712 may be similar to any of the embodiments of the nebulization catheter described above. Located around a distal portion 716 of the nebulization catheter 712 is a spring centering apparatus 720. The spring centering apparatus 720 includes a retainer ring 724 fixed to the shaft of the nebulization catheter 712 and a plurality of arms 728 connected to the ring 724. In one embodiment, there are three arms 726. The arms 726 are flexible and resilient. The arms 726 may be made of a spring tempered metal or a suitable plastic. Located at the end of each of the arms 726 opposite its connection to the ring 724 is a ball 727. The spring centering apparatus 720 is deployed by first positioning the nebulizing catheter 712 including the spring centering apparatus in the lumen 728 of the endotracheal tube 700. The arms 726 are formed so that they assume a size larger than the diameter of the trachea or airway passage. Accordingly, when the centering device is positioned in the endotracheal tube 700, the arms are resiliently deformed into a compressed configuration with the balls 727 close to the shaft of the nebulizing catheter 712. To deploy the centering device, the nebulizing catheter 712 is advanced out the distal end of the endotracheal tube 700. When the balls 727 are advanced out the endotracheal tube 700, they spring out to an expanded size and engage the walls of the trachea or other airway passage. The balls 727 provide a relatively smooth surface to limit irritation or injury to the trachea walls or other airway passage. With the arms expanded, the nebulizing catheter is centered in the trachea or other airway passage so that a plume discharged from a distal end of the nebulizing catheter has minimal contact with the walls of the trachea or other airway passage. When it is necessary to remove the nebulizing catheter 712, it can be withdrawn in a proximal direction back into the endotracheal tube 700. In a preferred embodiment, the arms are formed of a thin resilient wire or polymer, preferably less than approximately 0.015 inches in diameter. The arms and/or the balls may be made of, or coated with, a radiopaque material. It is an advantage of the embodiment of the centering device shown in FIG. 41 that it is located somewhat in advance of the distal end of the nebulization catheter. This positions the arms 726 of the centering device in the portion of the trachea or other airway passage into which the aerosol will be initially flowing. Thus, the centering device orients the distal tip of the nebulization catheter relative to the portion of the trachea or other airway passage beyond the distal tip thereby helping to reduce impaction along this portion.

Figure 42:
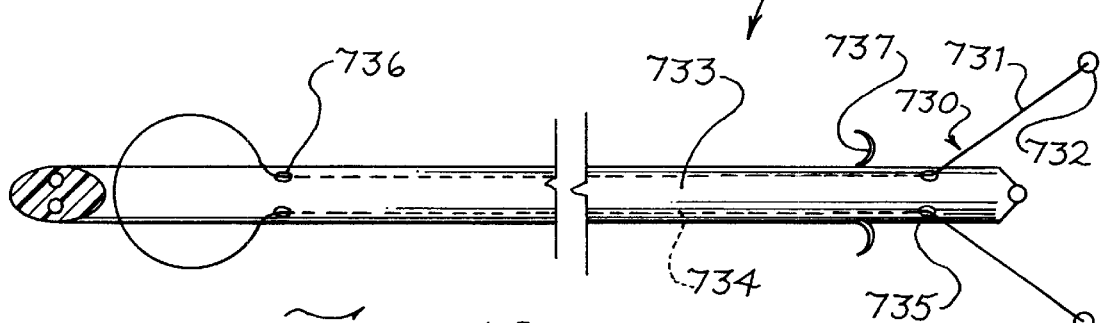
FIG. 42 is a side view of an another embodiment of the nebulization catheter of FIG. 1 showing an alternative centering device.

FIG. 42 shows an alternative embodiment of the nebulization catheter. A nebulization catheter 729 is used with an endotracheal tube as described above. The nebulization catheter 729 includes a centering device 730. The centering device 730 includes a plurality of arms 731 that are formed to resiliently extend outward from the axis of the catheter shaft to engage the wall of the patient's trachea or airway passage or the interior of an endotracheal tube depending upon the desired location of the distal end of the nebulization catheter. At the ends of each of the arms 731 are balls 732. The proximal ends of the arms 731 are formed of wires 733 that extend through lumens 734 in the shaft of the catheter 729. Each of the lumens 734 has a distal opening 735 from which an arm can extend. The distal openings are approximately 0.10–1 cm from the distal end of the catheter shaft. The proximal ends of the wires 733 exit the lumens 734 of the nebulization catheter via openings 736 that are close to the proximal end of the catheter in a portion of the catheter that would normally be outside the patient's body during use. Thus, the proximal ends of the wires 733 are accessible to the physician during use. By pulling and pushing on the proximal ends of the wires 733, the portion of the arms 731 that extend from the openings 735 can be adjusted. Thus, the arms 731 can be adjusted from a fully retracted to a fully advanced position by pulling or pushing on the proximal ends of the wires 733. In addition, since the proximal ends can of the wires 733 be adjusted in any intermediate position between the fully retracted and fully advanced positions, the physician can adjust the size of the centering device 730 to any appropriate size, as desired. Because the wires 733 should assume a desired shape when advanced out of the lumens in which they are contained during positioning, it is preferable that they be formed of a material that has shape memory properties so that the desired expanded shape can be imparted to the wires during manufacture. In one embodiment, the wires may be formed of nitinol.

In one preferred embodiment, a second centering device 737 is also provided. The second centering device 737 is located on the shaft of the nebulization catheter 729 proximally from the first centering device 730. The second centering device 737 may be formed of resilient wings formed of a material such as plastic or metal that extend radially outward from the shaft. The second (or proximal) centering device 737 helps keep the distal portion of the catheter 729 in alignment.

Figure 43:
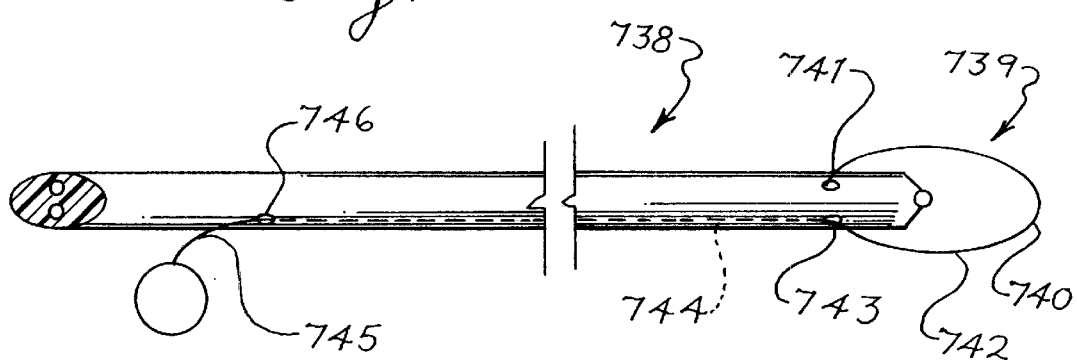
FIG. 43 is a side view of an another embodiment of the nebulization catheter of FIG. 1 showing another alternative centering device.

FIG. 43 shows another alternative embodiment of the present invention. A nebulizing catheter 738 is shown which may be similar to the catheter 20 of FIG. 1. The nebulizing catheter 738 includes a centering device 739. The centering device 739 includes a wire loop 740 located at a distal end of the catheter. One end 741 of the loop 740 connects to the distal end of the nebulizing catheter shaft. The other end 742 of the wire loop 740 enters an opening 743 in the shaft that communicates with a lumen 744 that extends to a proximal end of the catheter 738. A proximal end 745 of the wire exits the lumen 744 via an opening 746 in a proximal portion of the nebulizing catheter which is normally outside the patient's body during use. The size of the wire loop 740 can be adjusted by advancing or withdrawing the proximal end 745 of the wire. In this embodiment, it can be determined that the centering device is fully retracted when the wire 745 cannot be withdrawn any further. The position of the distal end of the nebulization catheter can also be determined by the resistance to further retraction caused when the loops or arms engage the distal end of the endotracheal tube. When in an expanded size, the wire loop 740 engages the walls of the trachea or airway passage or the interior of the endotracheal tube depending upon where the distal end of the nebulizing catheter is positioned. The size of the wire loop 740 can be adjusted from a fully reduced size to a fully expanded size as well as intermediate sizes. With the embodiment of FIG. 43, the size of the loop can be adjusted to different size airway passages in different patients or alternatively the size of the loops can be adjusted to different airway passages in the same patient if the physician desires relocating the nebulizing catheter to different locations in a patient's respiratory tract. In a one preferred embodiment, more than one wire loop may be provided at the distal end of the nebulizing catheter. It is noted that the wire loop 740 of this embodiment may also be used in for facilitating positioning over a guide wire in a manner similar to loop 106 shown in FIG. 9.

FIGS. 44 and 45 show another alternative embodiment of the present invention. A nebulizing catheter 747 has a shaft portion 748 and a wire loop 749 extending from a distal end of the shaft 748. In this embodiment, the wire loop 749 is connected at each end 750 and 751 to the distal end of the catheter shaft 748. A retractable sheath 752 is positioned over the nebulizing catheter shaft 748. The sheath 752 can be advanced and withdrawn relative to the catheter shaft 748. When it is desired to maneuver the nebulizing catheter into a desired position in the respiratory tract of a patient, the sheath 752 is advanced over the loop 749 to maintain a low profile, as shown in FIG. 45. When the distal end of the nebulizing catheter is suitably positioned, the sheath 752 is then retracted, as shown in FIG. 44, allowing the loop 749 to expand to its expanded size to center and align the distal end of the nebulizing catheter in the respiratory tract. In one embodiment, the loop 749 is formed of a superelastic material such as nitinol.

As noted above, proper positioning and alignment of the nebulization catheter can be an important factor affecting drug delivery efficiency. In general, it is preferable to position the tip of the nebulizing catheter as closely to the central region of the trachea (or other respiratory passage, such as the bronchi) as possible. It is further noted that even if the catheter can be centered relative to the trachea, if a section proximal to a centering device is misaligned, it can affect the directional orientation of the tip. This situation is represented in FIG. 46 in which a nebulizing catheter 753 is centered, but the tip is not properly aimed to provide an optimum plume. This potential problem can be overcome by using an embodiment of the invention shown in FIG. 47. In FIG. 47, a nebulizing catheter 754 is located in a trachea 755 of a patient. The nebulizing catheter 754 extends out the end of an endotracheal tube 756. A first centering apparatus 757 is located on a main shaft 760 of the nebulizing catheter 754 close to the distal end 764. The first centering device 757 may be similar to the centering devices shown in FIGS. 41–45. A second centering device 768 is located axially along the nebulizing catheter shaft 760 proximally from the first centering device 757. The second centering device 768 may be the same as the first centering device 757. As shown in FIG. 47, the two centering devices 757 and 768 not only serve to position the nebulization catheter 7754 centrally in the trachea, but also serve to align the nebulizing catheter tip to expel the plume along a central axis of the trachea.

The proximal centering device 768 may be substituted by another type of centering device or may employ the endotracheal tube 756 for this purpose, as shown in FIG. 48. If the endotracheal tube is used to assist in centering the nebulization catheter, it may incorporate a distal, elongated occlusion cuff 772 or balloon to coaxially align it accurately in the trachea. Most conventional endotracheal tubes are provided with a curvature to facilitate positioning the trachea of a patient. In addition, most conventional endotracheal tubes are relatively stiff. These factors may result in the misalignment of the distal end of the endotracheal tube relative to a patient's trachea as illustrated in FIGS. 46 and 47. In order to use the endotracheal tube for centering of the nebulization catheter, it is preferable to make the tip of the endotracheal tube straighter and/or more flexible than in conventional endotracheal tubes to ensure proper concentricity with the occlusion balloon and the trachea. An endotracheal tube with a straighter and more flexible tip is shown in FIG. 48. In addition, the endotracheal tube may be provided with a centering or aiming device 776 for aligning the nebulization catheter 754. In the embodiment of FIG. 48, the aiming device 776 is formed by a plurality of flexible or resilient wings the extend from the wall of the endotracheal tube 756 toward an axially central position.

Appropriate centering and aiming of the nebulization catheter can be affected by anatomical factors. It is noted that in some circumstances, it is preferable to position the distal tip of the nebulization catheter into either bronchus of the lungs or even into separate bronchia. Positioning of the nebulizing tip closer to the alveoli may enhance drug delivery efficiency. In a situation in which it is desired to place the nebulizer tip in both bronchi of the lungs, a nebulizing catheter 780 with dual tips can be employed, as shown in FIG. 49. When using a dual tip catheter such as shown in FIG. 49, centering and aiming can be important considerations because of the narrower air passages in each of the bronchi. To provide for centering and aiming of a dual tip nebulizing catheter, each of the tips 784 and 788 may be provided with its own centering apparatus, such as 792 and 796. These centering devices may be similar to the centering devices described above. Alternatively, the centering devices 792 and 796 may be formed of arms or struts, made of a flexible or resilient material, that bow out from the shafts of each of the tips 784 and 788, as shown. These struts may be formed with a shorter length in order to fit into smaller airway passages or alternatively they may be made to provide a range of deployment sizes to accommodate different airway passages.

As an alternative to providing a nebulizing catheter with dual tips 784 and 788 as shown in FIG. 49, if delivery of aerosolized medicine into separate branches of the lungs is desired, it may be preferred to use a nebulizing catheter with a single nozzle tip that has multiple orifices or jets aimed toward the desired branches.

With respect to all the centering devices described above, it is noted that some aerosol may impact the wires or loops that form the centering devices and accordingly, the centering devices are preferably constructed of wires or other materials having a small diameter or cross section to minimize losses due to such impaction. Moreover, the overall improved efficiency due to the reduction in aerosol impaction on the walls of the trachea or other airway passage is expected to more than compensate for amy losses due to impaction on the centering device.

Another alternative means for centering the distal end of a nebulization catheter in the air passage is to use part of the pressurized gas for a pneumatic centering device. Air jets generated from two or more outward directed orifices spaced evenly around the outer circumference of the nebulizing catheter near the tip can be used to center the catheter in the airway. This alternative may help avoid irritation and provide additional advantages compared to physical centering devices.

Another alternative way to help center the nebulizing catheter in the patient's airway passage is to use a balloon or wire centering device placed near the nebulizing catheter tip. The balloon or wire centering device can be temporarily inflated to double check the placement of the nebulizing catheter tip in relation to the endotracheal tube tip. To use this feature the nebulizing catheter is advanced beyond the endotracheal tube tip using markings on the proximal shaft to judge the distance. The centering device or balloon would then be expanded to a diameter larger than the endotracheal tube and the catheter retracted until the centering device or balloon could be felt engaging with the endotracheal tube tip or until the endotracheal airflow was obstructed.

VI. Operation and Flow Control

As mentioned above, the driving gas used to pressurize the gas lumen may be pure (e.g. 100%) oxygen at a pressure of 35–50 psi. Other gases and pressures may be used with suitable adjustments to provide for the desired particle size. The pressurized gas also may be humidified by a bubbler or other suitable means and warmed, if necessary.

Regarding the liquid lumen, one way to deliver the liquid drug through the nebulizing catheter is by a manually operated syringe. To delivery a liquid drug in this manner, a syringe containing the liquid medicine to be nebulized is connected to the liquid port on the manifold connected to a proximal end of the nebulizing catheter. Then, the liquid is injected while the pressuring gas is being supplied to the nebulizing catheter via the gas inlet port on the nebulizing catheter manifold. Using a manually operated syringe is reliable, easy to use, and may be preferred when it is desired to deliver only a small amount of medication.

In a preferred embodiment, the liquid drug is delivered to the nebulizing catheter from a pressurized source. A pressurized source for the liquid medicine can provide for a generally higher and more uniform pressure. A high pressure assists in clearing any blockages that may occlude the liquid lumen. Pressurization of the liquid lumen also can ensure that all the liquid drug is evacuated from the catheter tip. In addition, use of a liquid pressurization source can provide for drug delivery for a longer period of time or a drug delivery that is timed or pulsed to coincide with operation of a ventilator, if used. In a preferred embodiment, the same pressure source (at 50 psi) that is used to provide the gas pressurization can also be used to provide for pressurization of the liquid. Some ventilators have an auxiliary port that are used for externally located nebulizers. The pressure flow from this auxiliary port may be used as a pressure source to drive the liquid and gas supplies of the embodiments of the nebulizing catheter considered herein. Alternatively, a sensor located in the flow from this auxiliary port may be used to trigger another control device that operates the pressurized liquid and gas supplies.

In a preferred embodiment, the generation of the aerosol can be synchronized with the inhalation of the patient. In one embodiment, this can be accomplished with a manually operable control gas valve on the gas pressure line to the liquid input port. This may be suitable when the medicine can be delivered in a short period of time, e.g. a few respiratory cycles. Alternatively, when it is preferred to deliver the medicine for an extended period of time, it may be preferred to employ a system that can automatically deliver medicine via the nebulizer from a source of liquid medicine. In such a system, the gas and/or liquid flow are triggered by the patient's respiratory cycle with the use of an electronic pressure sensor and relay actuator.

Figure 50:
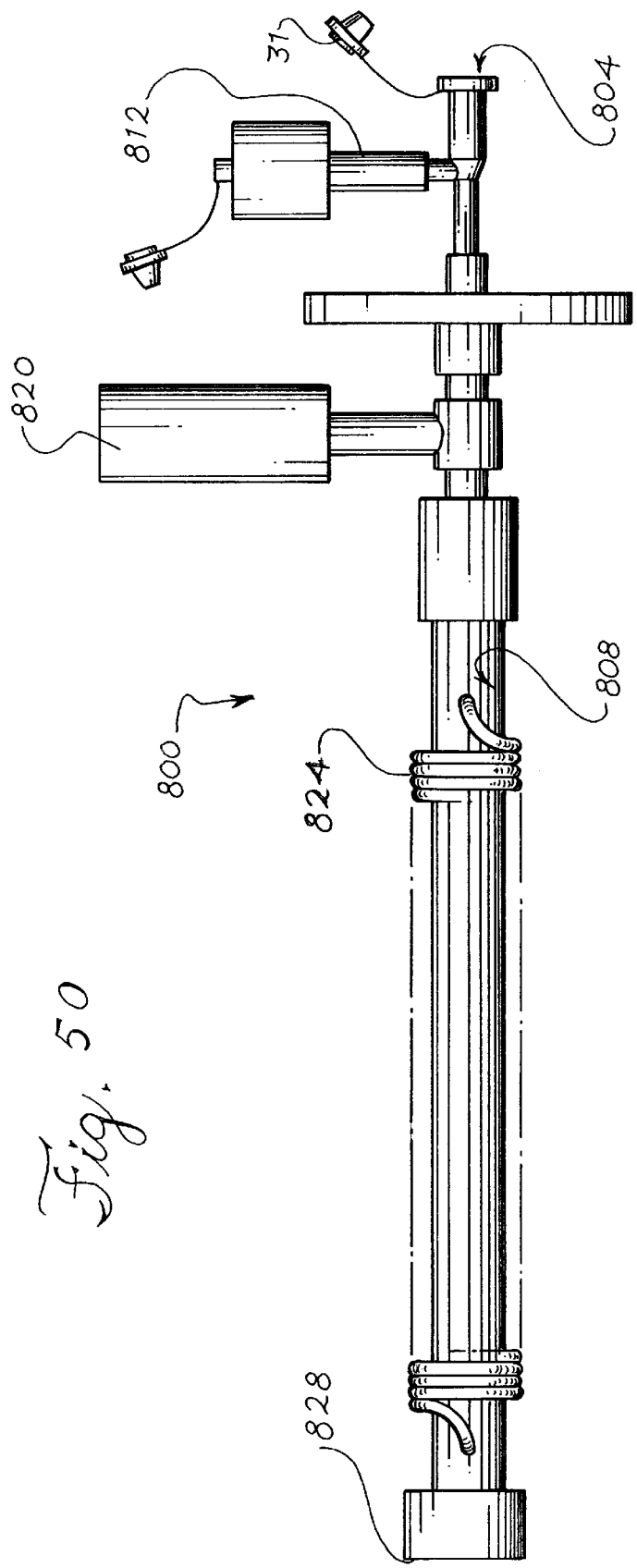
FIG. 50 is a diagram illustrating an embodiment of a drug reservoir and pressurization assembly that can be utilized in connection with the embodiment of the nebulization catheter of FIG. 1.
Figures 51, 52:
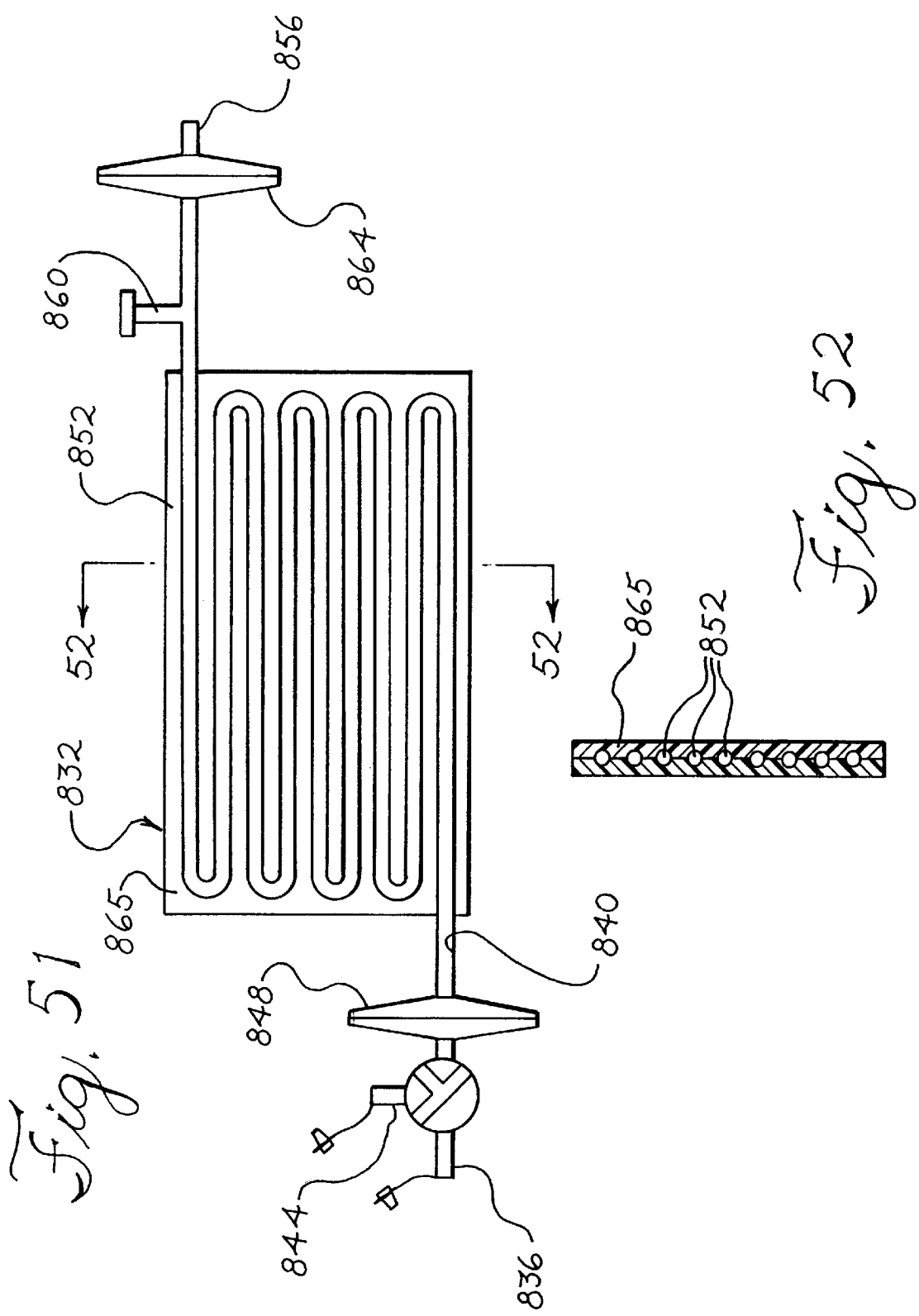
FIG. 51 is a diagram similar to that of FIG. 50 illustrating an alternative embodiment of the drug reservoir and pressurization assembly.
FIG. 52 is a sectional view along line c–c' of FIG. 51.

An important factor relating to effective delivery of medication via a nebulizing catheter is the flow control system for pressurizing and supplying the gas and liquid to the proximal end of the nebulization catheter. In many circumstances, it is envisioned that medication will be delivered to the patient via a nebulization catheter that is in place in the patient over an extended period of time, such as several hours or days. In such circumstances, it would be preferred to use a system that automatically delivers the proper dosage of medication from a supply of the medicine to the patient at the proper rate, and further that can operate automatically and unattended. Further, it would be preferred to provide a means to detect when the supply is running low so that either the nebulization catheter can be disconnected or a new supply provided. FIGS. 50 and 51 show several embodiments of a reservoir and pressurization system for use with a nebulizing catheter.

Referring to FIG. 50, a reservoir and pressurization assembly 800 is connected to a proximal end of a nebulization catheter. The nebulization catheter may be similar to any of the embodiments described above. The assembly 800 has a gas inlet port 804 that can connect to an external pressurized gas supply. The external pressurized gas supply may be the main gas supply of the hospital or may be provided by another unit. The external gas supply may provide oxygen at 50 psi. The gas inlet port 804 communicates with an airflow passageway 808 defined by and extending through the assembly 800. The assembly 800 includes a gas output port 812 that communicates with the fluid flow passageway 808 and which connects to a gas inlet port of the nebulization catheter (not shown). The gas output port 812 is located immediately downstream of the gas inlet port 804. Located in the fluid flow passageway 808 downstream of the gas outlet port 812 is a filter 816. The filter 816 is preferably a hydrophobic filter that allows the passage of gas but which would prevent the backflow of any liquid. Located downstream of the filter 816 in the fluid flow passageway 808 is an injection port and reservoir 820. This port 820 communicates with a supply of the liquid fluid medication to be supplied to the nebulizing catheter. Located next in the fluid flow passageway 808 is a capillary tube drug reservoir 824. The capillary tube reservoir 824 is comprised of a length of plastic tubing adapted to hold a supply of the liquid medication to be delivered. In the embodiment shown, the capillary tube reservoir consists of a helical coil of transparent tubing. Located downstream of the capillary tubing reservoir 824 is a liquid outlet 828 that connects to a liquid inlet port of the nebulization catheter (not shown). With the embodiment shown in FIG. 50, the transparent capillary tubing 824 provides a convenient and reliable way to ascertain the supply of medication to the nebulizing catheter. The capillary tubing because of its length is capable of containing a suitable supply of the medication. When the attending medical personnel observe that the medication is about to run out, a new supply can be readily provided. The clear capillary tube allows easy visualization of the drug flow by watching the gas-drug meniscus travel down the tube. Instead of relying on direct observation by medical personnel, the capillary tubing may be used with an automatic detection device, e.g. a photocell, that provides an alarm to the medical personnel upon detection that the medication is running out in the capillary tubing or that the meniscus has ceased moving due to a blockage. A blockage may also be detected by detection of an increase in pressure.

FIGS. 51 and 52 show another embodiment of a fluid reservoir and pressurization assembly 832. This embodiment includes a gas inlet 836, a fluid flow passageway 840, a liquid medicine supply vent 844, a filter 848, a capillary channel section 852, and an outlet port 856. In this embodiment, the filter 848 is located downstream of the filling vent 844. The filter 848 allows the pressurized gas to push the liquid drug during use but prevents the liquid drug from backing up to the vent during filling. In this embodiment, a second injection port 860 is provided downstream of the capillary section 852 and a second filter 864 is located downstream of the second injection port 860. The second filter 864 is preferably a filter having approximately a 20 μm retention. Also, in this embodiment, the capillary section 852 may be composed of a planar section 865. The planar section 865 may be a piece of plastic having a winding channel molded, routed or otherwise formed therein. The planar section 868 is preferably colored to provide suitable contrast with the liquid solution flowing therethrough. A transparent flat plastic cover is positioned over the winding channel of the planar section 865 to form the closed channel of the capillary section. The fluid channel in the capillary section preferably has an I.D. of approximately 2 mm. The second inlet port 864 provides an additional means to add medication to the nebulizing catheter liquid flow. When the capillary channel in the section 852 has been filled, the gas is used to pressurize the tube and force the fluid to the catheter tip. The second filter 864 acts as a restrictive orifice to precisely meter the flow to the nebulizing catheter. The clear capillary channel allows easy visualization of the drug flow by watching the gas-drug meniscus travel down the tube. The narrow tube makes the flow appear to move quickly even at slow delivery rates. Thus, any flow interruption can be easily observed. The capillary tubing section also ensures that almost 100% of the drug is delivered to the catheter tip since there is no dead space in the line except at the injection port 860.

Figure 53:
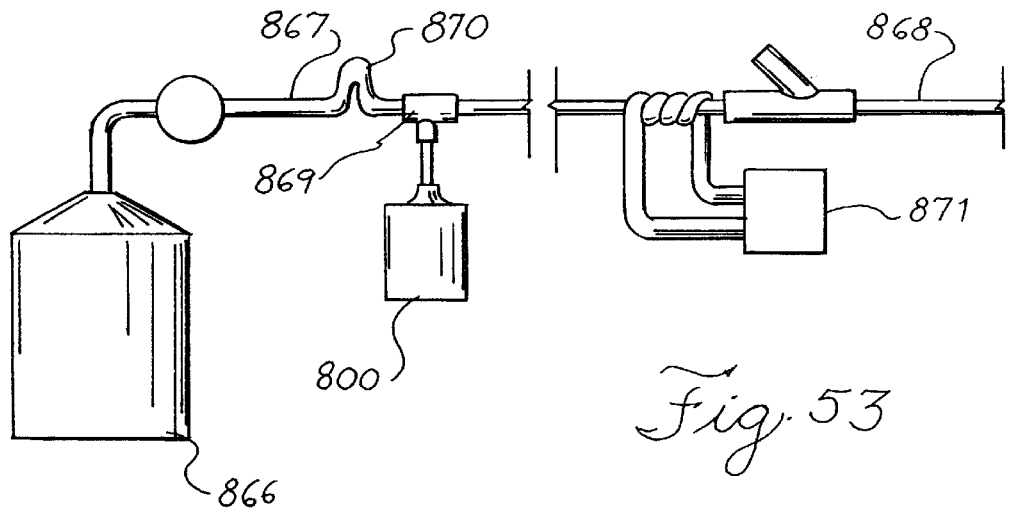
FIG. 53 is a side view of an alternative embodiment of FIG. 1 including an optional humidification and heating arrangement.

During ventilation of a patient with an endotracheal tube, especially when intubation that takes place for a long period of time, it is considered desirable to humidify the air being delivered. When a nebulization catheter is used for delivery of medicine, either in conjunction with an endotracheal tube or even without an endotracheal tube, it is possible to utilize the nebulization catheter for providing humidification in addition to medicine delivery. An embodiment of a flow delivery system for a nebulizing catheter incorporating humidification is shown in FIG. 53. A suitably large reservoir 866 holds sterile water or saline. The reservoir 866 is connected to the liquid supply lumen 867 of a nebulization catheter 868. Solution is drawn into the nebulization catheter 868 from the reservoir 866 by negative pressure at the catheter tip, gravity, a pump in the solution supply line distal of the reservoir, or by pressurizing the reservoir by a suitable means.

Figure 54:
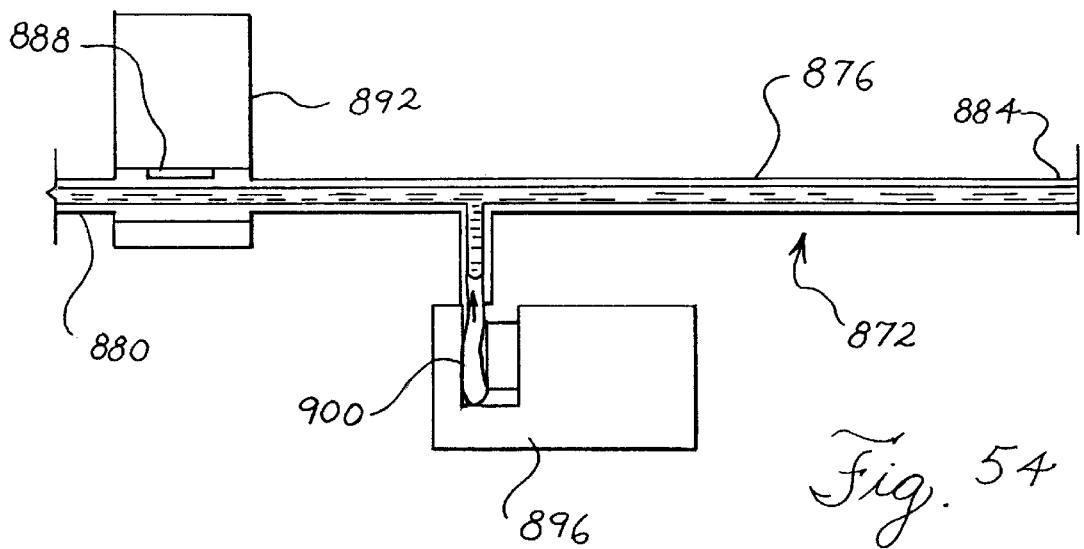
FIG. 54 is a side view of a flow control system used in connection with the embodiment of FIG. 1 used for pressuring the liquid flow lumen.
Figure 55:
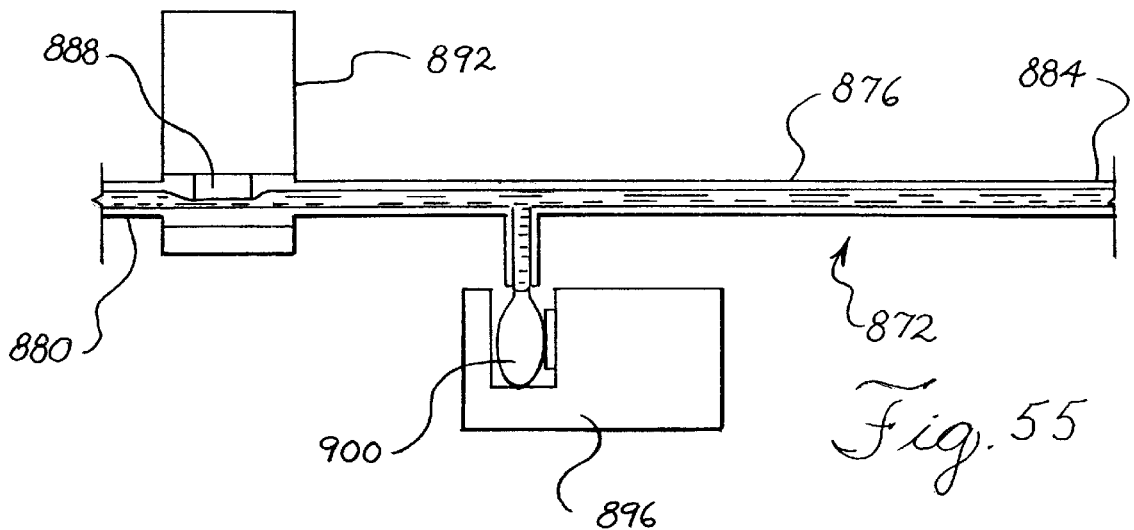
FIG. 55 is a view similar to that of FIG. 54 showing the flow control system of FIG. 54 in another stage of operation.

Medicine may be added to the humidification water in at the following ways. In a first alternative, the medicine is added to the isotonic saline in the solution reservoir 866 thereby providing for high dilution and slow, continuous delivery of the medicine along with the water. In second alternative, the medicine is introduced into the solution supply line 867 via an injection port 869 between the reservoir 866 and the liquid lumen of the catheter 868. The medicine may be delivered to the injection port of the solution supply line from a solution reservoir system such as system 800 of FIG. 50. Using this latter alternative, a more concentrated dose of the medicine can be delivered at the specific time preferred by the physician. It may also be preferable to include a molecular sieve, check valve or air trap 870 between the reservoir 866 and the injection port to the to ensure that the medicine cannot flow or diffuse backwards into the reservoir 866.

When delivering medicine to the lungs or when delivering water for humidification, it may be desired to heat the liquid prior to delivery. This may especially be appropriate since expanding gases which are associated with the nebulization of liquids may remove heat from the body. In order to address this concern, a heating element 871 may be associated with the liquid supply line 867 to the nebulizing catheter 868. This heating element 871 may include an electric coil wound around the supply line 867 or may use a heated water flow in a tubing wound around the supply line 867. The heating element 871 may be used in embodiments that provide for humidification as well as those that do not. Alternatively, the heating element 871 may be associated with the gas supply line or with the liquid reservoir 866, It is generally considered preferable to operate the nebulizing catheter so as to generate an aerosol that is carried by a patient's inhalation to the lungs. This requires a pulsing of the aerosol generation so that it is timed to coincide with the inhalation of the patient. If the patient is intubated, the timing of the nebulization can be synchronized with the operation of the ventilator. It is recognized that it may be preferable to begin the nebulization slightly in advance of, at, or slightly after, the beginning of the inhalation period in order to account for the distance between the nebulization tip and the alveoli. Also, it may be preferable to stop the nebulization slightly before the end of the inhalation period in order to avoid wasting aerosol after the inhalation flow has stopped.

This continuous pulsing of the aerosol can be accomplished by a system 872 as shown in FIGS. 54 and 55. FIGS. 54 and 55 show a portion of the flow control system for a nebulizing catheter. A flow line 876 has an inlet 880 and an outlet 884. The flow line 876 may be formed of a soft (e.g. compliant) tube. The inlet 880 connects to the source of liquid medicine and in particular may attach to the liquid outlet (828 or 856) of the liquid reservoirs shown in FIGS. 50–52. The flow line outlet 884 in FIGS. 54 and 55 connects to the liquid inlet port on the manifold of the nebulizing catheter, such as port 32 in FIGS. 1 and 2. Located around a portion of the flow line 876 is an actuator piston 888. The actuator piston 888 includes a solenoid pinch valve 892 that can impinge upon the portion of the liquid flow line 876 extending therethrough thereby pinching it off. The actuator piston 888 is connected to and operated by a controller that receives input from the ventilator (such as from the auxiliary port used for an external nebulizer) so that the actuator piston 888 is operated to open and close the flow line synchronous with the inhalation and exhalation phases of the ventilator. Instead of a solenoid piston, a metering valve or reversible syringe pump may be used.

In a preferred embodiment, the flow control system 872 uses a dual solenoid arrangement to provide a draw-back feature. Pulsing of the liquid flow by actuation of the actuator piston 888 may result in some liquid being left at the distal nebulizer liquid orifice when the pressure is turned off. This may result in small amounts of liquid drooling from the distal liquid orifice tip since the liquid is not being expelled under controlled pressure conditions. In order to limit the. occurrence of such drooling, a draw back feature is provided in the flow control system. The draw back feature is provided by a second solenoid 896 which is associated with a bladder 900 that communicates with the flow line 876. The bladder 900 communicates with the flow control line 876 downstream of the actuator piston 888. A small amount of fluid (liquid/air) occupies the bladder 900.

The bladder is composed of an elastic material that is formed with a tendency to recover to an expanded size. When the actuator piston 888 opens to allow the flow of fluid to the distal end of the nebulizing catheter, the second solenoid 896 moves to a closed position thereby compressing the bladder 900 and squeezing fluid out of it into the fluid flow line 876, as shown in FIG. 54. During the exhalation stage of the ventilation cycle, the actuator piston 888 closes to shut off the flow of fluid to the distal end of the nebulizing catheter. When the actuator piston 888 closes, the second solenoid 896 opens, as shown in FIG. 55. This allows the bladder 900 to resiliently recover to its expanded size, and when it does, it draws fluid into it from the fluid flow line 876. Because the fluid flow line 876 is closed proximally at the actuator piston 888, when the bladder draws fluid into it from the fluid flow line 876, it draws fluid from the distal end of the fluid flow line that connects to the nebulizing catheter liquid lumen. This causes the entire column of liquid in the liquid lumen of the nebulizing catheter to move slightly in a reverse direction (i.e. proximally) thereby moving the liquid away from the distal orifice. In this manner, the flow control system of FIGS. 54 and 55 allows the draw back of liquid in the flow line in a reverse direction during the exhalation phase of the ventilator when the liquid flow line is shut off.

VII. Selective Nebulization Therapy Delivery

When delivering medication with a nebulizing catheter, it may be desirable to deliver the medication to only one of the bronchi of the lungs and not the other or to only certain bronchia and not others. A reason for this type of selective therapy may be that only one area of the lungs requires medication. An embodiment of the invention shown in FIG. 56 facilitates selective delivery of a medication via a nebulizing catheter to only one bronchus. In FIG. 56, an endotracheal tube 904 is positioned in a trachea 908 of a patient. A nebulizing catheter 912 is positioned in the endotracheal tube 904. This nebulizing catheter 904 may be similar to the embodiments described above. This nebulizing catheter 904 may even be of the type that is non-removably incorporated into the endotracheal tube. A second catheter 916 extends distally of the endotracheal tube 904. The second catheter 916 may be positioned in the ventilation lumen 920 of the endotracheal tube 904. The second catheter 916 includes a lumen through which a low flow pressurized gas can be conveyed. A proximal end of the second catheter 916 extends out of the proximal end of the endotracheal tube 904 through a suitable fitting, such as the fitting described in U.S. Pat. No. 5,078,131 (Foley). A suitable source of pressurized gas is attached to a proximal end of the second catheter 916. This gas source may be the same gas source used for the pressurized gas lumen of the nebulization catheter 912. A distal end 928 of the second catheter 916 is positioned in the bronchus 932 other than the bronchus to which it is desired to deliver nebulized medication. Pressurized gas is delivered through the second catheter 916 out an orifice 936 in the distal end thereof. The delivery of pressurized gas out the distal end 936 of the second catheter 916 causes the pressure level in the bronchus 932 to be slightly greater than in the other bronchus. Accordingly, when the nebulizing catheter 912 generates an aerosol of liquid medicine, it will tend to flow with the inhalation stream from the endotracheal tube 904 to the bronchus other than the one with the second catheter 916. In this manner, one of the bronchi of the lungs, or even selected bronchia, can be selectively medicated using a single nebulization catheter positioned in the endotracheal tube.

VIII. Timing of Nebulization

As mentioned before, in order to deliver the nebulized medicine to the lungs, it is preferred that the medicine is carried by the inhalation of the patient. A number of factors affect the efficiency of the medicine delivered this way. The following embodiments are directed to improving drug delivery efficiency taking into account some of these factors.

If the patient is intubated, it may be possible to synchronize the timing of the nebulization pulse with the patient's ventilation. In one embodiment, this may be accomplished by providing an interface between the ventilator and the nebulizer. In some circumstances it may be preferred to provide other means for triggering the nebulization. For example, the ventilator being used may not provide a suitable interface. Also, the ventilator may not provide sufficiently accurate information concerning the patient's respiration to enable the nebulization catheter to operate with highest efficiency. In such situations, it may be preferred to utilize one or more separate sensors to obtain information that can be used to trigger and operate the nebulization catheter.

Referring to FIG. 57, there is a nebulizing catheter 944 positioned in an endotracheal tube 948 located in the trachea 952 of a patient. A proximal end of the endotracheal tube 948 is connected to a ventilator 956. In order to obtain physiological information concerning the patient's respiration for use in timing the generation of nebulization pulses by the nebulization catheter 944, one or more sensors may be used. For example, a first sensor 960 may be located on a distal end of the endotracheal tube 948. In addition, a sensor 964 may be positioned on the nebulization catheter 944. Another sensor 968 may be positioned on a separate device, such as a separate catheter 972 which is located further distally in the respiratory system. In addition, a sensor 976 may be positioned in the ventilator circuit of the ventilator 956 or in a ventilator auxiliary port, if available, or elsewhere on the patient. These sensors 960, 964, 968, and 976 may be types of sensors that measure pressure, flow or a physiological parameter of the patient, such as muscle contraction, electophysiological activity, etc. In alternative embodiments, one or more of these sensors may be used.

FIGS. 58 and 59 show alternative embodiments of nebulization catheters that incorporate sensors. In FIG. 58, a nebulization catheter 980 is shown. This nebulization catheter 980 may be similar to the nebulization catheter in FIG. 11. In FIG. 58, a main shaft 984 includes a plurality of lumens with a centrally located lumen 988 used to deliver a liquid medicine and a plurality of lumens 992 located peripherally around it used to deliver a pressurized gas. One of the peripheral lumens 996 is not used for pressurized gas delivery, but instead is used for sensing purposes. This may be accomplished by forming an aperture 1000 through a wall of the main shaft 984. The aperture communicates with the sensing lumen 996. The aperture 1000 may be open or may be covered with a flexible diaphragm that permits transmission of pressure across it. A pressure sensing device may be located at a proximal end of the nebulizing catheter. The pressure at the distal end of the nebulizing catheter can be sensed by the proximally located sensing device via the sensing lumen 996. This could rely on pneumatic sensing of the distal air pressure. Because of the effect of the distal gas pressurization orifice, pressure sensing through the sensing lumen 996 may be used for purposes of gross overpressure for safety purposes. Alternatively, the pressure sensing lumen 996 may be used during periods of time when a pressurizing gas is not being delivered to sense the patient's physiological airway pressure.

FIG. 59 shows another embodiment of a pressure sensing nebulization catheter. This embodiment is similar to the embodiment of FIG. 58 except that a sensor 1004 is located at a distal end of the catheter 980, specifically in the aperture 1000. In this embodiment, the sensor 1004 is a pressure transducer. Wire leads 1008 extend proximally from the sensor 1004 via the lumen 996. Instead of measuring pressure, the sensor 1004 could measure the flow at the distal end of the catheter. This may be accomplished by piezoelectric, optical, Hall effect, or other types of sensor technologies. The sensor may also be of a fiber optic type.

Figure 58:
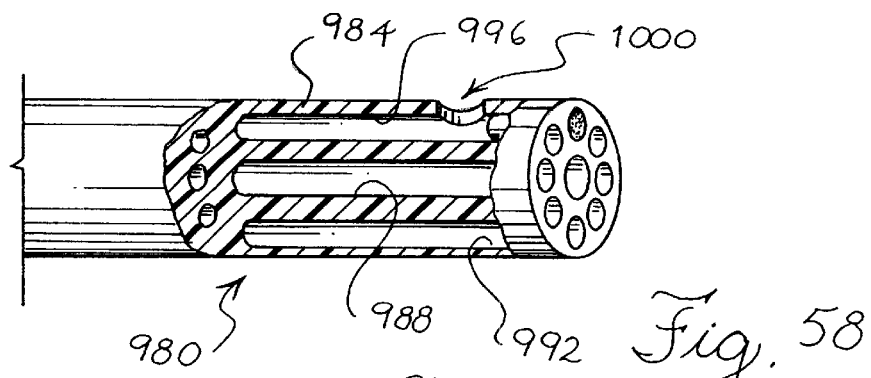
FIG. 58 shows a sectional view of an embodiment of a nebulizing catheter including a sensor.
Figure 59:
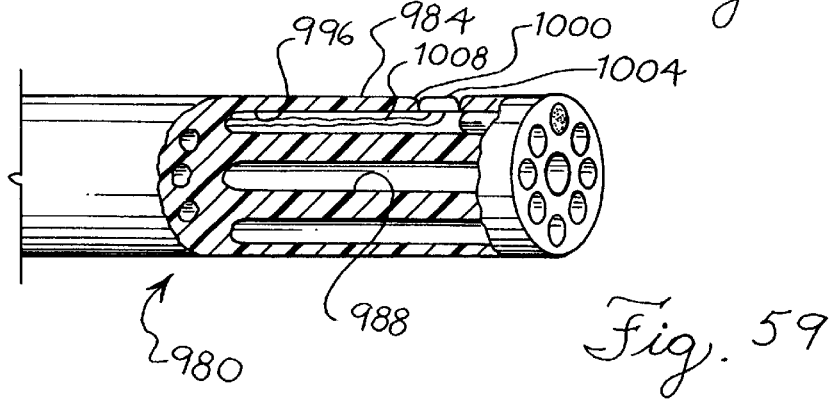
FIG. 59 shows an alternative embodiment of the nebulizing catheter shown in FIG. 58.

Although the embodiments of FIGS. 58 and 59 show sensing apparatuses associated with a nebulization catheter, these same types of sensors could also be used in the endotracheal tube 948, the separate catheter 972, or the ventilator 956 of FIG. 57 or the ventilator circuit.

The sensor outputs information to a controller 1012 that operates the flow control portion 1013 of the nebulization catheter system. The flow control portion may include the flow control assembly 872 (shown in FIG. 55) as well as include the control functions for gas pressurization. The controller 1012 may have preset triggering parameters or may be user adjustable. The controller 1012 may use airway flow, pressure, or physiological activity as a basis for controlling the flow control assembly 1013. The controller 1012 may provide for pulsing based upon any one of the following modes: (1) a controlled volume (bolus) of medicine is delivered with each pulse; (2) medicine is delivered until a physiological condition is sensed, e.g. exhalation; or (3) medicine is delivered for a fixable time interval, e.g. 2 seconds. These modes of operation may be selectable by the physician based upon the preferred treatment taking into account the patient's condition, the type of medicine being delivered, etc.

It may also be desired to regulate the delivery of aerosol so that it is not delivered with every inhalation. As mentioned above, one concern with delivery of an expanding gas is the cooling effect that it may have on the body. This can be a factor with high gas flow rates. Accordingly, it may be preferable to deliver aerosol on every other inhalation or every third inhalation, and so on. Alternatively, it may be preferred to deliver aerosol for certain periods of time, e.g. 5 minutes every hour. Therefore, by alternating aerosol delivery, the cooling effect associated with it can be reduced.

IX. Alternative Embodiments

A. Nebulizing Catheter Incorporated in Endotracheal Tube

The various embodiments of nebulizing catheters, disclosed above, have been described as being either adapted for use in conjunction with a separate endotracheal tube, or adapted to be used without an endotracheal tube. If used with an endotracheal tube, the embodiments of the nebulizing catheter disclosed above are preferably removable from the endotracheal tube if one is present. It is noted that many of the embodiments of the present invention disclosed herein may also be used in conjunction with a nebulization catheter that is non-removable from an endotracheal tube, i.e. in which the nebulization catheter is incorporated into and forms part of the endotracheal tube. An endotracheal tube that provides for nebulized medication delivery is described in a patent application filed by Dr. Neil R. MacIntyre on Mar. 10, 1992 entitled "Endotracheal Tube Adapted for Aerosol Generation at Distal End Thereof", the entire disclosure of which is incorporated herein by reference. According to a system developed by Dr. MacIntyre, there is provided an endotracheal tube that provides for nebulization of a medication at a distal end thereof. According to Dr. MacIntryre's system, an endotracheal tube includes two additional, separate lumens, in addition to its main ventilation lumen used for the patient's breathing airflow. A medication in a liquid form is conveyed through one of the additional lumens and a pressurized gas is conveyed through the other lumen. The two additional lumens have distal openings near the distal end of the endotracheal tube airflow lumen. The distal opening of the pressurized gas lumen directs the pressurized gas across the distal medication lumen opening thereby nebulizing the liquid medication so that it can be delivered to the patient's lungs. It is intended that the present invention covers embodiments of nebulization catheters that are non-removable relative to an endotracheal tube.

B. Aerosol Generation with Porous Material

Figure 60:
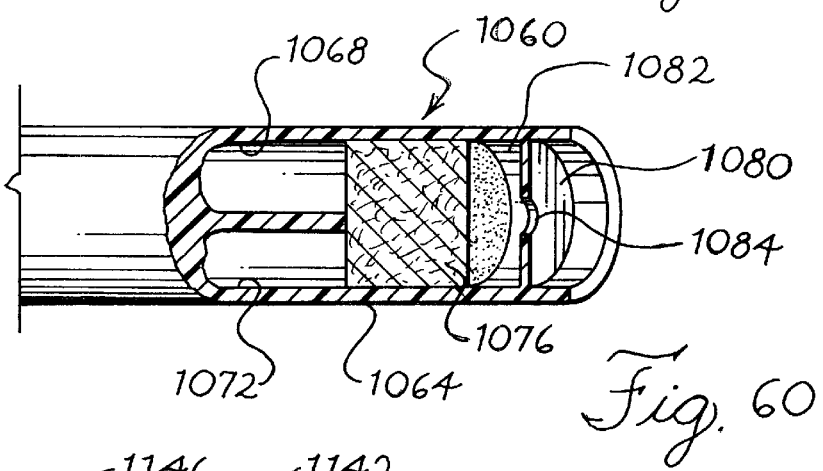
FIG. 60 is a sectional view of a distal end of an alternative embodiment of the nebulizing catheter of FIG. 1.

FIG. 60 shows another catheter 1060 for producing an aerosol. The catheter 1060 generates an aerosol, or aerosol-like plume by use of a porous material or sponge located in a lumen of the catheter. The catheter 1060 has a main shaft 1064 with a lumen 1068 through which liquid medicine is conveyed under pressure and a lumen 1072 through which a gas is conveyed under pressure. A porous material 1076 is located in a distal end of the shaft 1064 so that both lumens 1068 and 1072 convey their contents into the porous material 1076. The porous material 1076 may be a porous polyethylene made by Porex. Alternatively, the porous material may be a polymer sponge or other polymer material. Located in the main shaft 1064 distal of the porous 1076 is an end cap 1080 with an orifice 1084 located therein. The orifice is small and maintains a positive back pressure in the catheter shaft and porous material area. The end cap 1080 is separated from the distal side of the porous material 1076 by a small gap 1082. The liquid and gas delivered under pressure to the porous material 1076 migrate through the porous across the gap 1082 toward the aperture 1084. The liquid and gas become intermixed under pressure and as they are expelled from the fine tip orifice the gas expands and disperses the liquid particles into fine droplets. Upon discharging through the aperture 1084, the medicine forms tiny droplets, e.g. an aerosol. The aerosol is conveyed to the lungs of the patient in a manner similar to that described in the embodiments above. An advantage of using a porous material or sponge at the distal liquid orifice is that it reduces drooling of the liquid.

C. Secondary Aerosol Generation

In some situations it may be desirable to modify the primary aerosol spray generated by a nebulization catheter. One way that this can be accomplished is by causing the primary aerosol spray to impact upon a baffle placed in its path, the velocity and direction of the spray can be altered and the size of the distribution of the aerosol can be modified creating a secondary aerosol. Impaction upon a properly located baffle can break up large aerosol particles creating a finer aerosol mist. The baffle also deflects or diffuses the airstream carrying the particles reducing their forward velocity and altering their direction. This can lessen impaction on the carina or airways and enhance the entrainment of the particles into the inspiratory flow. Embodiments of nebulizing catheters incorporating an impaction baffle to provide a secondary aerosol are shown in FIGS. 61–64.

Figure 61:
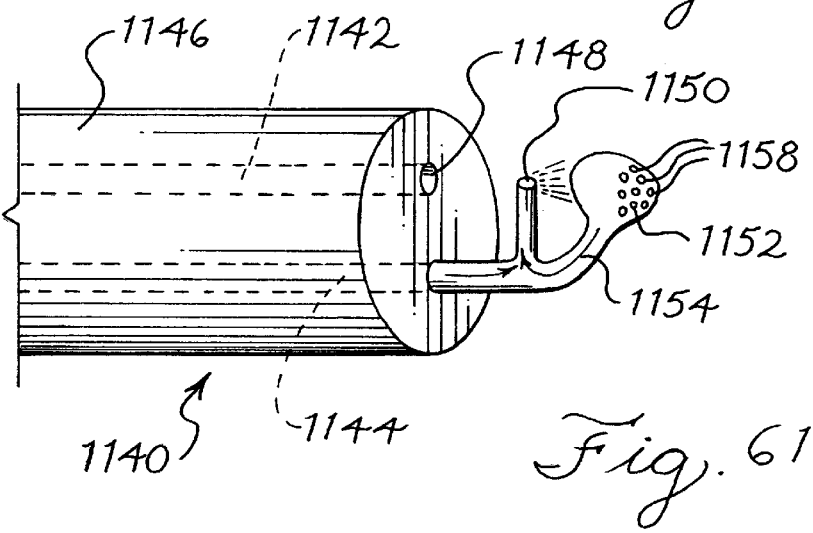
FIG. 61 is a sectional view of an embodiment of the present invention that incorporates a baffle to generate a secondary aerosol.
Figure 66:
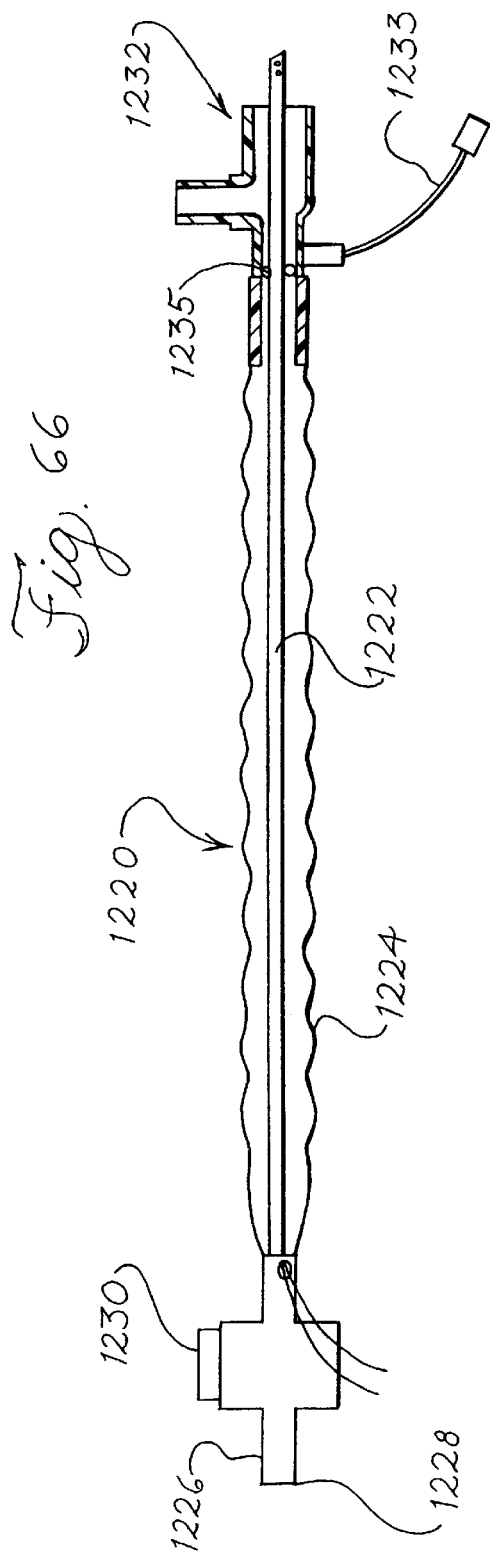
Figure 67:
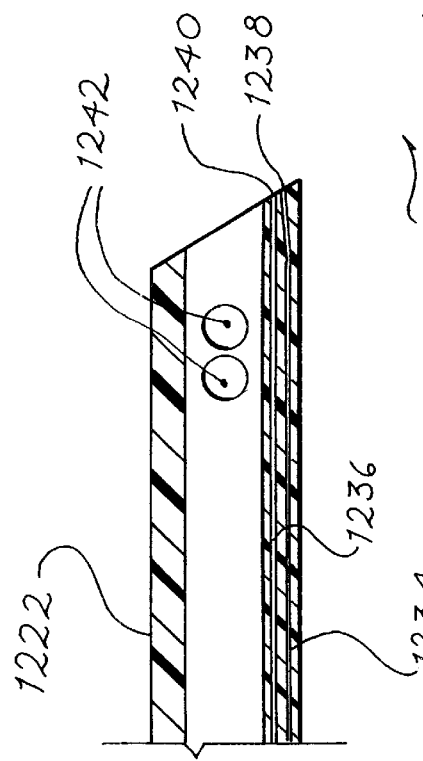

Referring to FIG. 61, a nebulization catheter 1140 has a gas lumen 1142 and a liquid lumen 1144 located in a shaft 1146 of the catheter. The gas lumen 1142 conveys a pressurized gas to a distal gas orifice 1148 and the liquid lumen 1144 conveys liquid to a distal liquid orifice 1150. A baffle 1152 connects to a baffle extension tube 1154 so that the baffle 1152 is located distally of the liquid orifice 1150. The baffle 1152 is preferably located as close to the solution orifice 1150 as possible without interfering with the generation of the primary aerosol.

Some of the primary aerosol that is not broken into fine particles may remain on the baffle 1152 and build up over time forming a thin liquid film on the surface of the baffle 1152. If this film is left to build up, it will form droplets that either fall or are blown off the baffle. These droplets may become quite large and of little or no therapeutic value representing a waste of the solution.

In order to recirculate this film of solution, the baffle 1152 may be used to collect and return the liquid solution to a liquid supply lumen 1144 To achieve this, the baffle may have with one or more orifices 1158 or porous material on its surface of the baffle 1152 for the collection of the film of solution. The orifices 1158 drain into or through the baffle, and are in fluid communication with the solution supply lumen 1144 via a lumen located inside of the extension tube 1154. The lumen inside the extension tube 1154 may communicate directly with the solution lumen 1144 or extension thereof.

In the embodiment of FIG. 61, the negative pressure generated at the nebulization orifice 1150 by the gas flow over it is used to draw the recirculated solution from the baffle recirculation orifice 1158 via the lumen in the extension 1154 and out the liquid orifice 1150 again. In this case, the recirculation orifices 1158 or surface should be in an area of higher ambient pressure than the solution orifice 1150 to cause the recirculation of the fluid. This may be accomplished by locating the collection orifices 1158 on a distal side of the baffle 1152 opposite the solution and gas orifices 1150 and 1148. The flow of new solution (from the proximally located solution reservoir) pumped into the solution lumen 1144 should be less than the flow drawn from the solution orifice 1150 to ensure that least some of the solution from the baffle 1152 is recirculated to the orifice 1150.

FIG. 62 shows another embodiment of a nebulization catheter that incorporates a baffle for the purpose of generating a secondary aerosol. This embodiment is similar to the nebulization catheter in FIG. 61 with the exception that the recirculated fluid is drawn back into a recirculation lumen 1160 in the catheter shaft 1146. The recirculation lumen 1160 communicates with the liquid lumen 1144 at a junction 1162 at which location the recirculated solution is mixed with newly supplied liquid in the solution lumen 1144.

FIG. 63 shows another alternative embodiment. This embodiment is similar to the embodiment of FIG. 62 except that the recirculated solution is routed from the baffle 1152 to the recirculation lumen 1160 and then to a separate solution orifice for re-nebulization. This dedicated solution orifice 1161 is also located at the catheter tip near a gas orifice 1148 to produce nebulization. The aerosol generated from this separate orifice 1161 is directed into the common baffle 1158 to break it into smaller particles and a portion of the solution will again remain on the baffle and be recirculated. This approach can eliminate the difficulties of balancing the flow of new and recirculated solution to a single solution orifice.

Referring to FIG. 64, there is another embodiment of a nebulizing catheter incorporating a baffle for the generation of a secondary aerosol. In this embodiment, a nebulizing catheter 1170 has a shaft 1172 with a liquid lumen 1174 connected to a liquid supply 1176. A gas lumen 1178 connects to a pressured gas source 1180. The liquid lumen 1174 communicates with a distal liquid orifice 1182 and the gas lumen communicates with a distal gas orifice 1184. A baffle 1186 is located in front of the liquid orifice 1182. Aerosol impacting on the baffle 1186 produces a secondary aerosol that flows around the baffle 1186. A residue film of liquid migrates around the baffle 1186 and enters into baffle orifices 1190 located on the distal side of the baffle 1186. The baffle orifices 1190 communicate with a recirculation lumen 1192 that extends through the catheter shaft to a reservoir 1194 located outside of the body where the recirculated solution is combined with non-recirculated solution pumped from a proximal drug reservoir. The flow of recirculated and non-recirculated solution into the system should be carefully balanced to match the amount of aerosol generated. To achieve this, flow metering and pumping strategies can be employed.

D. Nebulization Catheter with Pressurized Propellant-Drug Canister

In the embodiments described above, medicine is delivered in liquid form to the distal liquid orifice. In another embodiment, illustrated in the diagram of FIG. 65, the medicine may be mixed with a propellant and maintained under pressure and delivered under pressure to the distal tip of a nebulizing catheter 1198. A pressured medicine-liquid propellant mixture could be supplied from a pressurized canister 1200 such as those used as a component of a metered or non-metered dose inhaler. By using a propellant, an aerosol could be generated from the distal end 1202 of the catheter even without the addition of the pressurized nebulizing gas. However, the delivery of pressurized gas 1204 from the distal end of the nebulization catheter would be used to assist in breaking up any larger medicine particles and also assist dispersing the aerosolized drug solution delivered through the catheter as well as help shape the aerosol plume. For example, the delivery of the pressurized, nebulizing gas may assist in shielding the aerosol generated by the medicine-liquid propellant mixture and help avoid losses due to impaction.

E. Nebulizing Function Incorporated in Suction Catheter

As mentioned above, the nebulizing catheter can be incorporated into another device, such as an endotracheal tube, either removably or non-removably. Another such device into which a nebulizing catheter can be adapted is a suction or aspiration catheter. A suction catheter is sometimes used in conjunction with patients who are intubated. A suction catheter has an O.D. and a length such that it can be inserted through the ventilation lumen of an endotracheal tube. The suction catheter is used to aspirate fluids and mucin secretions that collect in the respiratory tract of in the endotracheal tube of a patient who is intubated. A conventional suction catheter is inserted down the ventilation lumen of the endotracheal tube and out the distal end. A mucolytic agent may be instilled as a liquid via a lumen of the suction catheter to help in the withdrawal of mucin from the trachea or bronchi. The suction catheter may then be withdrawn from the endotracheal tube and either disposed or retained in a sterile sheath connected to a proximal end of the endotracheal tube so that it can be reinserted into the endotracheal tube again.

A nebulizing catheter can be incorporated into a suction catheter so that a single device can perform both the functions of aspiration and nebulization for aerosol delivery. In an alternative embodiment of the present invention, the nebulizing catheter, such as described above, could be incorporated into a suction catheter so that a single catheter can provide both functions. This could be accomplished by provided any of the embodiments of the nebulization catheter described above with a separate lumen for the purpose of providing a suction to withdraw fluid from a patient's respiratory tract. Combining the functions of a suction catheter and nebulization catheter into a single device has the advantages of avoiding the expense of separate products as well as avoiding the inconvenience of inserting and withdrawing separate devices.

Embodiments of a suction catheter combined with a nebulization catheter are shown catheter is FIGS. 66–73.

FIGS. 66–70 show a suction catheter assembly 1220. The suction catheter assembly 1220 includes a suction catheter shaft 1222 slidably located inside of a flexible sheath 1224. A suction lumen 1225 extends through the suction catheter shaft 1222. A proximal manifold 1226 includes a port 1228 for connecting a vacuum source to the suction catheter lumen 1225. A valve 1230 operates to open and close the port 1228. A distal sleeve 1232 provides for connecting to an endotracheal tube such that the suction catheter shaft 1222 can be inserted into the endotracheal tube by pushing the proximal manifold 1226 toward the distal sleeve 1232. The distal sleeve 1232 may include a manifold for connection to a flush port 1233. A seal 1235 located in the sleeve 1232 closely bears on the suction catheter shaft to remove mucous or other unwanted materials that can be removed via the flush port 1233. The shaft of the suction catheter may be provided with a low friction, e.g. hydrophilic, coating to reduce adhesion of mucous.

The suction catheter assembly 1220 includes two additional lumens 1234 and 1236. These lumens 1234 and 1236 are located in a wall of the suction catheter shaft 1222. These lumens 1234 and 1236 communicate with distal orifices 1238 and 1240 located at a distal end of the suction catheter shaft 1222. These lumens 1234 and 1236 are used to deliver a liquid medicine and a pressurized gas for nebulizing the liquid medicine, as described above. Also located at a distal end of the suction catheter shaft 1222 are suction openings 1242.

The suction catheter assembly 1220 can be used in a conventional manner to remove mucin from the trachea and from the bronchi. The suction catheter assembly 1220 can also be used to deliver medicines to the lungs as an aerosol by means of the nebulizing lumens 1234 and 1236. The nebulizing lumens can also be used to deliver mucolytic agents as an aerosol. Because the fine aerosol delivered by the nebulizing lumens can be carried by a patient's inspiratory airflow into the bronchi, the mucolytic agent can be delivered further into bronchi compared to a suction catheter that merely instills or generates a coarse spray of a mucolytic agent. In addition, the flow velocity produced by the gas pressurization lumen may be used to assist in breaking up mucous at the end of the suction catheter.

Figure 68:
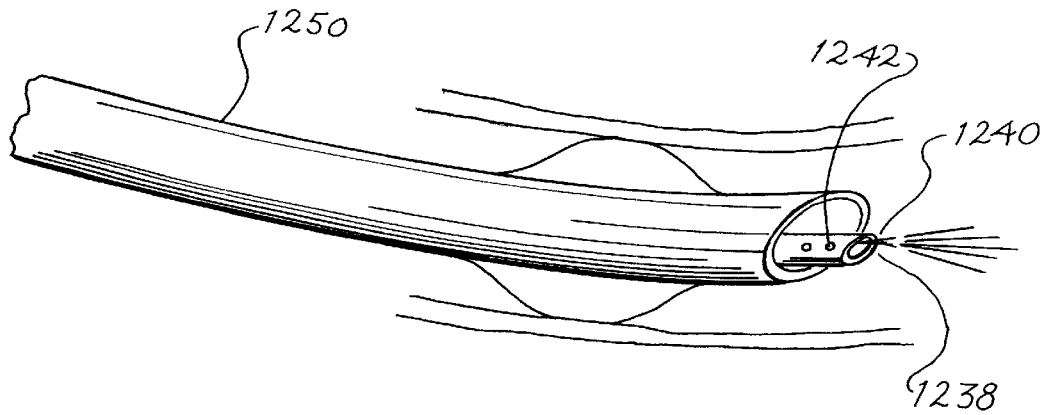
Figure 69:
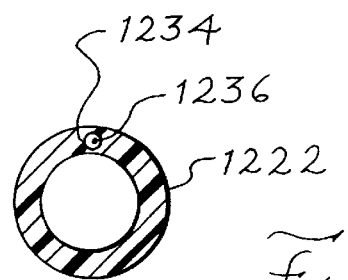
Figure 70:
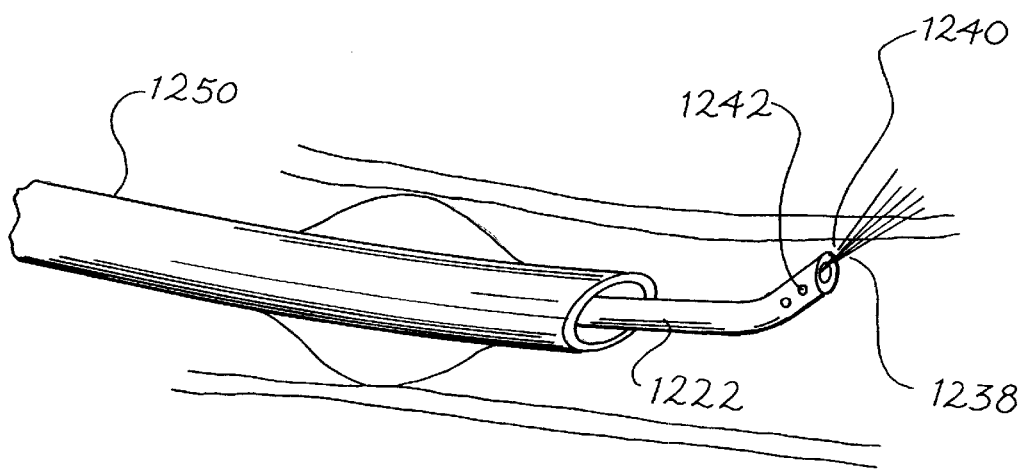

When using the suction catheter assembly 1220, it can be positioned so that a distal end of the suction catheter shaft 1222 is close to the distal end of the endotracheal tube 1250 as shown in FIG. 68 or alternatively the suction catheter shaft 1222 can be positioned so that it extends past the distal end of the endotracheal tube 1250 as shown in FIG. 70. As shown in FIG. 70, the suction catheter shaft 1220 may be formed with a distal curvature so that the distal end can be brought into proximity with the tracheal wall.

Rather than incorporate the nebulizing lumens into the wall of the suction catheter, it may be preferably in many situations to use a conventional suction catheter with a stand-alone nebulizing catheter. The stand-alone nebulizing catheter may be similar to any of the embodiments described above. A suction catheter and a nebulizing catheter can readily be used together with the alternative versions of the manifolds shown in FIGS. 71–73.

Referring to FIG. 71, an endotracheal tube 1252 has a proximal end with a single port 1254. A suction catheter 1256 has a distal manifold 1258. The distal manifold 1256 could be formed as part of the suction catheter 1256 or could be provided as a separate component. The suction catheter manifold 1258 connects to the single port 1254 of the endotracheal tube 1252. The manifold 1258 has a first port 1260 for connecting to a ventilator and a second port 1264 for connecting to a proximal end of a nebulizing catheter 1266. As shown in FIG. 71, the nebulizing catheter 1266 includes a sterile sheath 1268 which is similar to the sheath included on the suction catheter 1262. In the embodiment of FIG. 71, the suction catheter 1256 and the nebulizing catheter 1266 are positioned alternately inside the ventilation lumen of the endotracheal tube 1252. The suction catheter or the nebulizing catheter can be withdrawn temporarily and maintained in its sterile sheath while the other is being used.

Referring to FIG. 72 there is another arrangement for connecting a suction catheter and nebulizing catheter to an endotracheal tube. In this embodiment, a manifold 1270 connects to the proximal end of the endotracheal tube 1252. The manifold 1270 has port 1274 for receiving the nebulizing catheter 1266 and a second port 1276. A distal manifold 1278 of a suction catheter 1280 connects to the second port 1276. The suction catheter manifold 1278 has a port 1282 for connecting to the ventilator. This arrangement can be used similarly to the arrangement of FIG. 71.

FIG. 73 shows still another arrangement for connecting a suction catheter and a nebulizing catheter to an endotracheal tube. In this embodiment, the endotracheal tube 1252 is provided with a proximal end that includes dual ports. A first port 1284 receives the nebulizing catheter 1266. The second port 1286 may be connected to either directly to a ventilator or may be connected to a distal end of a suction catheter (not shown) in a conventional manner.

In another alternative embodiment (not shown), the nebulizing catheter could be positioned down the suction lumen of the suction catheter.

FIG. 74 shows another embodiment of a suction catheter also incorporating a nebulization of an aerosol. In FIG. 74, a suction catheter 1400 is extends from the ventilation lumen of an endotracheal tube 1250. The suction catheter 1400 includes distal suction orifices 1402 located close to the distal end of the suction catheter shaft. Located along the suction catheter shaft proximally of the suction orifices 1402 are one or more pairs of liquid and gas orifices 1404. The liquid and gas orifice pairs 1404 are located with respect to each other to produce an aerosol of the liquid being delivered to the liquid orifice as in the previous embodiments. The nebulization orifices 1404 are oriented radially from the suction catheter shaft to direct the aerosol delivered from the nebulization orifices 1404 toward the airway passage wall. In one embodiment, the aerosol being delivered is a mucolytic agent. The suction provided by the suction orifices draws the mucolytic agent delivered from the nebulization orifices as well as mucous treated by the mucolytic agent in a distal direction into the suction orifices 1402.

Another embodiment of the suction catheter with aerosol delivery is shown in FIG. 75. A suction catheter 1410 is located in a ventilation lumen of the endotracheal tube 1250. As in the previous embodiment, the suction catheter 1410 has a distal suction orifice 1412 for removing mucous from the airway passage. In addition, the suction catheter 1410 also includes distal gas and liquid orifices 1414 located in proximity to each other to produce a aerosol. The liquid and gas orifices are located in a distal extension 1416 of the suction catheter shaft so that they are distal of the suction orifice 1412. The liquid and gas nebulization orifices 1414 are oriented in a proximal direction toward the suction orifice 1412. The distal extension 1416 is formed to bring the nebulization orifices 1414 close to the wall of airway passage so that the aerosol delivered from the nebulization orifices 1414 washes the airway passage wall. As in the previous embodiment, the aerosol delivered may be a mucolytic agent to facilitate suctioning of the mucous out of the airway passage. The pressurized gas flow may be used to contribute to the dislodgement of mucous from the airway passage walls.

F. Nebulization with Vibration

A vibrating orifice, a screen with multiple orifices or perforations, or a vibrating wire located at the distal tip of the nebulizing catheter may also be employed to assist in the generation of fine aerosol particles. The vibration may be generated by electromechanical, hydraulic, pneumatic, or piezoelectric means. The vibrations may be generated at the tip of the catheter, in the shaft, or extracorporeally.

One embodiment of a nebulizing catheter incorporating a vibrating tip is shown in FIG. 76. A nebulizing catheter 1300 includes a shaft 1302 through which extend a lumen 1304 for the delivery of a liquid medicine and a lumen 1306 for the delivery of a pressurized gas. The liquid lumen 1304 communicates with a distal liquid orifice 1308 and the gas lumen 1306 communicates with a distal gas orifice 1310 located at a distal end of the nebulizing catheter shaft. At the tip the orifices 1308 and 1310 may be drilled or formed in a piezoelectric material 1314 or may be drilled or formed in an orifice insert, plate, tube or screen mechanically attached to the tip such that the vibrations of the material are transferred to orifices. Although both the gas and liquid orifices may be vibrated, alternatively only the liquid orifice may be vibrated. In still a further embodiment, the entire shaft of the catheter may be vibrated so that the vibrations are transferred to the tip. The vibrations may be amplified by mechanical means to increase the amplitude of the orifice oscillation. Two electrical lead wires 1316 and 1318 may be used to conduct bipolar or unipolar pulses from an extracorporeal generator and control circuit to the piezoelectric material 1314. The amplitude and frequency of the orifice vibrations may be adjusted to optimize aerosol production based on the gas and solution flow rates, the orifice configuration, and the desired size of the aerosol particles. The generation device would be provided with a current leakage sensor to terminate its operation in the event it detects current leakage in the system. The vibrations can be pulsed to coincide with inspiration and also to control heat generated by vibration at the tip. One or more gas supply lumens and orifices at the catheter tip can be used to assist in the dispersion and transport of the particles produced at the vibrating orifice.

In a further alternative embodiment, the orifice may be vibrated by means of a vibrating wire connected to the orifice that is caused to vibrate from a generator connected to the proximal end. In still a further embodiment, a vibrating wire, similar to the wire tip shown in FIGS. 16–19, may extend distally past a non-vibrating orifice to cause aerosolization of a liquid delivered from the orifice that impinges onto the vibrating wire. In a still further embodiment, the tip may be vibrated remotely, e.g. from a source outside the body, by means of a magnetic field.

A liquid supply to the catheter tip can also be rapidly pulsed to cause small droplets to be ejected at the solution orifice. This may cause a finer aerosol to be developed than by feeding a continuous stream of solution to the orifice. The pulsation can be accomplished by rapidly expanding and contracting all or part of the solution reservoir (including the lumen). The expansion and contraction of the reservoir can be caused by electromechanical, hydraulic, pneumatic, or piezoelectric actuators forming the reservoir, within the reservoir or moving flexible portions of the reservoir. Such an embodiment is shown in FIG. 76. A nebulizing catheter 1500 includes a shaft 1502 having a gas lumen 1502 connected to a source of pressurized gas 1504 and a liquid medicine lumen 1506 connected to a source of liquid medicine 1508. Included in the liquid medicine source 1508 is a means for imparting compression waves or pulsation into the liquid. The waves are indicated in the liquid at 1509. The wave imparting means may be a transducer 1510 or other similar device. The vibration inducing device 1510 may be driven by a frequency generator 1513 at a frequency greater than 100 hertz. The vibrations induced in the liquid may be focussed or directed toward the distal liquid orifice 1514.

In the case where the vibrations are generated at a location proximal of the tip, the nebulizing catheter shaft may incorporate a mechanical means in the shaft or near the orifices capable of transmitting or amplifying the pulsations. In the embodiment of FIG. 77, a wire 1516 may extend from the pulsation generating means 1510 into the liquid lumen 1506 to help convey the vibrations 1509 to the distal orifice 1514. The pulsations imparted to the liquid may be used to generate an aerosol from the distal liquid orifice 1514 or alternatively may be used in conjunction with the pressurized gas delivered through the gas lumen 1502 for enhanced aerosolization. The amplitude and frequency of the orifice vibrations may be adjusted to optimize aerosol production based on the gas and solution flow rates, the orifice configuration, and the desired size of the aerosol particles.

The volume dispersed from the liquid orifice 1514 by each pulse should be less than approximately 10 microliters and the pulsation should occur at a frequency greater than 100 Hertz, although smaller volumes and faster frequencies may be used to produce a finer aerosol. It is preferable that the reservoir and lumens be constructed or a material of minimal compliance to ensure minimal attenuation of the pulsation. The gas supply orifice at the catheter tip can be used to assist in the dispersion and transport of the particles produced at the solution orifice. These micro pulsations can be incorporated into a series with pauses between them to coincide with the patient's inspiratory phase.

G. Other Method for Aerosol Generation

The above embodiments describe a nebulization catheter in which an aerosol is generated by directing a pressurized gas through a catheter near an orifice from which the liquid to be nebulized exits. It is considered to be within the scope of the invention described herein to use other means or agents to generate an aerosol for delivery of a medication to the respiratory tract. For example, the above embodiments may be used in conjunction with devices that utilize other means to generate an aerosol of a liquid medication. A liquid delivered by a single liquid lumen may be nebulized by applying ultrasonic energy to the liquid, electrospray, steam, or a micropump similar to those used in ink jet type printers. These alternative approaches to nebulization may be substituted for the use of a pressurized gas for some of the embodiments described above, or may be combined with pressurized gas or with each other to produce an aerosol of the liquid medication.

The nebulization catheter embodiments described herein could also be used in other types of nebulizers that are used externally of a patient's respiratory system, such as small volume nebulizers (SVN), humidification nebulizers, or nebulizers used for ocular or nasal drug administration. When used in such other types of nebulizers, the embodiments of the nebulization catheter disclosed herein provide for a fine aerosol without the potential disadvantages of impacting the liquid on a baffle or recirculating the liquid medicine on a continuous basis which are common in such nebulizers.

It is intended that the foregoing detailed description be regarded as illustrative rather than limiting and that it is understood that the following claims including all equivalents are intended to define the scope of the invention.

I claim:

1. A method for delivering a medicine to a patient, comprising:

positioning an endotracheal tube in the patient;

positioning a nebulization catheter in the patient; and operating the nebulization catheter to produce an aerosol of the medicine at a distal end of the nebulization catheter while the endotracheal tube is positioned in the patient by applying an electric signal to the distal end of the nebulization catheter to produce the aerosol from said distal end.

2. The method of claim 1, wherein the endotracheal tube and the nebulization catheter are positioned in a respiratory system of the patient, and wherein the aerosol is delivered to the respiratory system.

3. The method of claim 2 in which the step of operating the nebulization catheter further comprises:

delivering a liquid medicine to a first orifice located at the distal end of the nebulization catheter; and delivering a pressurized gas to a second orifice located at the distal end of the nebulization catheter in proximity to the first orifice.

4. The method of claim 3 further comprising the steps of:

imparting pulsation to the liquid being delivered.

5. The method of claim 4 in which the pulsation is imparted at a frequency greater than 100 hertz.

6. The method of claim 4 in which the pulsation is applied to a proximal reservoir from which the liquid medicine is supplied.

7. The method of claim 4 in which the pulsation is associated with the delivery of less than approximately 10 microliters of liquid medicine.

8. The method of claim 4 in which the nebulization catheter is operated to produce the aerosol in synchronism with the patient's inhalation.

9. The method of claim 2 further comprising:

centering the nebulization catheter in the endotracheal tube.

10. The method of claim 2 in which the step of positioning a nebulization catheter further comprises:

positioning a nebulization catheter through an auxiliary lumen of the endotracheal tube.

11. The method of claim 2 further comprising:

removing the nebulization catheter while leaving the endotracheal tube in position in the patient's respiratory system.

12. The method of claim 2 further comprising:

providing a coaxial airflow to said distal end of said nebulization catheter to constrain aerosol therefrom.

13. The method of claim 2 further comprising:

providing humidification to the patient's respiratory system.

14. The method of claim 2 in which the nebulization catheter is positioned in a patient who has a tracheotomy.

15. The method of claim 2 in which the nebulization catheter is positioned via a tracheotomy tube.

16. The method of claim 2 in which production of the aerosol at the distal end of the nebulization catheter is synchronized with inhalation of the patient.

17. The method of claim 16 further comprising the step of: pulsing delivery of liquid.

18. The method of claim 17 further comprising the step of: pulsing delivery of gas.

19. The method of claim 16 further comprising the step of: pulsing delivery of gas.

20. The method of claim 16 in which production of the aerosol is begun in advance of the inhalation of the patient.

21. The method of claim 2 further comprising the steps of:

sensing a physiological condition of the patient, and operating the nebulization catheter to produce the aerosol as a function of the condition sensed.

22. The invention of claim 2 wherein the aerosol is produced by vibrating a distal orifice of the nebulizing catheter.

23. The invention of claim 22 wherein the vibrating is produced by a mechanical means in a shaft of the nebulization catheter.

24. The invention of claim 22 wherein the vibrating is produced by a mechanical means near the distal orifice of he nebulization catheter.

25. The method of claim 1 in which the step of positioning the nebulization catheter further comprising:

receiving an indication of the position of the nebulization catheter relative to the endotracheal tube.

26. The method of claim 25 in which the indication is a tactile indication.

27. The method of claim 25 in which the step of receiving an indication further comprises:

receiving a indication of a pressure variation at a distal end of the endotracheal tube as the distal end of the nebulization catheter is moved past.

28. The invention of claim 1 wherein the electric signal applied to the distal end of the nebulization catheter causes a vibration that produces the aerosol.

29. The invention of claim 1 wherein the electric signal applied to the distal end of the nebulization catheter is applied to a piezoelectric material.

30. The invention of claim 1 wherein the electric signal applied to produce an aerosol by ultrasonic vibration.

31. The invention of claim 1 wherein the electric signal applied to produce an aerosol by electrospray.

32. The invention of claim 1 wherein the electric signal applied to produce an aerosol from a single lumen of the catheter.

33. A method for delivering a medicine to a patient, comprising:

positioning an endotracheal tube in the patient;

positioning a nebulization catheter in the patient; and operating the nebulization catheter to produce an aerosol of the medicine at a distal end of the nebulization catheter while the endotracheal tube is positioned in the patient; and balancing airflow at the distal end of the nebulization catheter by withdrawing air through a vacuum lumen extending through the nebulization catheter.

34. The method of claim 33, wherein the endotracheal tube and the nebulization catheter are positioned in a respiratory system of the patient, and wherein the aerosol is delivered to the respiratory system.

35. The method of claim 34 in which the step of operating the nebulization catheter further comprises:

delivering a liquid medicine to a first orifice located at the distal end of the nebulization catheter; and delivering a pressurized gas to a second orifice located at the distal end of the nebulization catheter in proximity to the first orifice.

36. The method of claim 34 further comprising:
   removing the nebulization catheter while leaving the endotracheal tube in position in the patient's respiratory system.

37. The method of claim 34 further comprising:
   providing a coaxial airflow to said distal end of said nebulization catheter to constrain aerosol therefrom.

38. The method of claim 34 in which the step of positioning the nebulization catheter further comprises:
   receiving an indication of the position of the nebulization catheter relative to the endotracheal tube.

39. The method of claim 38 in which the indication is a tactile indication.

40. The method of claim 38 in which the step of receiving an indication further comprises:
   receiving a indication of a pressure variation at a distal end of the endotracheal tube as the distal end of the nebulization catheter is moved past.

41. The method of claim 34 in which production of the aerosol at the distal end of the nebulization catheter is synchronized with inhalation of the patient.

42. The method of claim 41 further comprising the step of:
   pulsing delivery of one of liquid arid gas through the nebulization catheter.

43. The method of claim 34 further comprising the steps of:
   sensing a physiological condition of the patient, and
   operating the nebulization catheter to produce the aerosol as a function of the condition sensed.

44. The method of claim 33 further comprising the step of:
   positioning the nebulization catheter in a working channel of a bronchoscope.

\* \* \* \* \*